United States Patent
Naya et al.

(10) Patent No.: US 6,864,984 B2
(45) Date of Patent: Mar. 8, 2005

(54) MEASURING METHOD AND APPARATUS USING ATTENUATION IN TOTAL REFLECTION

(75) Inventors: Masayuki Naya, Kaisei-machi (JP); Takashi Kubo, Kaisei-machi (JP); Nobuhiko Ogura, Kaisei-machi (JP); Nobufumi Mori, Kaisei-machi (JP)

(73) Assignee: Fuji Photo Film Co., Ltd., Kanagawa-Ken (JP)

( * ) Notice: Subject to any disclaimer, the term of this patent is extended or adjusted under 35 U.S.C. 154(b) by 288 days.

(21) Appl. No.: 09/959,645

(22) PCT Filed: Mar. 14, 2001

(86) PCT No.: PCT/JP01/01998

§ 371 (c)(1),
(2), (4) Date: Jan. 16, 2002

(87) PCT Pub. No.: WO01/69207

PCT Pub. Date: Sep. 20, 2001

(65) Prior Publication Data

US 2003/0189707 A1 Oct. 9, 2003

(30) Foreign Application Priority Data

Mar. 16, 2000 (JP) ........................................ 2000-073689
May 22, 2000 (JP) ........................................ 2000-149415
Feb. 7, 2001 (JP) ........................................ 2001-030445
Feb. 26, 2001 (JP) ........................................ 2001-049681

(51) Int. Cl.⁷ ........................... G01N 21/55; G01N 21/27
(52) U.S. Cl. ..................................................... 356/445
(58) Field of Search .......................................... 356/445

(56) References Cited

U.S. PATENT DOCUMENTS

| 4,979,821 A | 12/1990 | Schutt et al. | ............... 356/246 |
| 4,997,278 A | 3/1991 | Finlan et al. | ............... 356/128 |
| 5,017,009 A | 5/1991 | Schutt et al. | ............... 358/338 |
| 5,917,607 A | * 6/1999 | Naya | .................. 356/445 |

FOREIGN PATENT DOCUMENTS

| EP | 0 797 091 A1 | 9/1997 | .......... G01N/21/55 |
| JP | 61-226644 | 10/1986 | .......... G01N/21/64 |
| JP | 1-138443 | 5/1989 | .......... G01N/21/41 |
| JP | 5-5734 | 1/1993 | .......... G01N/33/48 |
| JP | 6-167443 | 6/1994 | .......... G01N/21/27 |
| JP | 7-159319 | 6/1995 | .......... G01N/21/41 |
| JP | 8-43407 | 2/1996 | .......... G01N/35/10 |
| JP | 10-239233 | 9/1998 | .......... G01N/21/27 |
| JP | 10-267841 | 10/1998 | .......... G01N/21/41 |
| JP | 10-281981 | 10/1998 | .......... G01N/21/27 |
| JP | 10-281982 | 10/1998 | .......... G01N/21/27 |
| JP | 10-300667 | 11/1998 | .......... G01N/21/41 |
| JP | 10-339374 | 12/1998 | ........... F16K/1/226 |
| JP | 10-339732 | 12/1998 | .......... G01N/35/00 |
| JP | 11-51857 | 2/1999 | .......... G01N/21/27 |
| JP | 2000-55805 | 2/2000 | .......... G01N/21/27 |
| JP | 2000-65729 | 3/2000 | .......... G01N/21/27 |
| JP | 2000-66008 | 3/2000 | ............ G02B/3/00 |

OTHER PUBLICATIONS

International Search Report Okamoto, "Spectrum Researches", vol. 47, No. 1(1998), pp. 21 to 23 & pp. 26 and 27.

* cited by examiner

Primary Examiner—F. L. Evans
(74) Attorney, Agent, or Firm—Sughrue Mion, PLLC

(57) ABSTRACT

A plurality of measuring units each comprising a dielectric block, a metal film layer which is formed on a surface of the dielectric block and a sample holder are supported on a support. The support is moved by a support drive means to bring in sequence the measuring units to a measuring portion comprising an optical system which projects a light beam emitted from a light source, and a photodetector which detects attenuation in total internal reflection by detecting the intensity of the light beam which is reflected in total internal reflection at the interface between the dielectric block and the metal film layer. In this measuring apparatus, lots of samples can be measured in a short time.

45 Claims, 35 Drawing Sheets

F I G . 7
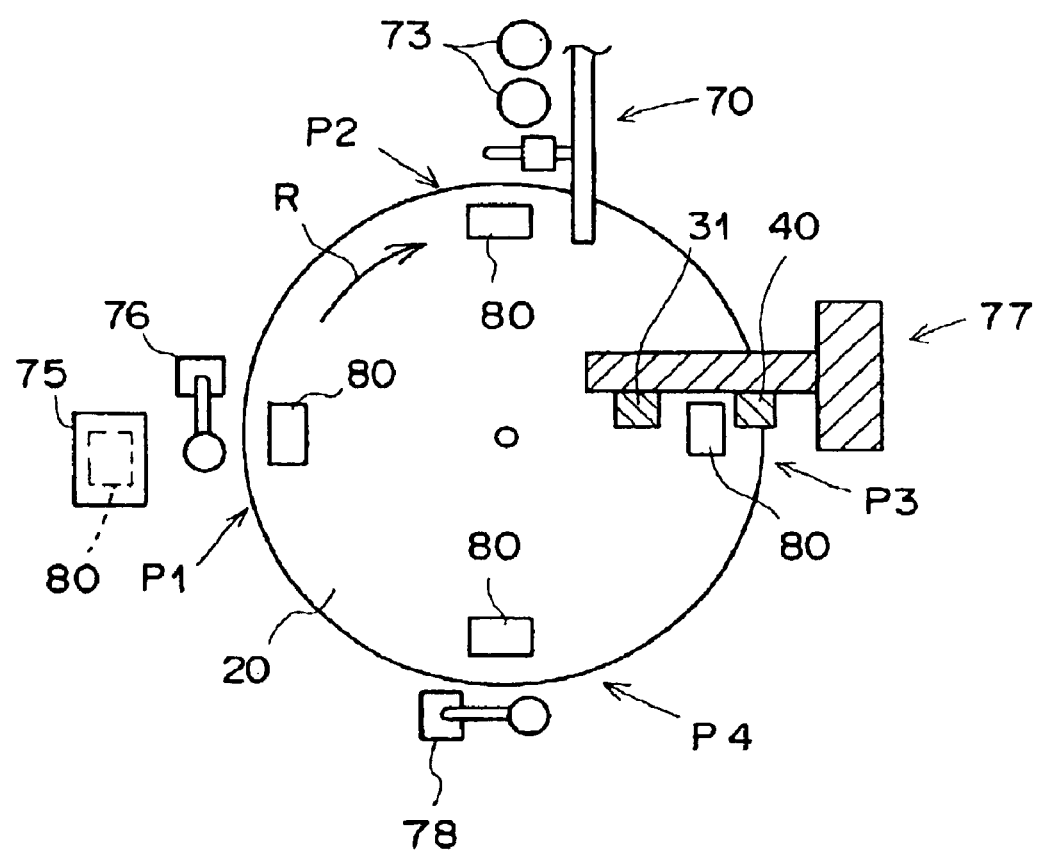

F I G . 12
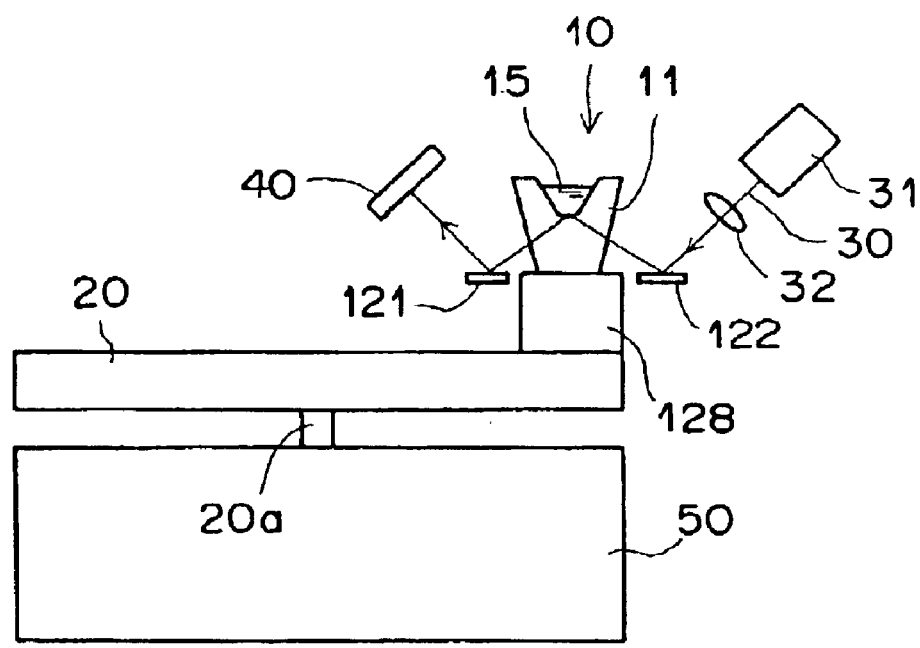

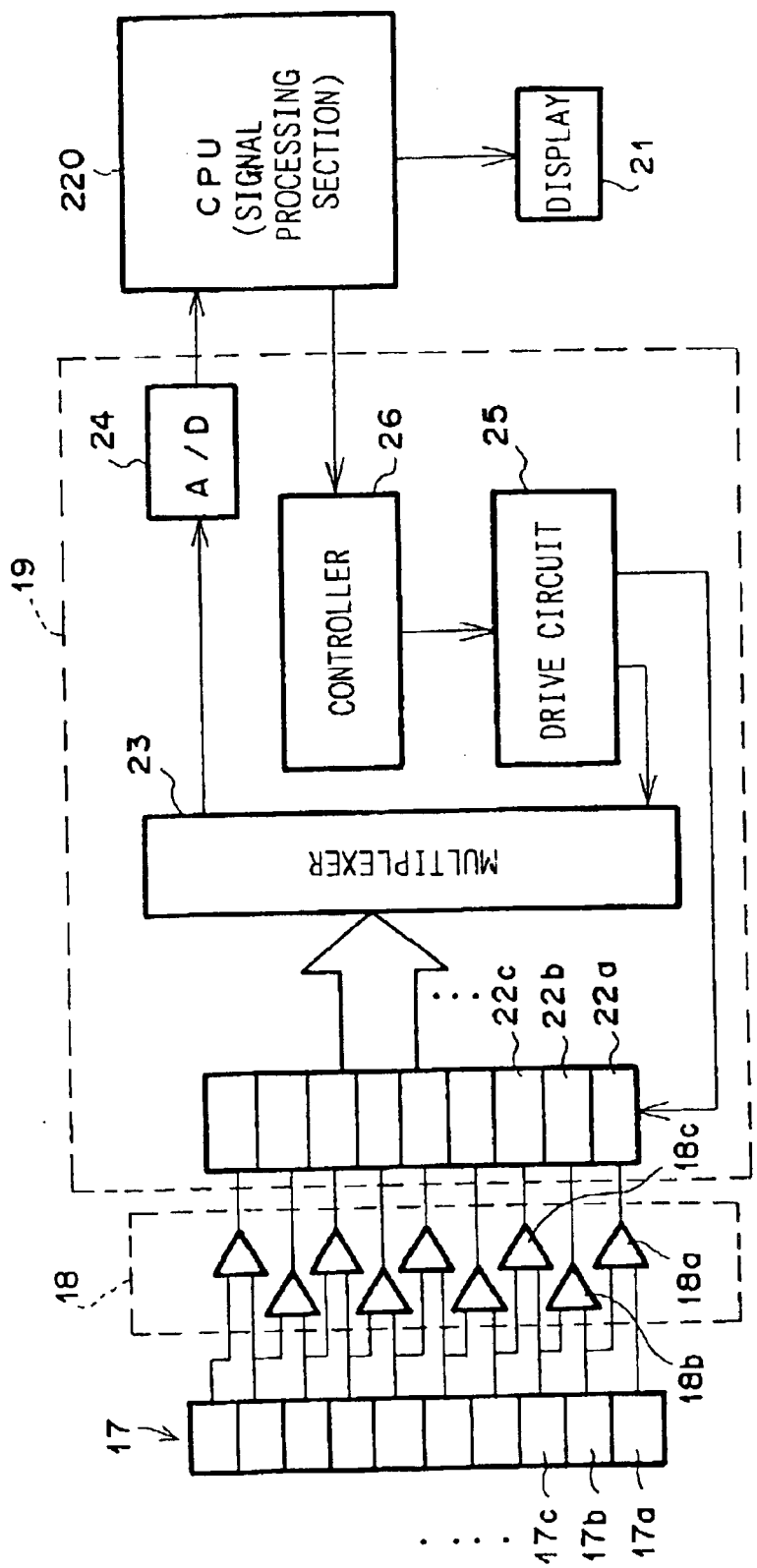

F I G. 17A
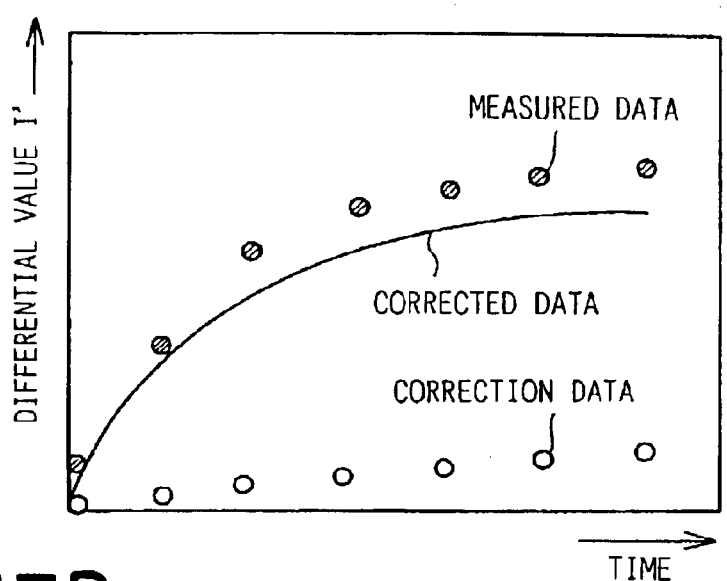
F I G. 17B
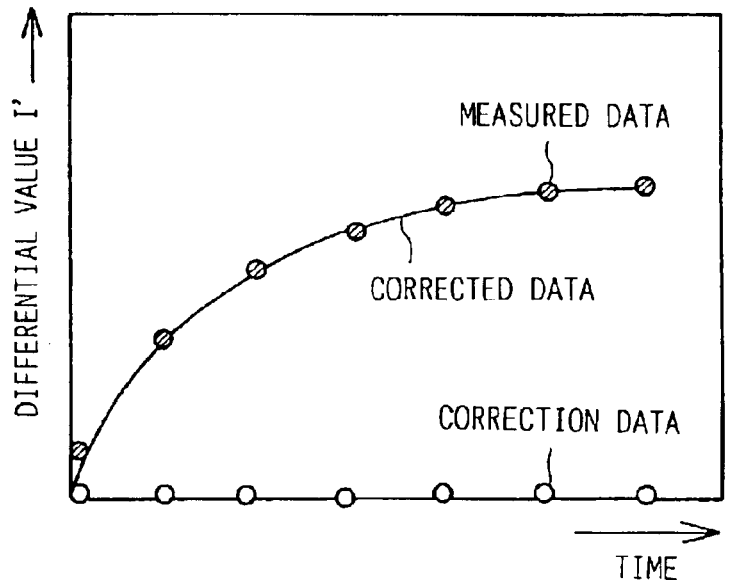

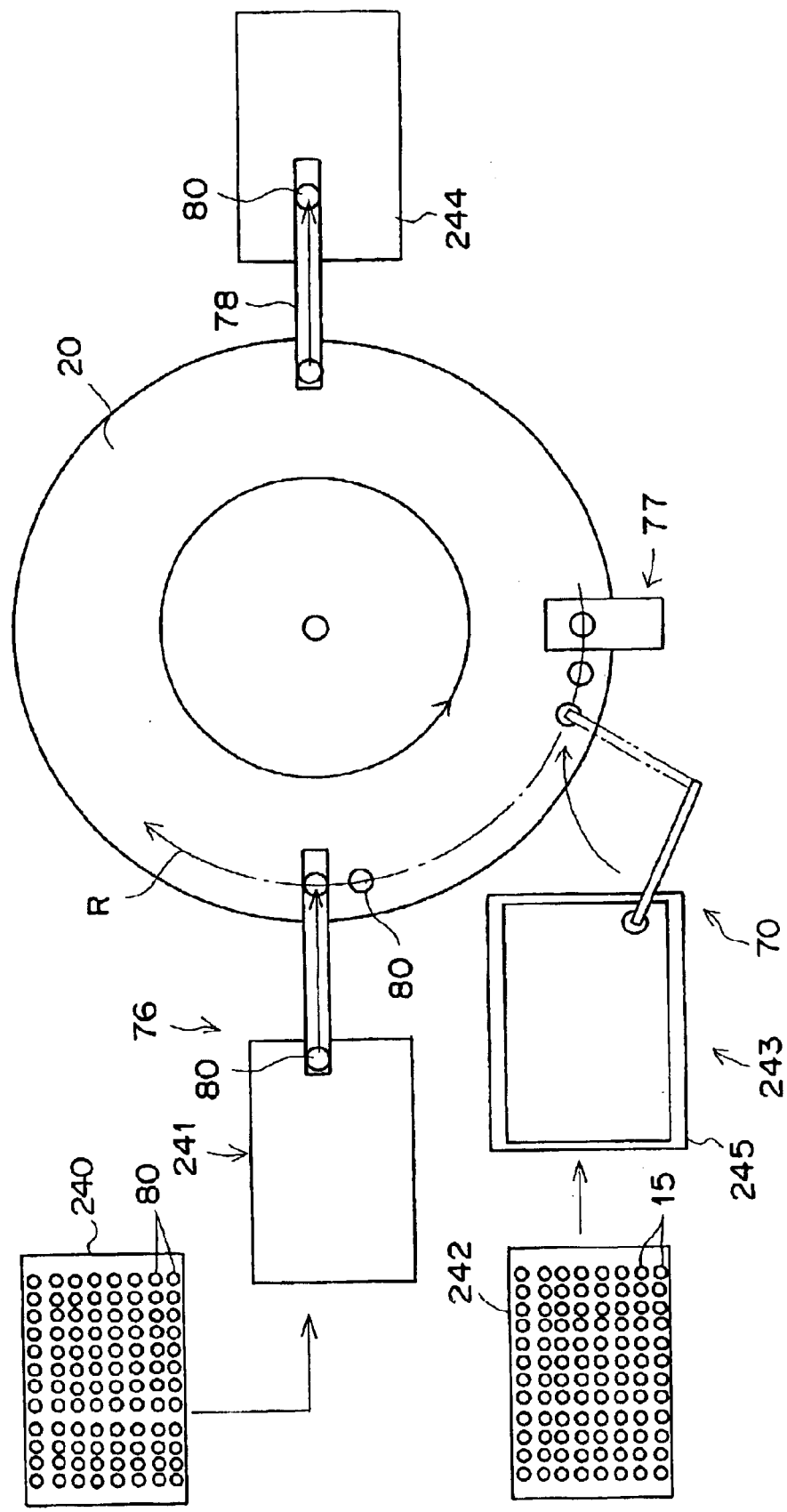

F I G .19
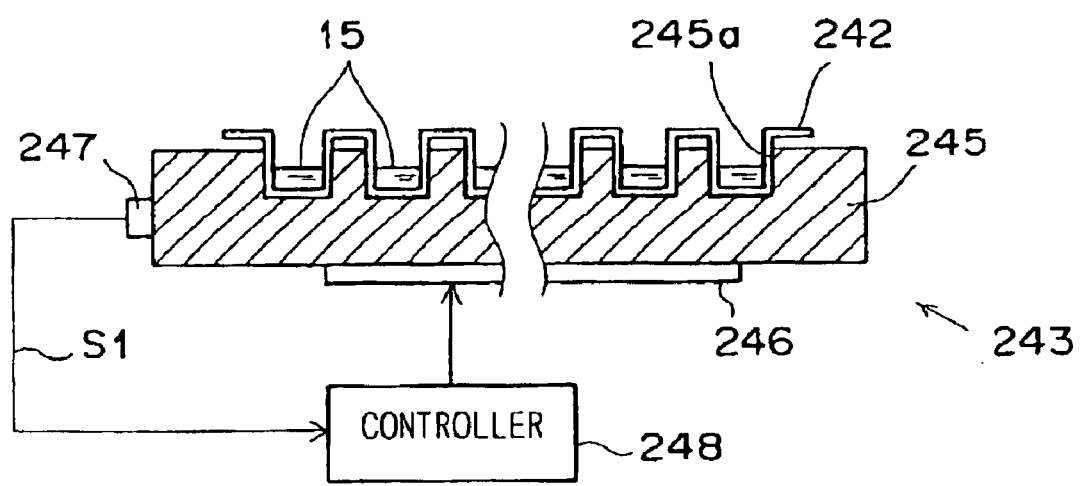

F I G . 20
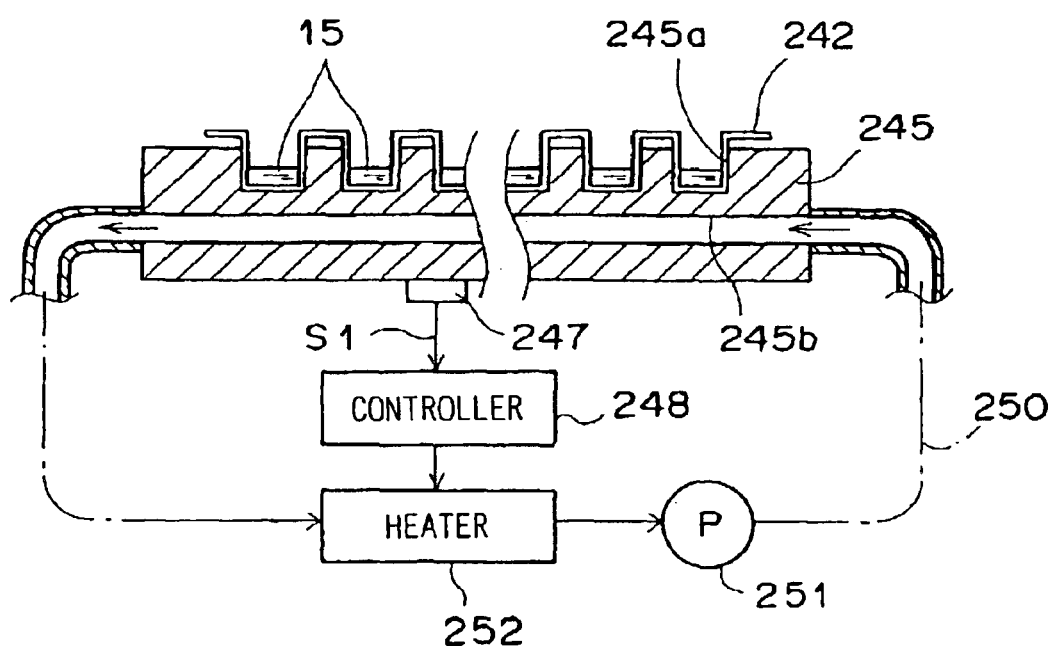

F I G . 21
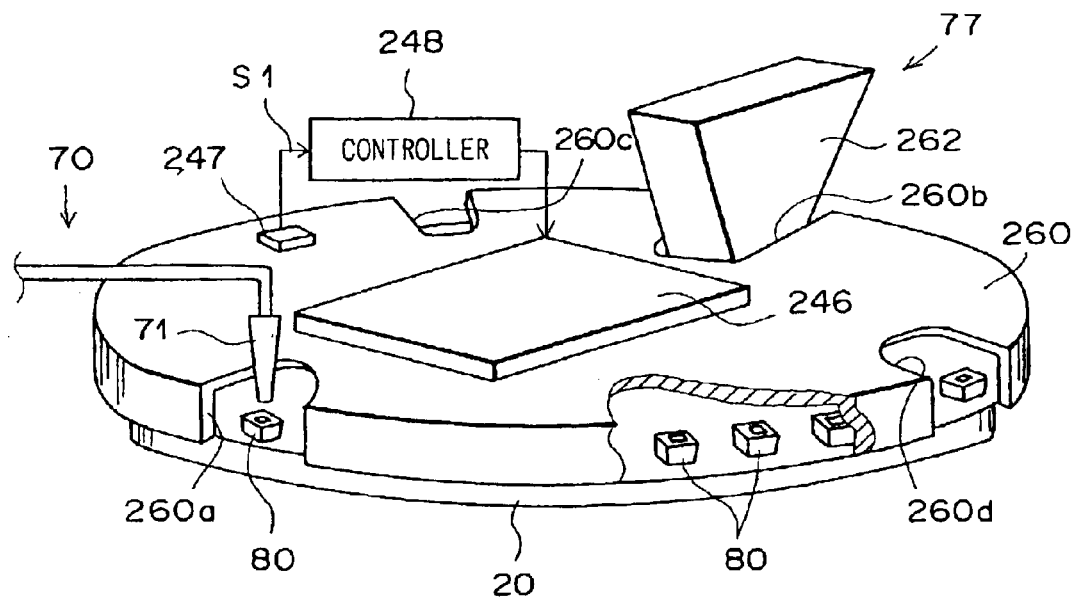

F I G . 24
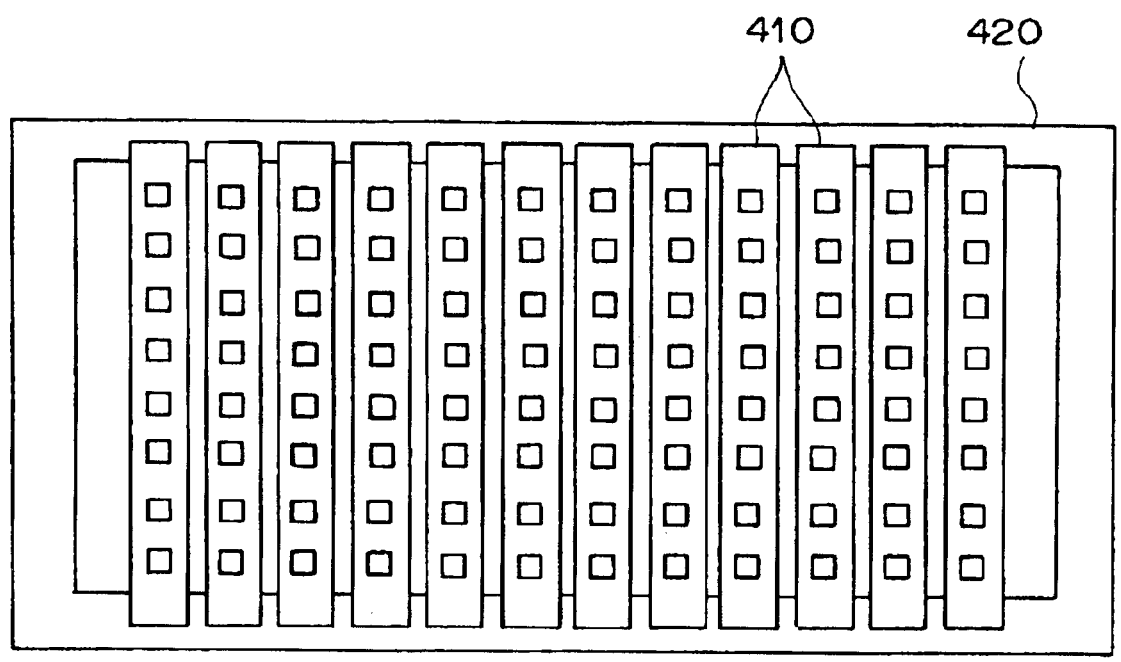

F I G . 26
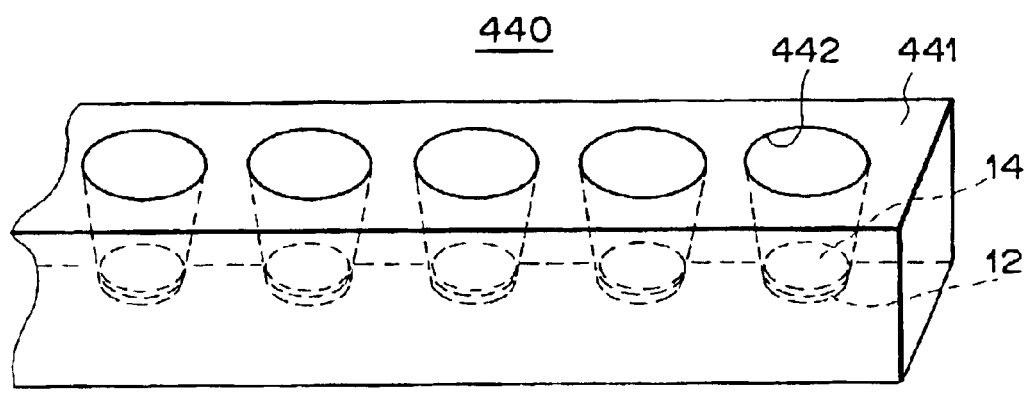

F I G . 31
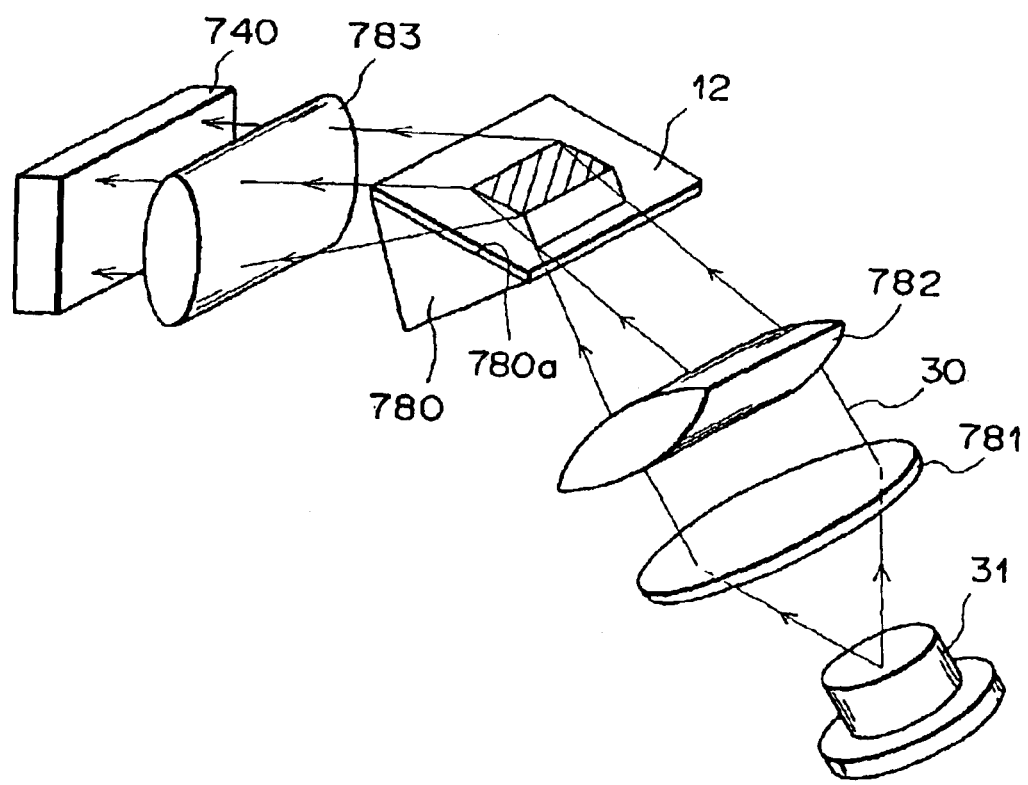

F I G .35
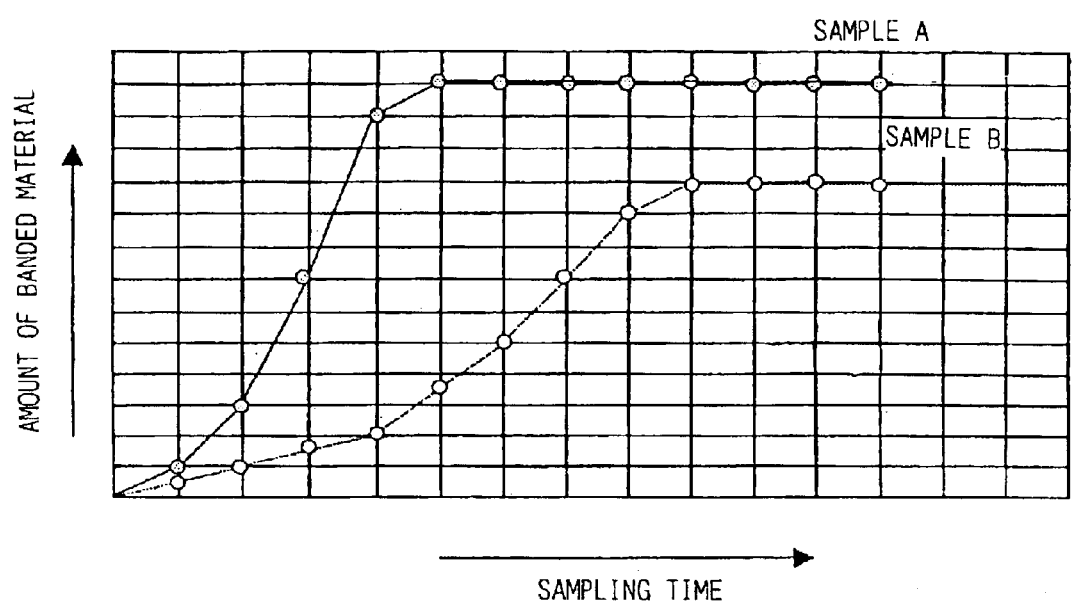

MEASURING METHOD AND APPARATUS USING ATTENUATION IN TOTAL REFLECTION

TECHNICAL FILED

This invention relates to a measuring apparatus using attenuation in total reflection such as a surface plasmon resonance sensor for quantitatively analyzing a material in a sample utilizing generation of surface plasmon.

This invention particularly relates to a measuring apparatus using attenuation in total reflection which can carries out measurement on lots of samples in a short time.

This invention also relates to a measuring method employed in such a measuring apparatus using attenuation in total reflection.

BACKGROUND ART

In metal, free electrons vibrate in a group to generate compression waves called plasma waves. The compression waves generated in a metal surface are quantized into surface plasmon.

There have been proposed various surface plasmon resonance sensors for quantitatively analyzing a material in a sample utilizing a phenomenon that such surface plasmon is excited by light waves. Among those, one employing a system called "Kretschmann configuration" is best known. See, for instance, Japanese Unexamined Patent Publication No. 6(1994)-167443.

The surface plasmon resonance sensor using the Kretschmann configuration basically comprises a dielectric block shaped, for instance, like a prism, a metal film which is formed on one surface of the dielectric block and is brought into contact with a sample, a light source emitting a light beam, an optical system which causes the light beam to enter the dielectric block so that the total internal reflection condition is satisfied at the interface of the dielectric block and the metal film and various angles of incidence of the light beam to the interface of the dielectric block and the metal film including an angle of incidence at which surface plasmon is generated can be obtained, and a photodetector which detects the intensity of the light beam reflected in total internal reflection at the interface and detects the state of surface plasmon resonance.

Various angles of incidence of the light beam to the interface can be obtained in the following two ways.

(1) A relatively thin light beam is deflected to impinge upon the interface at various angles.
(2) A relatively thick light beam is caused to impinge upon the interface in the form of convergent light so that components of the light beam impinge upon the interface at various angles.

In the former case, the light beam which is reflected from the interface at an angle which varies as the incident light beam is deflected may be detected by a photodetector which is moved in synchronization with deflection of the incident light beam or by an area sensor extending in the direction in which reflected light beam is moved as a result of deflection. In the latter case, an area sensor which extends in a direction in which all the components of light reflected from the interface at various angles can be detected may be used. In Japanese Unexamined Patent Publication No. 1(1989)-138443, there is disclosed an apparatus using the latter way in obtaining various angles of incidence of the light beam to the interface.

In such a surface plasmon resonance sensor, when a light beam impinges upon the interface at a particular angle of incidence θsp not smaller than the angle of total internal reflection, evanescent waves having an electric field distribution in the sample in contact with the metal film are generated and surface plasmon is excited in the interface between the metal film and the sample. When the wave vector of the evanescent waves is equal to the wave number of the surface plasmon and wave number matching is established, the evanescent waves and the surface plasmon resonate and light energy is transferred to the surface plasmon, whereby the intensity of light reflected in total internal reflection at the interface of the dielectric block and the metal film sharply drops. The sharp intensity drop is generally detected as a dark line by the photodetector.

The aforesaid resonance occurs only when the incident light beam is p-polarized. Accordingly, it is necessary to set the light beam to impinge upon the interface in the form of p-polarized light.

When the wave number of the surface plasmon can be known from the angle of incidence θsp at which the phenomenon of attenuation in total internal reflection (ATR) takes place, the dielectric constant of the sample can be obtained. That is, $$K_{sp}(\omega) = \frac{\omega}{c}\sqrt{\frac{\varepsilon_m(\omega)\varepsilon_s}{\varepsilon_m(\omega)+\varepsilon_s}}$$

wherein $K_{sp}$ represents the wave number of the surface plasmon, $\omega$ represents the angular frequency of the surface plasmon, c represents the speed of light in a vacuum, and $\varepsilon_m$ and $\varepsilon_s$ respectively represent the dielectric constants of the metal and the sample.

When the dielectric constant $\varepsilon_s$ of the sample is known, the concentration of a specific material in the sample can be determined on the basis of a predetermined calibration curve or the like. Accordingly, a specific component in the sample can be quantitatively analyzed by detecting the angle of incidence θsp at which the intensity of light reflected in total internal reflection from the interface of the prism and the metal film sharply drops.

As a similar apparatus utilizing the phenomenon of attenuation in total internal reflection (ATR), there has been known a leaky mode sensor described in, for instance, "Spectrum Researches" Vol.47, No.1 (1998), pp21 to 23 & pp26 and 27. The leaky mode sensor basically comprises a dielectric block shaped, for instance, like a prism, a clad layer which is formed on one face of the dielectric block, an optical waveguide layer which is formed on the clad layer and is brought into contact with a sample, a light source emitting a light beam, an optical system which causes the light beam to enter the dielectric block at various angles of incidence so that total internal reflection conditions are satisfied at the interface of the dielectric block and the clad layer and various angles of incidence of the light beam to the interface of the dielectric block and the clad layer including an angle of incidence at which attenuation in total internal reflection is caused by excitation of an optical waveguide mode at the optical waveguide layer can be obtained, and a photodetector means which detects the intensity of the light beam reflected in total internal reflection at the interface thereby detecting an excited state of the waveguide mode, i.e., attenuation in total internal reflection.

In the leaky mode sensor with this arrangement, when the light beam is caused to impinge upon the clad layer through the dielectric block at an angle not smaller than an angle of total internal reflection, only light having a particular wave number and impinging upon the optical waveguide layer at a particular angle of incidence comes to propagate through the optical waveguide layer in a waveguide mode after passing through the clad layer. When the waveguide mode is thus excited, almost all the incident light is taken in the optical waveguide layer and accordingly, the intensity of light reflected in total internal reflection at the interface of the dielectric block and the clad layer sharply drops. That is, attenuation in total internal reflection occurs. Since the wave number of light to be propagated through the optical waveguide layer in a waveguide mode depends upon the refractive index of the sample on the optical waveguide layer, the refractive index and/or the properties of the sample related to the refractive index can be detected on the basis of the angle of incidence at which the attenuation in total internal reflection occurs.

Also in the leaky mode sensor, various angles of incidence of the light beam to the interface can be obtained in the aforesaid two ways.

The surface plasmon resonance sensor and the leaky mode sensor are sometimes used in random screening for finding a specific material combined with a predetermined sensing material in the field of medicine creation. In this case, a sensing material is fixed on the film layer (the metal film layer in the case of the surface plasmon resonance sensor and the clad layer and the optical waveguide layer in the case of the leaky mode sensor), and a sample liquid containing a material to be analyzed is spotted on the sensing material. Then the angle of incidence θsp at which attenuation in total internal reflection takes place is repeatedly measured each time a predetermined time lapses.

When the sample material (the material to be analyzed in the sample liquid) is combined with the sensing material, the refractive index changes with time due to combination with the sample material. Accordingly, by measuring the angle of incidence θsp at which attenuation in total internal reflection takes place for every predetermined time, thereby detecting states of combination of the sample material with the sensing material, whether the sample material is a specific material to be combined with the sensing material can be known. As combinations of such a specific material and a sensing material, there has been known an antigen and an antibody. For example, there has been known measurement of detecting combination of a sample material with rabbit antihuman IgG antibody (sensing material).

In order to detect the state of combination of the sample material with the sensing material, the total reflection attenuation angle θsp (the angle of incidence θsp at which attenuation in total internal reflection takes place) itself need not necessarily be detected. For example, change in the total reflection attenuation angle θsp after the sample liquid is spotted onto the sensing material is measured and the state of combination of the sample material with the sensing material may be measured on the basis of the change of the total reflection attenuation angle θsp.

In the apparatuses utilizing the phenomenon of attenuation in total internal reflection such as a surface plasmon resonance sensor or a leaky mode sensor which have been put into practice, there has been a problem that a long time is required to measure lots of samples. For example, when each sample is to be subjected to measurement a plurality of times at predetermined time intervals, measurement of a second sample cannot be started until measurement of a first sample is finished, which results in a very long time required to measure all the samples.

In view of the foregoing observations and description, a first object of the present invention is to provide a measuring apparatus utilizing the phenomenon of attenuation in total internal reflection which can measure lots of samples in a short time.

A second object of the present invention is to provide a measuring method utilizing the phenomenon of attenuation in total internal reflection which makes it feasible to measure lots of samples in a short time in the case where each sample is to be subjected to measurement a plurality of times at time intervals.

Further, in conventional surface plasmon resonance sensors, there has been a problem that measurements can greatly fluctuate when light beam in the form of convergent light is caused to enter the dielectric block in the aforesaid way (1) in order to obtain various angles of incidence of the light beam to the interface of the dielectric block and the metal film. For example, the fluctuation in the measurements is detected as fluctuation in the position of the dark line described above.

The similar problem is recognized also in conventional leaky mode sensors when light beam is caused to enter the dielectric block in the aforesaid way (1) in order to obtain various angles of incidence of the light beam to the interface of the dielectric block and the clad layer.

Thus a third object of the present invention is to prevent generation of great fluctuation in the measurements and improve the measuring accuracy in the apparatuses utilizing the phenomenon of attenuation in total internal reflection where the light beam is caused to enter the dielectric block in the form of convergent light.

A fourth object of the present invention is to improve the measuring accuracy in a measuring method utilizing the phenomenon of attenuation in total internal reflection.

SUMMARY OF THE INVENTION

A first measuring apparatus utilizing the phenomenon of attenuation in total internal reflection for accomplishing the first object of the present invention comprises a plurality of measuring units each comprising a dielectric block, a film layer which is formed on a surface of the dielectric block and a sample holder which holds a sample on the surface of the film layer, a support which supports the measuring units, a light source which emits a light beam, an optical system which causes the light beam to enter the dielectric block at various angles of incidence so that the total internal reflection condition is satisfied at the interface of the dielectric block and the film layer, a photodetector which detects attenuation in total internal reflection by detecting the intensity of the light beam which is reflected in total internal reflection at the interface, and a drive means which moves the support relatively to the optical system and the photodetector to bring the measuring units in sequence to a predetermined position with respect to the optical system and the photodetector where the total internal reflection condition is satisfied at the interface of the dielectric block and the film layer and various angles of incidence to the interface can be obtained.

A second measuring apparatus utilizing the phenomenon of attenuation in total internal reflection for accomplishing the first object of the present invention comprises a plurality of measuring units each comprising a dielectric block, a film layer which is formed on a surface of the dielectric block, sensing material which interacts a specific component in a sample and is disposed on the surface of the film layer, and a sample holder which holds the sample on the surface of the sensing material, a support which supports the measuring units, a light source which emits a light beam, an optical system which causes the light beam to enter the dielectric block at various angles of incidence so that the total internal reflection condition is satisfied at the interface of the dielectric block and the film layer, a photodetector which detects attenuation in total internal reflection by detecting the intensity of the light beam which is reflected in total internal reflection at the interface, and a drive means which moves the support relatively to the optical system and the photodetector to bring the measuring units in sequence to a predetermined position with respect to the optical system and the photodetector where the total internal reflection condition is satisfied at the interface of the dielectric block and the film layer and various angles of incidence to the interface can be obtained.

A third measuring apparatus utilizing the phenomenon of attenuation in total internal reflection for accomplishing the first object of the present invention is arranged to measure utilizing especially the phenomenon of attenuation in total internal reflection by the aforesaid surface plasmon resonance and comprises a plurality of measuring units each comprising a dielectric block, a metal film layer which is formed on a surface of the dielectric block and a sample holder which holds a sample on the surface of the metal film layer, a support which supports the measuring units, a light source which emits a light beam, an optical system which causes the light beam to enter the dielectric block at various angles of incidence so that the total internal reflection condition is satisfied at the interface of the dielectric block and the metal film layer, a photodetector which detects attenuation in total internal reflection by surface plasmon resonance by detecting the intensity of the light beam which is reflected in total internal reflection at the interface, and a drive means which moves the support relatively to the optical system and the photodetector to bring the measuring units in sequence to a predetermined position with respect to the optical system and the photodetector where the total internal reflection condition is satisfied at the interface of the dielectric block and the metal film layer and various angles of incidence to the interface can be obtained.

A fourth measuring apparatus utilizing the phenomenon of attenuation in total internal reflection for accomplishing the first object of the present invention is also arranged to measure utilizing especially the phenomenon of attenuation in total internal reflection by the aforesaid surface plasmon resonance and comprises a plurality of measuring units each comprising a dielectric block, a metal film layer which is formed on a surface of the dielectric block, sensing material which interacts a specific component in a sample and is disposed on the surface of the metal film layer, and a sample holder which holds the sample on the surface of the sensing material, a support which supports the measuring units, a light source which emits a light beam, an optical system which causes the light beam to enter the dielectric block at various angles of incidence so that the total internal reflection condition is satisfied at the interface of the dielectric block and the metal film layer, a photodetector which detects attenuation in total internal reflection by surface plasmon resonance by detecting the intensity of the light beam which is reflected in total internal reflection at the interface, and a drive means which moves the support relatively to the optical system and the photodetector to bring the measuring units in sequence to a predetermined position with respect to the optical system and the photodetector where the total internal reflection condition is satisfied at the interface of the dielectric block and the metal film layer and various angles of incidence to the interface can be obtained.

A fifth measuring apparatus utilizing the phenomenon of attenuation in total internal reflection for accomplishing the first object of the present invention is arranged to measure utilizing especially the phenomenon of attenuation in total internal reflection by the aforesaid excitation of the waveguide mode at an optical waveguide layer and comprises a plurality of measuring units each comprising a dielectric block, a film layer consisting of a clad layer formed on a surface of the dielectric block and an optical waveguide layer formed on the clad layer, and a sample holder which holds a sample on the surface of the film layer, a support which supports the measuring units, a light source which emits a light beam, an optical system which causes the light beam to enter the dielectric block at various angles of incidence so that the total internal reflection condition is satisfied at the interface of the dielectric block and the clad layer, a photodetector which detects attenuation in total internal reflection by excitation of waveguide mode at the optical waveguide layer by detecting the intensity of the light beam which is reflected in total internal reflection at the interface, and a drive means which moves the support relatively to the optical system and the photodetector to bring the measuring units in sequence to a predetermined position with respect to the optical system and the photodetector where the total internal reflection condition is satisfied at the interface of the dielectric block and the clad layer and various angles of incidence to the interface can be obtained.

A sixth measuring apparatus utilizing the phenomenon of attenuation in total internal reflection for accomplishing the first object of the present invention is arranged to measure utilizing especially the phenomenon of attenuation in total internal reflection by the aforesaid excitation of the waveguide mode at an optical waveguide layer and comprises a plurality of measuring units each comprising a dielectric block, a film layer consisting of a clad layer formed on a surface of the dielectric block and an optical waveguide layer formed on the clad layer, sensing material which interacts a specific component in a sample and is disposed on the surface of the film layer, and a sample holder which holds the sample on the surface of the sensing material, a support which supports the measuring units, a light source which emits a light beam, an optical system which causes the light beam to enter the dielectric block at various angles of incidence so that the total internal reflection condition is satisfied at the interface of the dielectric block and the clad layer, a photodetector which detects attenuation in total internal reflection by excitation of waveguide mode at the optical waveguide layer by detecting the intensity of the light beam which is reflected in total internal reflection at the interface, and a drive means which moves the support relatively to the optical system and the photodetector to bring the measuring units in sequence to a predetermined position with respect to the optical system and the photodetector where the total internal reflection condition is satisfied at the interface of the dielectric block and the clad layer and various angles of incidence to the interface can be obtained.

In the measuring apparatuses utilizing the phenomenon of attenuation in total internal reflection for accomplishing the first object of the present invention, for instance, the drive means moves the support with the optical system and the photodetector kept stationary.

In this case, it is preferred that the support be a turntable which supports the measuring units about its axis of rotation and the drive means be arranged to intermittently rotate the turntable. The support may support the measuring units in a row and the drive means may be arranged to intermittently move the support in the direction of the row of the measuring units.

Further, the drive means may move the optical system and the photodetector with the support kept stationary.

In this case, it is preferred that the support supports the measuring units in a circle and the drive means intermittently moves the optical system and the photodetector along the measuring units in a circle. The support may support the measuring units in a row and the drive means may be arranged to intermittently move the optical system and the photodetector along the measuring units in a row.

When the drive means is provided with a roller bearing which supports its rotating shaft, it is preferred that the drive means be arranged to rotate the rotating shaft in one direction when a set of measuring units on the support are measured and to rotate the rotating shaft in the other direction to return the rotating shaft to the original position after the measurement on the measuring units to wait in the original position for measurement on another set of measuring units.

Further, in the measuring apparatuses utilizing the phenomenon of attenuation in total internal reflection for accomplishing the first object of the present invention, it is preferred that the measuring units be connected in a row to form a measuring unit train, and the support be arranged to support the measuring unit train.

Further, in the measuring apparatuses utilizing the phenomenon of attenuation in total internal reflection for accomplishing the first object of the present invention, it is preferred that an automatic sample feeding means which automatically feeds a sample to the sample holder of each of the measuring units be provided.

Further, in the measuring apparatuses utilizing the phenomenon of attenuation in total internal reflection for accomplishing the first object of the present invention, it is preferred that the dielectric block of each measuring unit be fixed to the support while the film layer and the sample holder be integrated with each other to form a measuring chip, and the measuring chip be exchangeable with respect to the dielectric block.

In this case, it is preferred that the measuring apparatus be provided with a measuring chip cassette in which plurality of measuring chips are contained, and a chip supply means which takes out the measuring chips from the measuring chip cassette one by one and mounts each measuring chip on the dielectric block.

In another embodiment, the dielectric block, the film layer and the sample holder of the measuring unit are integrated with each other to form a measuring chip which is exchangeable with respect to the support.

In this case, it is preferred that the measuring apparatus be provided with a measuring chip cassette in which plurality of measuring chips are contained, and a chip supply means which takes out the measuring chips from the measuring chip cassette one by one and mounts each measuring chip on the support.

It is preferred that the optical system be arranged to cause the light beam to enter the dielectric block as a convergent light beam or a divergent light beam, and the photodetector be arranged to detect a position of a dark line which is generated in the light beam reflected in total internal reflection at the interface due to attenuation in total reflection.

Further, it is preferred that the optical system be arranged to cause the light beam to impinge upon the interface in a defocused state. In this case, it is preferred that the beam diameter of the light beam as measured on the interface in the direction of movement of the support be at least ten times the mechanical positioning accuracy of the support.

Further, in the measuring apparatuses utilizing the phenomenon of attenuation in total internal reflection for accomplishing the first object of the present invention, it is preferred that the measuring units be supported on the upper side of the support, the light source be arranged to emit the light beam downward from above the support, the optical system be provided with a reflecting member which reflects upward the light beam toward the interface.

Further, in the measuring apparatuses utilizing the phenomenon of attenuation in total internal reflection for accomplishing the first object of the present invention, it is preferred that the measuring units be supported on the upper side of the support, the optical system be arranged to cause the light beam to impinge upon the interface from below the interface, the photodetector is positioned above the support with its light receiving face directed downward, and a reflecting member which reflects the light beam, reflected in total internal reflection at the interface, upward toward the photodetector be provided.

Further, in the measuring apparatuses utilizing the phenomenon of attenuation in total internal reflection for accomplishing the first object of the present invention, it is preferred that a temperature control means which maintains the temperature of the measuring units at a predetermined temperature before and/or after the measuring units are supported by the support be provided.

Further, in the measuring apparatuses utilizing the phenomenon of attenuation in total internal reflection for accomplishing the first object of the present invention, it is preferred that a stirrer means which stirs the sample held by the sample holder of the measuring unit supported by the support before attenuation in total internal reflection is detected be provided.

Further, in the measuring apparatuses utilizing the phenomenon of attenuation in total internal reflection for accomplishing the first object of the present invention, it is preferred that a reference liquid supply means which supplies at least one of the measuring units supported by the support with reference liquid which has optical properties related to the optical properties of the sample be provided, and data on the state of attenuation in total internal reflection for the sample obtained by the photodetector be corrected on the basis of data on the state of total internal reflection for the reference liquid.

In the case where the sample comprises a sample material dissolved in solvent, it is preferred that the reference liquid supply means supplies the solvent as the reference liquid.

Further, it is preferred that the measuring apparatuses utilizing the phenomenon of attenuation in total internal reflection for accomplishing the first object of the present invention be provided with an identification mark provided on each of the measuring units, a reading means which reads out the identification mark from each of the measuring units subjected to the measurement, a sample information input means which inputs information on the samples fed to the respective measuring units, a display means which displays the result of the measurement, and a control means which is connected to the display means, the sample information input means and the reading means to store the identification mark for each measuring unit and the information on the sample fed to the measuring unit correlated to each other and causes the display means to display the result of the measurement on the sample held by a measuring unit in correlation with the identification mark for the measuring unit and the information on the sample fed to the measuring unit stored correlated to each other.

In the method for accomplishing the second object of the present invention, a measuring apparatus utilizing the phenomenon of attenuation in total internal reflection for accomplishing the first object of the present invention is employed, and the method for accomplishing the second object of the present invention comprises the steps of detecting attenuation in total internal reflection for the sample held in first one of the measuring units, moving the support relatively to the optical system and the photodetector to bring a second one of the measuring units to the predetermined position with respect to the optical system and the photodetector and detecting attenuation in total internal reflection for the sample held in the second one of the measuring units, and moving the support relatively to the optical system and the photodetector to bring the first one of the measuring units again to the predetermined position with respect to the optical system and the photodetector and detecting again attenuation in total internal reflection for the sample held in the first one of the measuring units.

A first measuring apparatus utilizing the phenomenon of attenuation in total internal reflection for accomplishing the third object of the present invention comprises a dielectric block, a film layer which is formed on one surface of the dielectric block and is brought into contact with a sample, a light source which emits a light beam, an optical system which causes the light beam to enter the dielectric block in convergent light so that the total internal reflection condition is satisfied at the interface of the dielectric block and the film layer and various angles of incidence of the light beam to the interface of the dielectric block and the film layer can be obtained, and a photodetector which detects attenuation in total internal reflection by detecting the intensity of the light beam which is reflected in total internal reflection at the interface, and is characterized in that the optical system is arranged so that the light beam is not focused on the interface.

A second measuring apparatus utilizing the phenomenon of attenuation in total internal reflection for accomplishing the third object of the present invention is arranged to measure utilizing especially the phenomenon of attenuation in total internal reflection by the aforesaid surface plasmon resonance and comprises a dielectric block, a metal film layer which is formed on one surface of the dielectric block and is brought into contact with a sample, a light source which emits a light beam, an optical system which causes the light beam to enter the dielectric block in convergent light so that the total internal reflection condition is satisfied at the interface of the dielectric block and the metal film layer and various angles of incidence of the light beam to the interface of the dielectric block and the metal film layer can be obtained, and a photodetector which detects attenuation in total internal reflection by surface plasmon resonance by detecting the intensity of the light beam which is reflected in total internal reflection at the interface, and is characterized in that the optical system is arranged so that the light beam is not focused on the interface.

A third measuring apparatus utilizing the phenomenon of attenuation in total internal reflection for accomplishing the third object of the present invention is in the form of a leaky mode sensor and comprises a dielectric block, a film layer which is formed of a clad layer formed on a surface of the dielectric block and an optical waveguide layer formed on the clad layer and is brought into contact with a sample, a light source which emits a light beam, an optical system which causes the light beam to enter the dielectric block in convergent light so that the total internal reflection condition is satisfied at the interface of the dielectric block and the clad layer and various angles of incidence of the light beam to the interface of the dielectric block and the clad layer can be obtained, and a photodetector which detects attenuation in total internal reflection by excitation of waveguide mode at the optical waveguide layer by detecting the intensity of the light beam which is reflected in total internal reflection at the interface, and is characterized in that the optical system is arranged so that the light beam is not focused on the interface.

In the measuring apparatuses utilizing the phenomenon of attenuation in total internal reflection for accomplishing the third object of the present invention, it is preferred that the light beam be at least 500 $\mu$m in a cross-sectional size at least in one direction on the interface (the interface of the dielectric block and the metal film layer in the case of the surface plasmon resonance sensor, the interface of the dielectric block and the clad layer in the case of the leaky mode sensor).

As the optical system, one which focuses the light beam so that the interface is positioned outside the focal depth of the light beam can be suitably employed. In this case, the focal depth means a range in which the beam diameter is within twice that at the focal point. Further, as the optical system, one which is arranged so that the light beam is not focused on the interface due to its aberration may also be employed.

For example, the optical system may comprise an optical system in which the light beam is converged in a conical shape by a spherical lens or an optical system in which the light beam is converged in a wedge-like shape by a cylindrical lens.

In the measuring apparatuses utilizing the phenomenon of attenuation in total internal reflection for accomplishing the third object of the present invention, it is preferred that a sensing medium which makes bonding reaction with a specific material in the sample be fixed on the film layer (the metal film layer in the case of the surface plasmon resonance sensor, the optical waveguide layer in the case of the leaky mode sensor). In this specification, the expression "the film layer is in contact with the sample" should be broadly interpreted to include a state where the film layer is in contact with the sample layer with such a sensing medium intervening therebetween.

Further, in the measuring apparatuses utilizing the phenomenon of attenuation in total internal reflection for accomplishing the third object of the present invention, it is preferred that a sample holder for holding the sample on the film layer and/or a sample introduction mechanism for introducing the sample onto the film layer be provided.

A first measuring method utilizing the phenomenon of attenuation in total internal reflection for accomplishing the fourth object of the present invention comprises the steps of
  bringing a sample into contact with a film layer formed on one surface of a dielectric block,
  causing a light beam to enter the dielectric block in convergent light so that the total internal reflection condition is satisfied at the interface of the dielectric block and the film layer and various angles of incidence of the light beam to the interface of the dielectric block and the film layer can be obtained, and
  detecting attenuation in total internal reflection by detecting the intensity of the light beam which is reflected in total internal reflection at the interface, and
  is characterized by the step of causing the light beam to enter the dielectric block not to be focused on the interface.

A second measuring method utilizing the phenomenon of attenuation in total internal reflection for accomplishing the fourth object of the present invention comprises the steps of
  bringing a sample into contact with a metal film layer formed on one surface of a dielectric block,
  causing a light beam to enter the dielectric block in convergent light so that the total internal reflection condition is satisfied at the interface of the dielectric block and the metal film layer and various angles of incidence of the light beam to the interface of the dielectric block and the metal film layer can be obtained, and
  detecting attenuation in total internal reflection by surface plasmon resonance by detecting the intensity of the light beam which is reflected in total internal reflection at the interface, and
  is characterized by the step of causing the light beam to enter the dielectric block not to be focused on the interface.

A third measuring method utilizing the phenomenon of attenuation in total internal reflection for accomplishing the fourth object of the present invention comprises the steps of
  bringing a sample into contact with an optical waveguide layer formed on a clad layer formed on one surface of a dielectric block,
  causing a light beam to enter the dielectric block in convergent light so that the total internal reflection condition is satisfied at the interface of the dielectric block and the clad layer and various angles of incidence of the light beam to the interface of the dielectric block and the clad layer can be obtained, and
  detecting attenuation in total internal reflection by detecting the intensity of the light beam which is reflected in total internal reflection at the interface, and
  is characterized by the step of causing the light beam to enter the dielectric block not to be focused on the interface.

It is preferred that the light beam is caused to enter the dielectric block so as to be at least 500 $\mu$m in a cross-sectional size at least in one direction on the interface.

DISCLOSURE OF THE INVENTION

In the measuring apparatuses utilizing the phenomenon of attenuation in total internal reflection for accomplishing the first object of the present invention, since a plurality of measuring units each comprising a dielectric block, a film layer (a metal film layer in the case of that utilizing surface plasmon resonance, a clad layer and an optical waveguide layer in the case of that utilizing excitation of waveguide mode), and the support is moved relatively to the optical system and the photodetector to bring the measuring units in sequence to a predetermined position with respect to the optical system and the photodetector, a plurality of measuring units carrying thereon samples can be subjected to the measurement in sequence, whereby lots of samples can be measured in a short time.

For example, when the support is a turntable which supports the measuring units about its axis of rotation and the drive means is arranged to intermittently rotate the turntable, or the support supports the measuring units in a row and the drive means is arranged to intermittently move the support in the direction of the row of the measuring units, measurement on lots of samples can be carried out at high efficiency.

Further, also when the support supports the measuring units in a circle and the drive means is arranged to intermittently rotate the optical system and the photodetector along the measuring units, or the support supports the measuring units in a row and the drive means is arranged to intermittently move the optical system and the photodetector along the row of the measuring units, measurement on lots of samples can be carried out at high efficiency.

In the measuring apparatuses utilizing the phenomenon of attenuation in total internal reflection for accomplishing the first object of the present invention in which sensing material which interacts a specific component in a sample is held on the surface of the film layer, the state of attenuation in total internal reflection, that is, the state of surface plasmon resonance or the state of excitation of waveguide mode, is changed by the interaction, and accordingly, the specific reaction between the specific material in the sample and the sensing material can be detected by detecting the change of the state of attenuation in total internal reflection.

When the drive means is provided with a roller bearing which supports its rotating shaft, and the drive means is arranged to rotate the rotating shaft in one direction when a set of measuring units on the support are measured and to rotate the rotating shaft in the other direction to return the rotating shaft to the original position after the measurement on the measuring units to wait in the original position for measurement on another set of measuring units, the angular position of the rollers of the roller bearing when a measuring unit on a given position of the support is brought to the predetermined position is constant, whereby deterioration in measuring accuracy due to fluctuation in the angular position of the rollers can be prevented.

Further, when the measuring units are connected in a row to form a measuring unit train and the support is arranged to support the measuring unit train, the measuring units can be accurately located in place and becomes easier to handle, which results in higher measuring efficiency.

Further, when the sample holder of each of the measuring units is provided with an automatic sample feeding means which automatically feeds a sample to the measuring unit, the time required to feed the sample to the measuring unit can be shortened, and lots of samples can be measured in a further shorter time.

Further, when the dielectric block of each measuring unit is fixed to the support while the film layer and the sample holder is integrated with each other to form a measuring chip, and the measuring chip is exchangeable with respect to the dielectric block, new samples can be subjected to measurement in sequence by replacing the measuring units which have been measured with measuring units loaded with other samples, whereby lots of samples can be measured in a further shorter time.

In this case, when a measuring chip cassette in which plurality of measuring chips are contained and a chip supply means which takes out the measuring chips from the measuring chip cassette one by one and mounts each measuring chip on the dielectric block are employed, supply of the measuring chips can be effectively carried out, whereby lots of samples can be measured in a further shorter time.

When the dielectric block, the film layer and the sample holder of the measuring unit are integrated with each other to form a measuring chip which is exchangeable with respect to the support, new samples can also be subjected to measurement in sequence by replacing the measuring units which have been measured with measuring units loaded with other samples, whereby lots of samples can be measured in a further shorter time.

Also in this case, when a measuring chip cassette in which plurality of measuring chips are contained and a chip supply means which takes out the measuring chips from the measuring chip cassette one by one and mounts each measuring chip on the dielectric block are employed, supply of the measuring chips can be effectively carried out, whereby lots of samples can be measured in a further shorter time.

In the case where the support is mechanically moved by the drive means, fluctuation in position of the support is inevitable. However fluctuation in position of the support results in fluctuation in position of the measuring unit with respect to the optical system, which results in an error in measuring attenuation in total internal reflection. For example, an error in detecting the position of the dark line representing attenuation total internal reflection can occur. As a cause for leading fluctuation in position of the support to an error in measuring attenuation in total internal reflection, fluctuation in the thickness of the film layer, the thickness of the sensing material layer and/or the reacting weight of the sensing material and the sample material by position is conceivable.

When the optical system is arranged to cause the light beam to impinge upon the interface in a defocused state, errors in detecting the state of attenuation in total internal reflection (e.g., detection of the position of the dark line) are averaged and as a result, the measuring accuracy is improved.

The measuring accuracy can be further higher when the beam diameter of the light beam as measured on the interface in the direction of movement of the support be at least ten times the mechanical positioning accuracy of the support. The reason is as follows. That is, in this case, since the positioning error is $1/10$ of the beam diameter at most and the remainder $9/10$ is constantly included in the measuring range, the signal error generated due to the positioning error can be suppressed to $1/10$, which is practically negligible in the normal quantitative analysis.

In the measuring apparatuses utilizing the phenomenon of attenuation in total internal reflection for accomplishing the first object of the present invention, when the measuring units are supported on the upper side of the support, the light source is arranged to emit the light beams downward from above the support, the optical system is provided with a reflecting member which reflects upward the light beam toward the interface, it becomes unnecessary to take into account interference between the support and the optical system including the light source, and the freedom in layout of the optical system and the light source as well as other elements which are to be disposed near the support can be increased.

Further, when the measuring units are supported on the upper side of the support, the optical system is arranged to cause the light beam to impinge upon the interface from below the interface, the photodetector is positioned above the support with its light receiving face directed downward, and a reflecting member which reflects the light beam, reflected in total internal reflection at the interface, upward toward the photodetector is provided, it becomes unnecessary to take into account interference between the support and the photodetector, and the freedom in layout of the photodetector as well as other elements which are to be disposed near the support can be increased.

When the measuring apparatuses utilizing the phenomenon of attenuation in total internal reflection for accomplishing the first object of the present invention is provided with a temperature control means which maintains the temperature of the measuring units at a predetermined temperature before and/or after the measuring units are supported by the support, deterioration in measuring accuracy due to change of temperature of the sample in the measuring unit can be prevented.

When the measuring apparatuses utilizing the phenomenon of attenuation in total internal reflection for accomplishing the first object of the present invention is provided with a stirrer means which stirs the sample held by the sample holder of the measuring unit supported by the support before attenuation in total internal reflection is detected, deterioration in measuring accuracy due to uneven concentration distribution of the sample material in the sample liquid can be prevented.

Further, in the measuring apparatuses utilizing the phenomenon of attenuation in total internal reflection for accomplishing the first object of the present invention, when a reference liquid supply means which supplies at least one of the measuring units supported by the support with reference liquid which has optical properties related to the optical properties of the sample is provided, and data on the state of attenuation in total internal reflection for the sample obtained by the photodetector is corrected on the basis of data on the state of total internal reflection for the reference liquid, change of the refractive index of the solvent of the sample, for instance, with change of the environmental temperature or the like, change of the properties of the optical system, for instance, with change of the environmental temperature, and the like can be compensated for and the properties of the sample material in the sample liquid can be correctly measured.

Further when the measuring apparatuses utilizing the phenomenon of attenuation in total internal reflection for accomplishing the first object of the present invention is provided with an identification mark provided on each of the measuring units, a reading means which reads out the identification mark from each of the measuring units subjected to the measurement, a sample information input means which inputs information on the samples fed to the respective measuring units, a display means which displays the result of the measurement, and a control means which is connected to the display means, the sample information input means and the reading means to store the identification mark for each measuring unit and the information on the sample fed to the measuring unit correlated to each other and causes the display means to display the result of the measurement on the sample held by a measuring unit in correlation with the identification mark for the measuring unit and the information on the sample fed to the measuring unit stored correlated to each other, since the identification mark for each measuring unit, the information on the sample fed to the measuring unit and the result of the measurement are managed in correlation with each other, an event that measurement is done in a wrong combination of a measuring unit and the sample liquid or the result of measurement for a wrong sample is displayed can be prevented.

In the method for accomplishing the second object of the present invention, since after attenuation in total internal reflection for the sample held in first one of the measuring units is detected, the support is moved relatively to the optical system and the photodetector to bring a second one of the measuring units to the predetermined position with respect to the optical system and the photodetector, attenuation in total internal reflection for the sample held in the second one of the measuring units is detected, and then the support is moved relatively to the optical system and the photodetector to bring the first one of the measuring units again to the predetermined position with respect to the optical system and the photodetector to detect again attenuation in total internal reflection for the sample held in the first one of the measuring units, measurement on one sample material can be carried out between intervals of measurement on another sample material, whereby lots of samples can be efficiently measured in a shorter time.

Investigation by these inventors has revealed that the problem, inherent to the prior art, that the measured values greatly fluctuate is due to the fact that the light beam is focused on the interface of the dielectric block and the film layer.

That is, when the light beam is focused on the interface, the spot size of the light beam on the interface becomes as very small as 10 $\mu$m to several hundreds of $\mu$m. Whereas there are fine irregularities on the surface of the film layer such as a metal film layer, and at the same time, when the specific material in the sample liquid is caused to react with the sensing material fixed to the surface of the film layer, reaction properties fluctuate by the position of the sensing material. Accordingly, when the light beam impinges upon the interface in a fine spot, the measured value is greatly affected by the fine irregularities on the surface of the film layer and the reaction properties which are largely vary according to the position of the light beam, which results in large fluctuation in the measured values.

On the basis of this recognition, in the measuring apparatuses utilizing the phenomenon of attenuation in total internal reflection for accomplishing the third object of the present invention, the optical system is arranged so that the light beam is not focused on the interface. With this arrangement, the spot size of the light beam on the interface becomes larger than in the conventional apparatuses. When the spot size of the light beam on the interface is large, the measured values come to correspond to the average irregularity on the surface of the film layer and the average reaction property, whereby fluctuation in the measured values can be suppressed.

BRIEF DESCRIPTION OF THE DRAWINGS

FIG. 7 is a plan view showing the surface plasmon resonance sensor in accordance with the fourth embodiment of the present invention, FIG. 12 is a side view showing a surface plasmon resonance sensor in accordance with an eighth embodiment of the present invention, FIG. 15 is a block diagram showing an electrical arrangement of the surface plasmon resonance sensor shown in FIG. 14, FIGS. 16A to 16C are views showing the relation between the angle of incidence of the light beam and the detected intensity of light, and the relation between the angle of incidence of a light beam and the differential value of the light intensity signal in the surface plasmon resonance sensor shown in FIG. 14, FIGS. 17A and 17B are graphs for illustrating an example of change in the measured values in the surface plasmon resonance sensor shown in FIG. 14, FIG. 18 is a plan view showing a surface plasmon resonance sensor in accordance with a tenth embodiment of the present invention, FIG. 19 is a side view partly cut away showing an important part of the surface plasmon resonance sensor shown in FIG. 18, FIG. 20 is a side view partly cut away showing an important part of a surface plasmon resonance sensor in accordance with an eleventh embodiment of the present invention, FIG. 21 is a perspective view partly cut away showing an important part of a surface plasmon resonance sensor in accordance with a twelfth embodiment of the present invention, FIG. 24 is a plan view showing a part of the surface plasmon resonance sensor shown in FIG. 22, FIG. 26 is a perspective view showing an example of a measuring unit train employed in the surface plasmon resonance sensor of the present invention, FIG. 31 is a perspective view showing an important part of a surface plasmon resonance sensor in accordance with a sixteenth embodiment of the present invention, FIG. 35 is a graph showing an example of result of measurement by a surface plasmon resonance measuring method of the present invention.

PREFERRED EMBODIMENTS OF THE INVENTION

Figure 1:
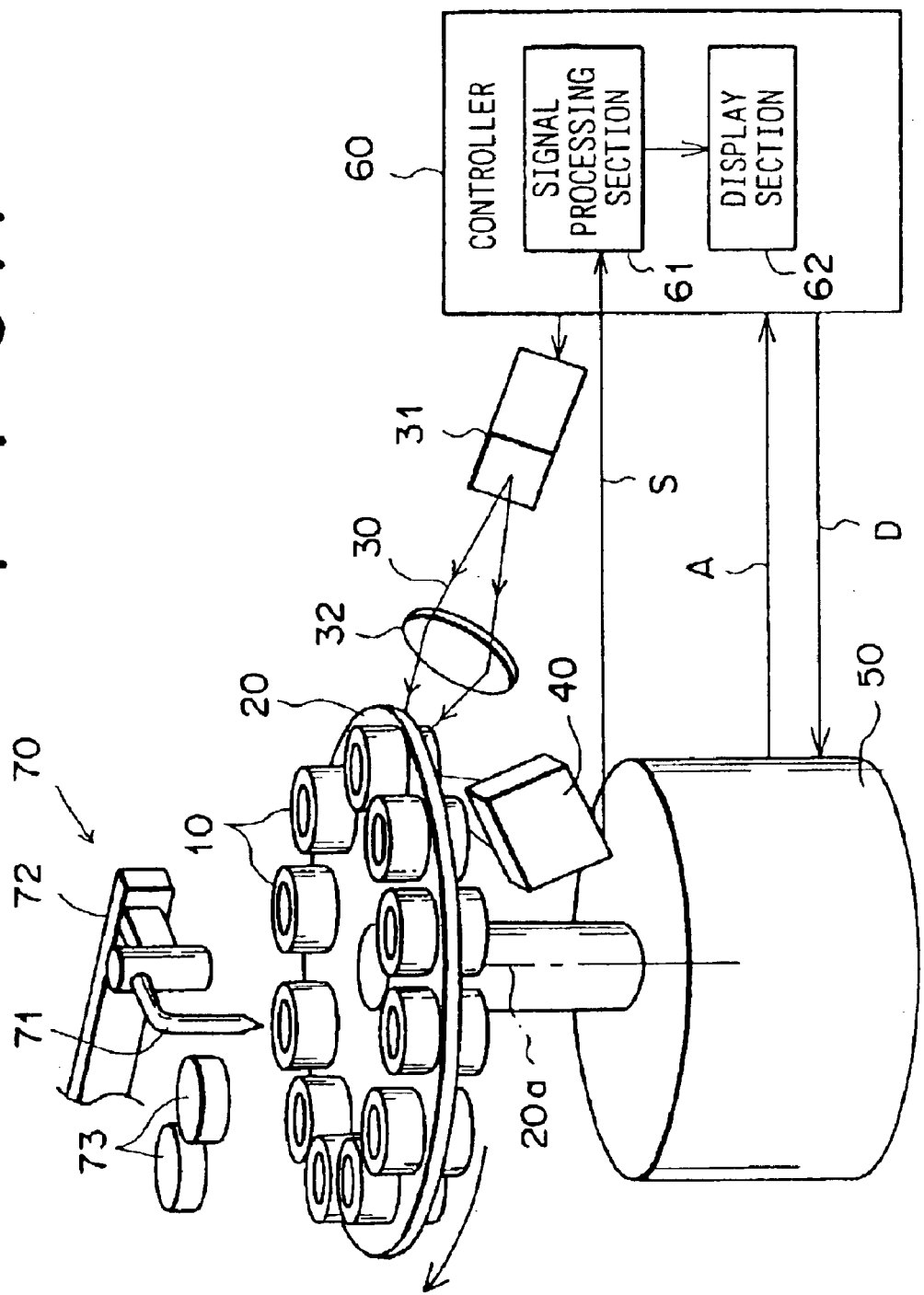
FIG. 1 is a perspective view showing a surface plasmon resonance sensor in accordance with a first embodiment of the present invention.

Embodiments of the present invention will be described in detail with reference to the drawings, hereinbelow. FIG. 1 shows the overall arrangement of a surface plasmon resonance sensor in accordance with a first embodiment of the present invention, and FIG. 2 is a side view showing an important part of the surface plasmon resonance sensor.

As shown in FIG. 1, the surface plasmon resonance sensor comprises a turn table 20 on which a plurality of measuring units 10 are supported, a laser 31 such as a semiconductor laser which emits a measuring light beam (laser beam) 30, a condenser lens 32 which forms an incident optical system, a photodetector 40, a drive means 50 which intermittently rotates the turn table 20, a controller 60 which controls the drive means 50 and at the same time receives output signal S of the photodetector 40 to execute processing described later, and an automatic sample supply mechanism 70.

Figure 2:
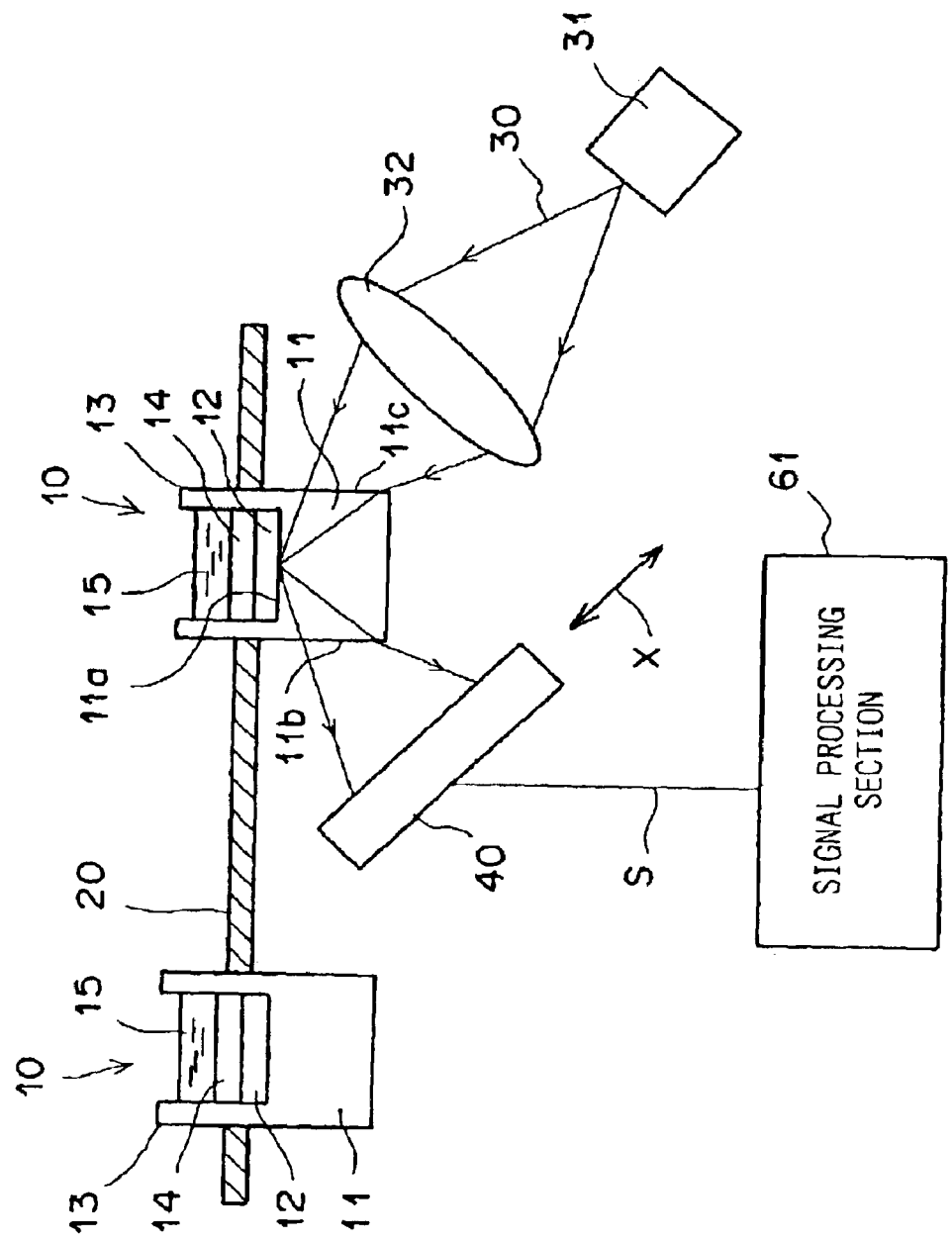
FIG. 2 is a side view partly cut away showing an important part of the surface plasmon resonance sensor shown in FIG. 1.

As shown in FIG. 2, each of the measuring units 10 comprises a transparent dielectric block 11 which is, for instance, rectangular in shape, a metal film 12 such as of gold, silver, cupper, aluminum or the like which is formed on the upper face of the block 11, and a sample holder frame 13 which is a tubular member defining above the metal film 12 a space having closed side walls. In the sample holder frame 13 is stored, for instance, a sample liquid 15 in the manner to be described later.

The measuring unit 10 is formed, for instance, by integrally forming the dielectric block 11 and the sample holder frame 13 by injection molding of transparent resin and is replaceable. In this particular embodiment, the measuring units 10 are removably held in through holes formed in the turn table 20. Further, in this particular embodiment, a sensing medium 14 is fixed on the metal film 12. The sensing medium 14 will be described later.

The turn table 20 is arranged so that a plurality of (eleven in this particular embodiment) measuring units 10 are supported on a circle about its axis of rotation 20a at regular intervals. The drive means 50 comprises a stepping motor or the like and intermittently rotates the turn table 20 by an angle equal to the angular space between the units 10.

As shown in FIG. 2, the condenser lens 32 condenses the light beam 30 and caused to enter the dielectric block 11 in the form of a convergent light beam so that various angles of incidence of the light beam 30 to the interface 11a of the dielectric block 11 and the metal film 12 can be obtained. The range of the angles of incidence is set to include a range in which the total internal reflection condition of the light beam 30 is satisfied at the interface 11a and a surface plasmon resonance can take place.

The light beam 30 impinges upon the interface 11a in the form of p-polarized light. This can be realized by suitably positioning the laser 31 or by controlling the polarization direction of the light beam 30 with a wavelength plate, a polarizing plate or the like.

The photodetector 40 comprises a line sensor having a number of photodetector elements arranged in a row in the direction arrow X in FIG. 2.

The controller 60 receives an address signal A representing the position of the drive means 50 and outputs a drive signal D for driving the drive means 50 on the basis of a predetermined sequence. Further, the controller 60 is provided with a signal processing section 61 which receives an output signal S from the photodetector 40 and a display section 62 which receives an output of the signal processing section 61.

The automatic sample supply mechanism 70 comprises a pipette 71 which sucks a predetermined amount of sample liquid and a pipette drive means 72 which moves the pipette 71. The automatic sample supply mechanism 70 causes the pipette 72 to suck the sample in a sample container 73 held in a predetermined position and moves the pipette 71 above the sample holder frame 13 of a measuring unit 10 in a predetermined position, and causes the pipette 71 to spot the sample liquid in the sample holder frame 13.

Operation of the surface plasmon resonance sensor will be described hereinbelow. The turn table 20 is intermittently rotated by the drive means 50. When the turn table 20 is stopped, sample liquid 15 is supplied to the sample holder frame 13 of the measuring unit 10 in the predetermined position by the automatic sample supply mechanism 70.

When a measuring unit 10 the sample holder frame 13 of which contains therein the sample liquid 15 is stopped in a predetermined measuring position (the position of the right side measuring unit 10 in FIG. 2), the laser 31 is driven under the control of the controller 60 and the light beam 30 emitted from the laser 31 impinges upon the interface 11a between the dielectric block 11 and the metal film 12 in the form of convergent light. The light beam 30 is reflected in total internal reflection at the interface 11a and is detected by the photodetector 40.

Since the light beam 30 impinges upon the interface 11a in the form of convergent light, the light beam 30 includes components which impinge upon the interface at various angles θ. The angles θ of incidence is not smaller than the angle of total internal reflection. Accordingly, the light beam 30 is reflected in total internal reflection at the interface 11a, and the reflected light beam 30 at the interface 11a includes components reflected at various reflecting angles.

Figure 3:
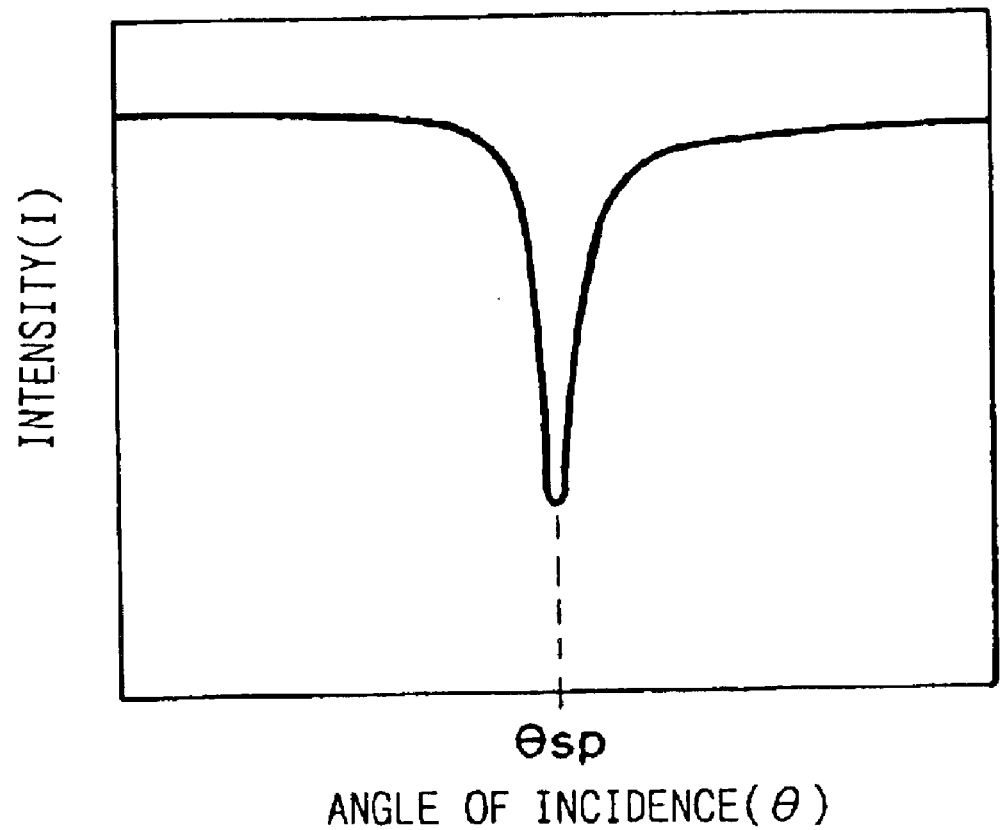
FIG. 3 is a graph showing the relation between the angle of incidence of the light beam and the output of the photodetector in the surface plasmon resonance sensor.

When the light beam 30 is reflected in total internal reflection at the interface 11a, evanescent waves ooze out from the interface 11a toward the metal film 12. The component of the light beam 30 which impinges upon the interface at a specified angle θsp resonates with the surface plasmon excited on the surface of the metal film 12 by the evanescent waves and accordingly, the intensity I of the component of the light beam 30 reflected in total internal reflection at the interface 11a sharply drops. FIG. 3 is a graph showing the relation between the angle of incidence θ of the light beam 30 and the intensity I of the reflected light.

By detecting the amount of reflected light received by each photodetector element on the basis of the output signal S of the photodetector 40, the position of the photodetector element which detects the dark line can be determined and the angle θsp of incidence at which the intensity I of the light beam 30 reflected in total internal reflection at the interface 11a (angle θsp of total internal reflection attenuation) sharply drops can be determined. Accordingly by referring to a standard curve which represents the relation between the intensity I of the reflected light and the angle θ of incidence of the light beam 30, a particular material in the sample 15 can be quantitatively analyzed. The signal processing section 61 of the controller 60 quantitatively analyzes the particular material in the sample 15 on the basis of this fact and the result of the analysis is displayed by the display section 62.

When each sample 15 is subjected to measurement only once, the measuring units 10 may be manually or automatically removed from the turn table 20. Whereas when each sample 15 is subjected to measurement a plurality of times, the measuring units 10 may be left on the turn table 20 so that the measuring unit 20 is brought to the measuring position again when the turn table 20 makes another rotation.

As described above, in the surface plasmon resonance sensor of this embodiment, since a plurality of measuring units 10 are held on the turn table 20 and the turn table 20 is intermittently rotated so that the measuring units 10 are brought to the measuring position in sequence, a plurality of samples 15 can be measured at a high efficiency whereby the time required to measure each sample can be shortened.

Further, since, in this particular embodiment, the automatic sample supply mechanism 70 is provided, the time required to supply samples to the measuring units 10 also can be shortened, whereby the time required to measure each sample can be further shortened.

Further, since, in this particular embodiment, the dielectric block 11, the metal film layer 12 and the sample holder frame 13 are integrated into a measuring unit 10, new samples 15 can be measured in sequence by changing measuring units 10 after the measurement with a measuring unit 10, whereby the time required to measure a lot of samples can be further shortened.

The sensing medium 14 fixed on the surface of the metal film 12 is selectively linked to a specific material in the sample 15. As such a combination of the sensing medium 14 and the specific material in the sample 15, for instance, combinations of antigen and antibody are known. In such a case, antigen-antibody reaction can be detected on the basis of the angle θsp of total internal reflection attenuation.

That is, the refractive index of the sensing medium 14 changes with progress of bonding reaction between the specific material in the sample and the sensing medium 14 so that the curve shown in FIG. 3 moves right and left. Accordingly, the state of antigen-antibody reaction can be detected through the total reflection attenuation angle θsp. In this case, both the sample 15 and the sensing medium 14 can be analyzed.

Figure 4:
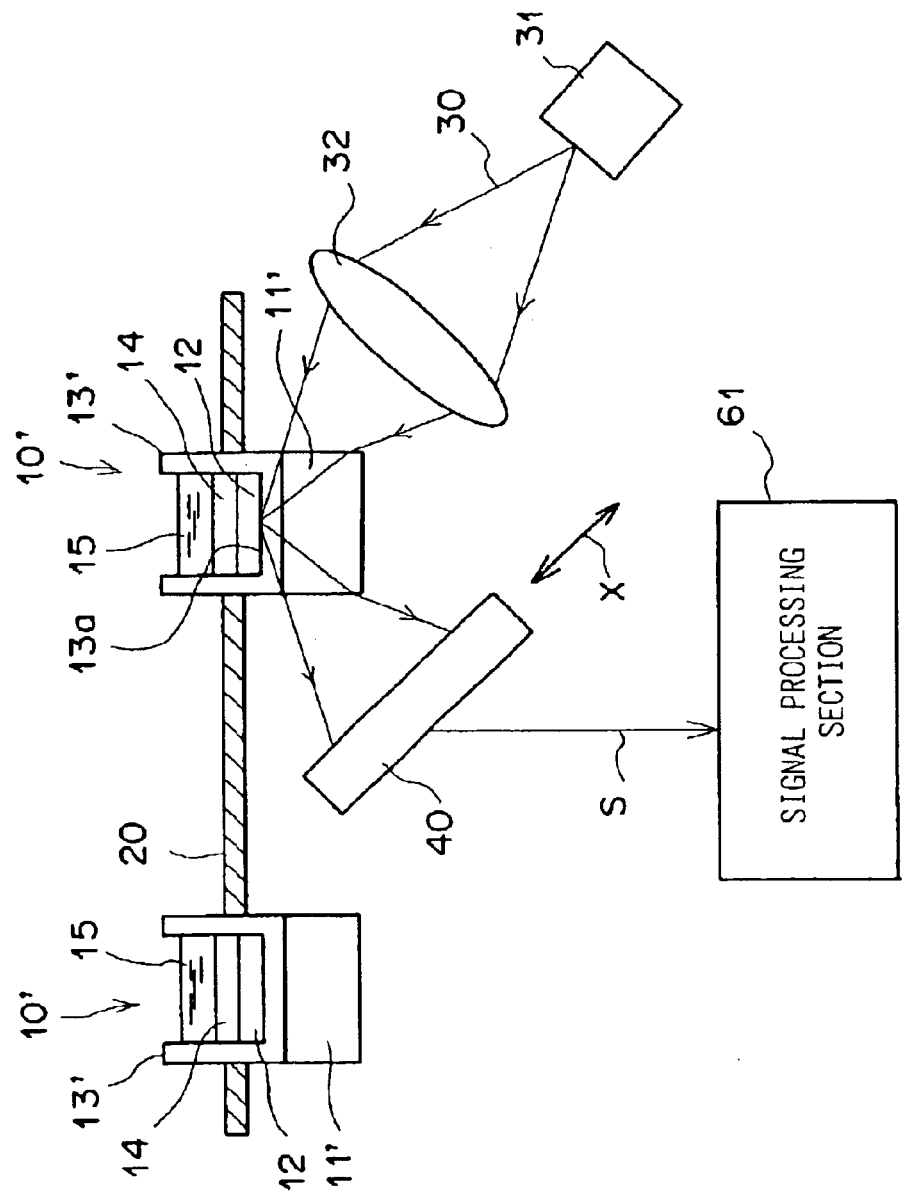
FIG. 4 is a side view partly cut away showing an important part of a surface plasmon resonance sensor in accordance with a second embodiment of the present invention.

A surface plasmon resonance sensor in accordance with a second embodiment of the present invention will be described with reference to FIG. 4, hereinbelow. FIG. 4 is a side view partly cut away showing an important part of a surface plasmon resonance sensor in accordance with a second embodiment of the present invention. In FIG. 4, elements analogous to those shown in FIG. 2 are given the same reference numerals and will not be described here. (and so forth)

The surface plasmon resonance sensor shown in FIG. 4 differs from that shown in FIG. 2 in the structure of the measuring unit. That is, the measuring unit 10' in this embodiment comprises a dielectric block 11' fixed to the turntable 20, and a sample holder frame 13' and a metal film layer 12 integrated with each other. The sample holder frame 13' is in the form of a bottomed tubular member formed of transparent dielectric material and the metal film layer 12 is fixed on the bottom of the sample holder frame 13'. Thus, the sample holder frame 13' and the metal film layer 12 are integrated to form a measuring chip.

The measuring chip can be removed from the dielectric block 11' so that the measuring chip can be replaced by another. It is preferred that refractive index matching fluid is provided between the sample holder frame 13' and the dielectric block 11'. In this case, the sample holder frame 13' is integrated with the dielectric block 11' to form a single dielectric block and the light beam 30 is caused to impinge upon the interface 13a between the sample holder frame 13' and the metal film layer 12.

Also in this embodiment, by removing the measuring chip, bearing thereon the sample which has been measured, from the dielectric block and replacing with another, new samples 15 can be measured in sequence, whereby the time required to measure a lot of samples can be further shortened.

A surface plasmon resonance sensor in accordance with a third embodiment of the present invention will be described with reference to FIG. 5, hereinbelow. Figure is a side view partly cut away showing an important part of the surface plasmon resonance sensor in accordance with the third embodiment of the present invention. The surface plasmon resonance sensor shown in FIG. 5 differs from that shown in FIG. 2 in the manner of projecting the light beam 30 onto the interface 11a of the dielectric block 11 and the metal film layer 12. That is, in this embodiment, the condenser lens 32 is arranged so that the light beam 30 (in the form of a conical beam) impinges upon the interface 11a in a defocused state. The light beam 30 is 500 $\mu$m×500 $\mu$m in spot size on the interface 11a, whereas, in the conventional system where the light beam is focused on the interface 11a, the light beam 30 is 100 $\mu$m×100 $\mu$m in spot size on the interface 11a.

Since the turntable 20 is mechanically driven by the drive means 50, fluctuation in position of the turntable 20 is inevitable. Fluctuation in position of the turntable 20 results in fluctuation in position of the measuring unit 10 with respect to the light beam 30 emanating from the condenser lens 32, which results in an error in measuring attenuation in total internal reflection. For example, an error in detecting the position of the dark line representing attenuation total internal reflection can occur.

When the light beam 30 impinges upon the interface 11a in a defocused state, errors in detecting the state of surface plasmon resonance (in detecting the position of the aforesaid dark line) are averaged, whereby the measuring accuracy is enhanced.

When the spot size is large as in this embodiment, the measured value reflects the average of the fine irregularities on the surface of the metal film layer 12 and the reaction properties, whereby fluctuation of the measured values can be suppressed.

When the light beam 30 is caused to impinge upon the interface 11a in a defocused state, it is preferred that the beam diameter of the light beam 30 as measured on the interface 11a in the direction of movement of the turntable 30 be at least ten times the mechanical positioning accuracy of the turntable 30.

Figure 6:
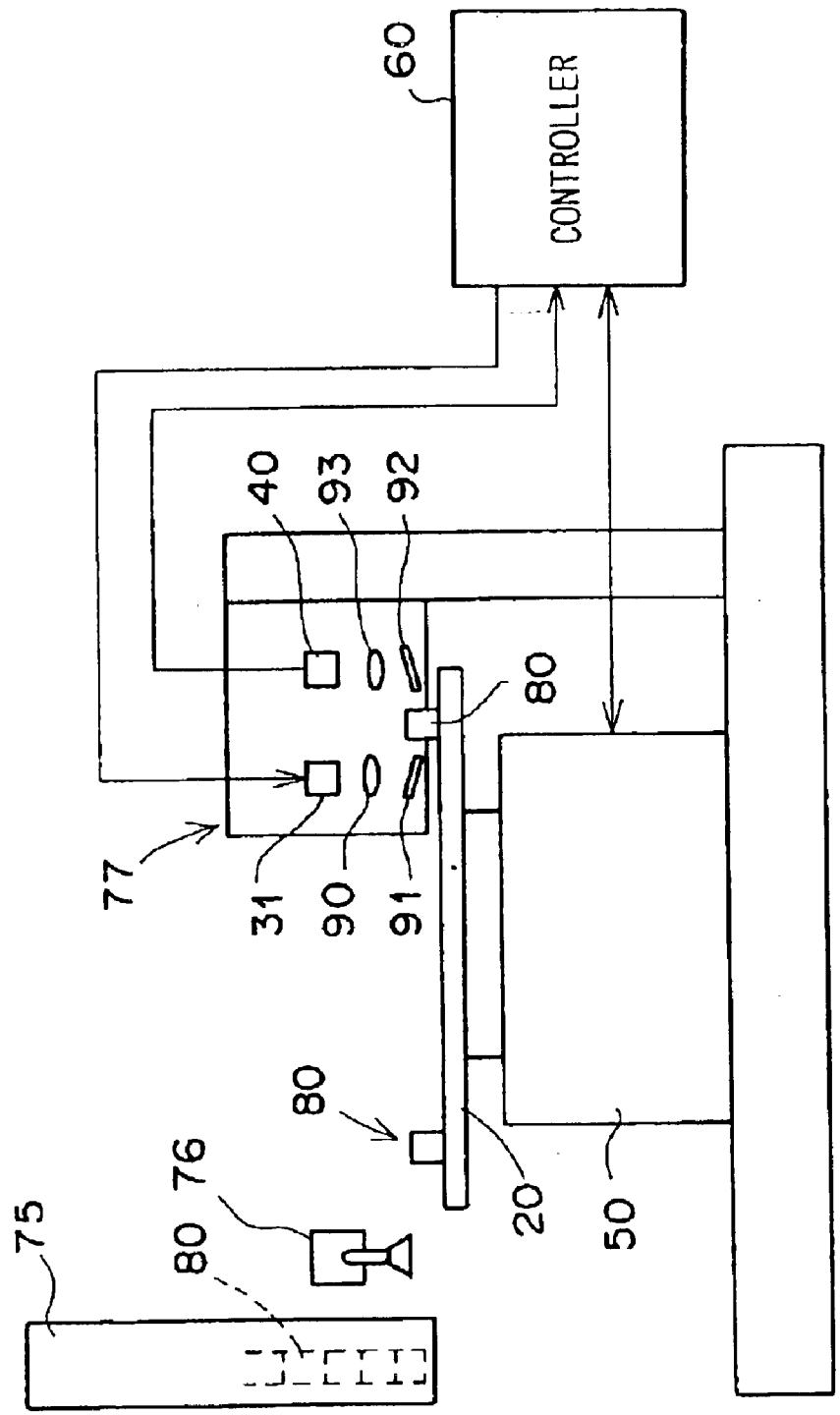
FIG. 6 is a side view showing a surface plasmon resonance sensor in accordance with a fourth embodiment of the present invention.
Figure 8:
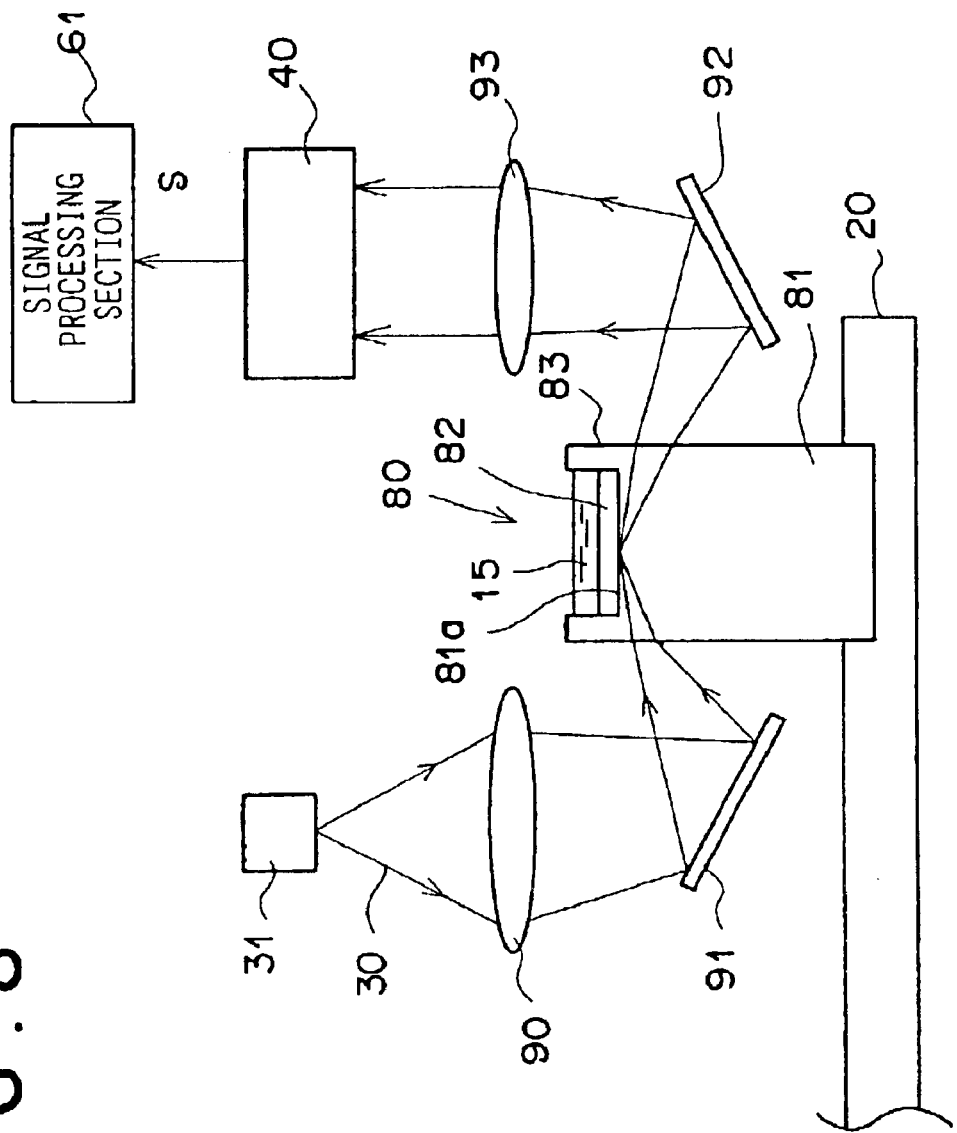
FIG. 8 is a side view partly cut away showing an important part of the surface plasmon resonance sensor in accordance with the fourth embodiment of the present invention.

A fourth embodiment of the present invention will be described with reference to FIGS. 6, 7 and 8. FIGS. 6 and 7 respectively show a side view and a plan view of a surface plasmon resonance sensor in accordance with the fourth embodiment of the present invention, and FIG. 8 is a side view showing an important of the same.

As shown in FIGS. 6 and 7, in the surface plasmon resonance sensor of this embodiment, four measuring units 80 are supported on a turntable 20 at regular intervals of 90°, and the turntable 20 is intermittently rotated 90° by 90° in the direction of arrow R. Thus, each measuring unit 80 is brought to four positions, a measuring unit supply position P1, a sample supply position P2, a measuring position P3 and a measuring unit discharge position P4, in sequence. The measuring unit 80 will be described in detail later.

When a measuring unit support portion is stopped in the measuring unit supply position P1, a measuring chip supply means 76 takes out a measuring unit 80 from a cassette 75 in which a plurality of measuring units 80 are contained and supplies it to the measuring unit supply portion. The chip supply means 76 may be of a known structure comprising a suction cup and a mechanism for moving the suction cup. For example, the suction cup is arranged to take out the measuring units 80 one by one through a take-out port formed in the bottom of the cassette 75 holding the measuring unit 80 under suction force and the mechanism moves the suction cup together with the measuring unit 80 to the measuring unit support portion in the measuring unit supply position P1.

To the measuring unit stopped in the sample supply position P2, a sample is supplied by an automatic sample supply mechanism 70.

The sample held by the measuring unit 80 stopped in the measuring position P3 is analyzed by a surface plasmon resonance sensing means 77. The analysis will be described in detail later with reference to FIG. 8.

The measuring unit 80 stopped in the measuring unit discharge position P4 is discharged from the turntable 20 by a measuring chip discharge means 78. The measuring unit support position thus removed with the measuring unit is brought to the measuring unit supply position P1 as the turntable 20 is subsequently turned by 90° and supplied with another measuring unit 80. Thereafter, the aforesaid steps are repeated each time the turntable 20 is turned by 90°.

Analysis by the surface plasmon resonance sensing means 77 will be described with reference to FIG. 8, hereinbelow. The measuring unit 80 employed in this embodiment comprises a transparent electric block 81, a metal film layer 82 and a sample holder frame 83 which are formed integrally with each other as in the measuring unit 10 employed in the first embodiment.

A laser beam 30 emitted from the laser 31 is condensed by a condenser lens 90 and is reflected by a mirror 91 to impinge upon the interface 81a of the dielectric block 81 and the metal film layer 82. The light beam 30 reflected in total internal reflection at the interface 81a is reflected by a mirror 92 to impinge upon the photodetector 40 after collimated by a collimator lens 93. The output signal S of the photodetector 40 is input into the signal processing section 61 of the controller 60 (FIG. 6) and the sample material is analyzed on the basis of the output signal S in the same manner as that described above in conjunction with the first embodiment.

As can be understood from the description above, in this embodiment, since a plurality of measuring chips (measuring units) 80 are contained in the measuring chip cassette 75, and the measuring chips 80 are taken out from the measuring chip cassette 75 one by one and mounted on the turntable 20 by the chip supply means 76, supply of the measuring chips can be effectively carried out, whereby lots of samples 15 can be measured in a shorter time.

This arrangement can be applied to not only the measuring units 80 each of which comprises a transparent dielectric block 81, a metal film layer 82 and a sample holder frame 83 integrally formed with each other but also measuring units 10' in which a metal film layer 12 and a sample holder frame 13' are formed to be exchangeable with respect to the dielectric block 11' as shown in FIG. 4 by integrating the metal film layer 12 and the sample holder frame 13' into a measuring chip and containing a plurality of measuring chips in a cassette, whereby the measuring chips can be automatically supplied and supply of the measuring chips can be effectively carried out.

Though, in the embodiments described above, a turntable 20 is employed as the support for supporting the measuring units, the support need not be limited to such a turntable. For example, the support may be one which is linearly moved back and forth with a plurality of measuring units supported thereon to bring the measuring units to the measuring position one by one.

In this case, when each sample is subjected to measurement a plurality of times, a plurality of measuring means each comprising an optical system for projecting a light beam onto the measuring unit and a photodetector are provided along the support so that each measuring unit is brought to one of the measuring means as the support is moved. Otherwise, each sample can be subjected to measurement a plurality of times by providing a single measuring means along the support and reversing the support after a certain number of measuring units are subjected to measurement by moving the support in the regular direction.

Also the support in the form of the aforesaid turntable 20 may be rotated back and forth to subject each measuring unit to measurement. Further it is possible to provide a plurality of measuring means along the turntable 20 so that each measuring unit is subjected to measurement a plurality of times during one rotation of the turntable 20.

Figure 9:
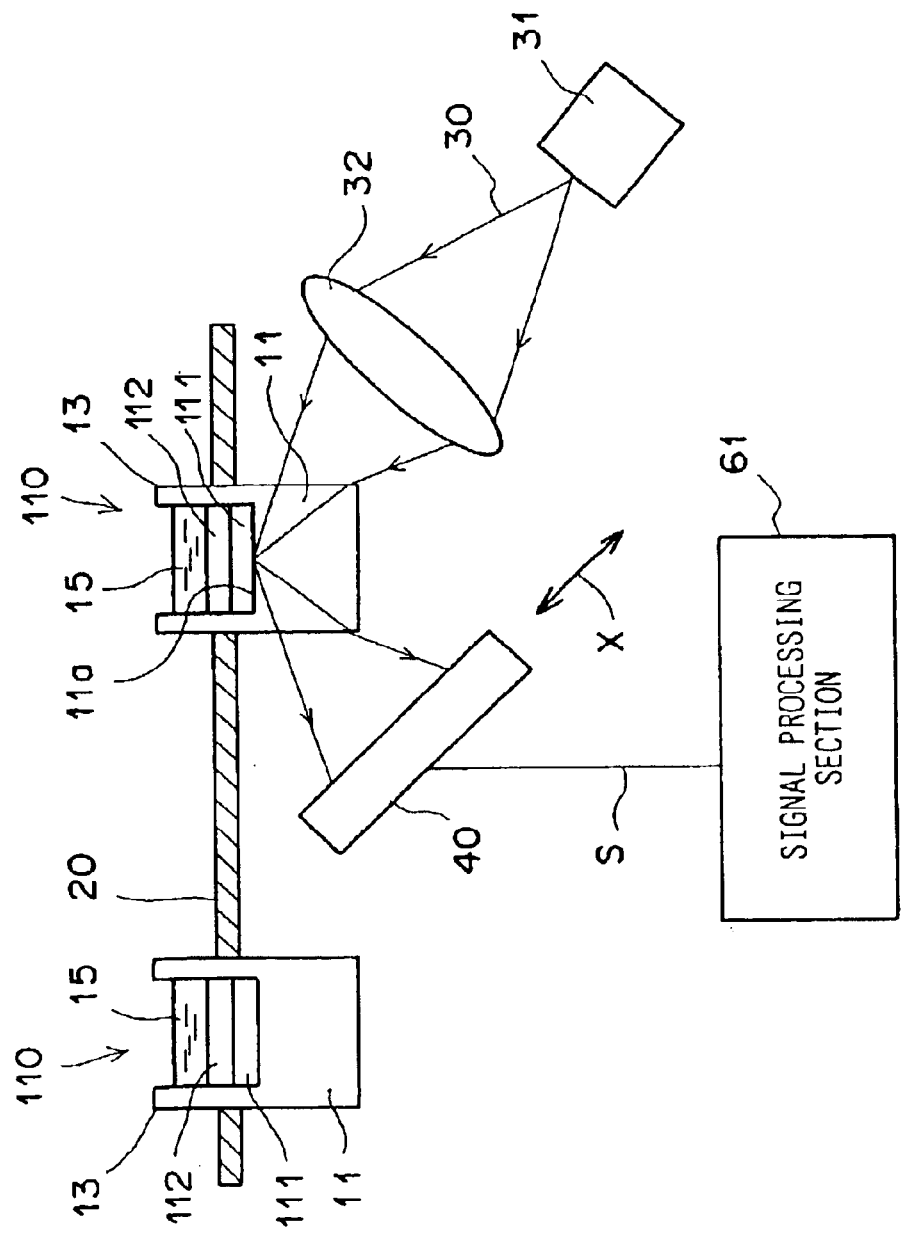
FIG. 9 is a side view partly cut away showing an important part of a leaky mode sensor in accordance with a fifth embodiment of the present invention.

A fifth embodiment of the present invention will be described, hereinbelow. FIG. 9 is a side view showing a measuring apparatus utilizing the phenomenon of attenuation in total internal reflection in accordance with the fifth embodiment of the present invention. In FIG. 9, elements analogous to those shown in FIG. 2 are given the same reference numerals.

The measuring apparatus of this embodiment is a leaky mode sensor and measuring units 110 in the form of a measuring chip are employed in this embodiment. Each measuring unit 110 comprises a dielectric block 11, a clad layer 111 formed on one surface (the upper surface as seen in FIG. 9) and an optical waveguide layer 112 formed on the clad layer 111.

The dielectric block 11 is formed of, for instance, synthetic resin or optical glass such as BK7. The clad layer 111 is formed of dielectric material lower than the dielectric block 1 in refractive index or metal such as gold. The optical wave guide layer 112 is formed of dielectric material such as PMMA which is higher than the clad layer 111 in refractive index. The thickness of the clad layer 111 is 36.5 nm when it is formed of gold film, and the thickness of the optical waveguide layer 112 is about 700 nm when it is formed of PMMA.

In the leaky mode sensor, when the light beam 30 emitted from the laser 31 is caused to impinge upon the clad layer 111 at an angle not smaller than an angle of total internal reflection through the dielectric block 11, the light beam 30 is reflected in total internal reflection at the interface 11a of the dielectric block 11 and the clad layer 111, and only light having a particular wave number and impinging upon the waveguide layer 112 at a particular angle of incidence comes to propagate through the optical waveguide layer 112 in a waveguide mode after passing through the clad layer 111. When the waveguide mode is thus excited, almost all the incident light is taken in the optical waveguide layer 112 and accordingly, the intensity of light reflected in total internal reflection at the interface 11a of the dielectric block 11 and the clad layer 111 sharply drops. That is, attenuation in total internal reflection occurs.

Since the wave number of light to be propagated through the optical waveguide layer 112 in a waveguide mode depends upon the refractive index of the sample 15 on the optical waveguide layer 112, the refractive index and/or the properties of the sample 15 related to the refractive index can be detected on the basis of the angle of incidence at which the attenuation in total internal reflection occurs. A signal processing section 61 quantitatively analyzes the particular material in the sample 15 on the basis of this fact and the result of the analysis is displayed by the display section (not shown).

Also in the leaky mode sensor of this embodiment, since a plurality of measuring units 110 are held on the turn table 20 and the turn table 20 is intermittently rotated so that the measuring units 110 are brought to the measuring position in sequence, a plurality of samples 15 can be measured at a high efficiency whereby the time required to measure each sample can be shortened.

Further, since, also in this particular embodiment, the dielectric block 11, the clad layer 111 and the optical waveguide layer 112 are integrated into a measuring unit 110, new samples 15 can be measured in sequence by changing measuring units 110 after the measurement with a measuring unit 110, whereby the time required to measure a lot of samples can be further shortened.

Figure 10:
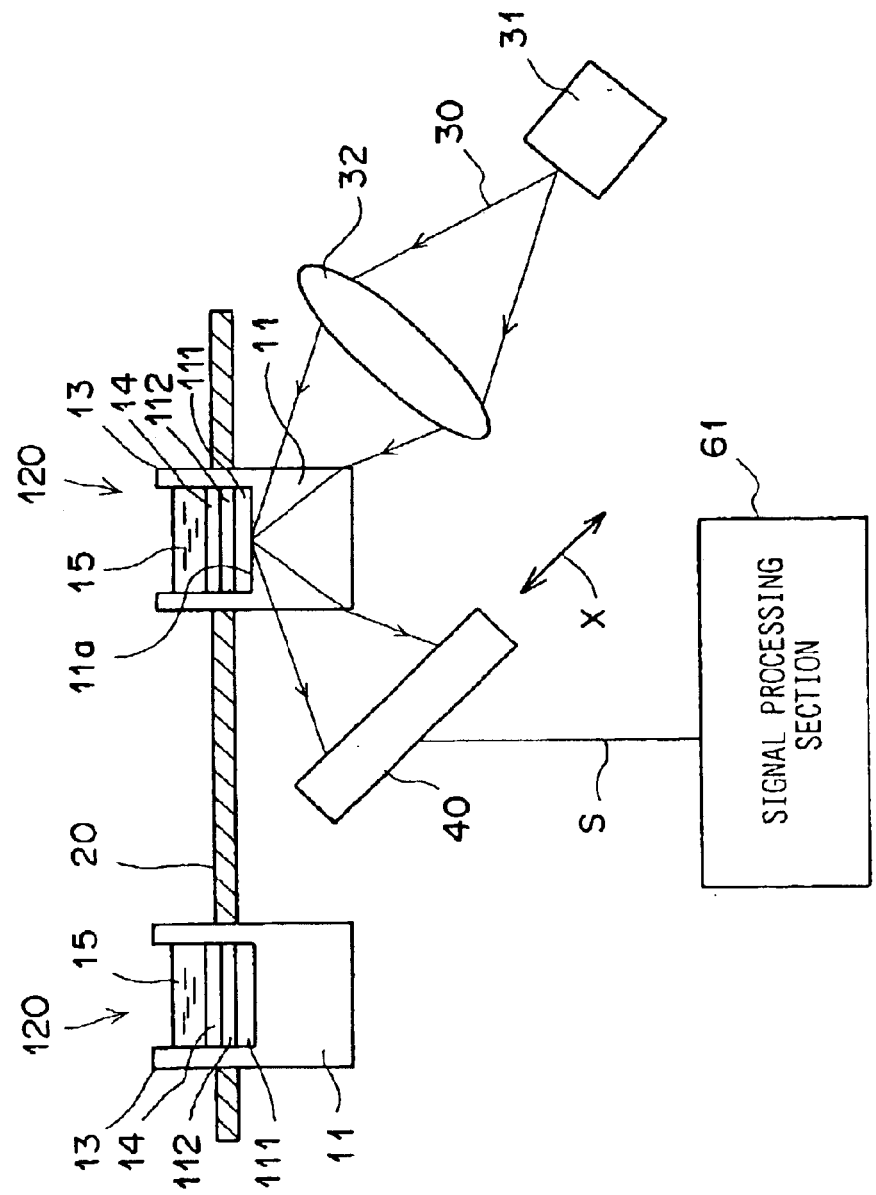
FIG. 10 is a side view partly cut away showing an important part of a leaky mode sensor in accordance with a sixth embodiment of the present invention.

A sixth embodiment of the present invention will be described, hereinbelow. FIG. 10 is a side view showing an important part of a measuring apparatus utilizing the phenomenon of attenuation in total internal reflection in accordance with the sixth embodiment of the present invention. In FIG. 10, elements analogous to those shown in FIG. 9 are given the same reference numerals.

The measuring apparatus of this embodiment is also a leaky mode sensor and measuring units 120 in the form of a measuring chip are employed in this embodiment. Each measuring unit 120 comprises a dielectric block 11, a clad layer 111 formed on one surface (the upper surface as seen in FIG. 9) of the dielectric block 11, an optical waveguide layer 112 formed on the clad layer 111 and a sensing medium 14 fixed on the optical waveguide layer 112. The apparatus of this embodiment basically differs from that shown in FIG. 9 only in that the sensing material 14 is fixed on the optical waveguide layer 112.

The sensing medium 14 fixed on the surface of the metal film 12 is selectively linked to a specific material in the sample 15 as that of the apparatus shown in FIG. 2. As such a combination of the sensing medium 14 and the specific material in the sample 15, for instance, combinations of antigen and antibody are known. In such a case, antigen-antibody reaction can be detected on the basis of the angle θsp of total internal reflection attenuation.

That is, though the relation between the angle of incidence θ of the light beam 30 and the intensity I of the reflected light is basically as shown in FIG. 3, the effective refractive index of the sensing medium 14 changes with progress of bonding reaction between the specific material in the sample and the sensing medium 14 so that the curve shown in FIG. 3 moves right and left. Accordingly, the state of antigen-antibody reaction can be detected through the total reflection attenuation angle θsp.

Figure 11:
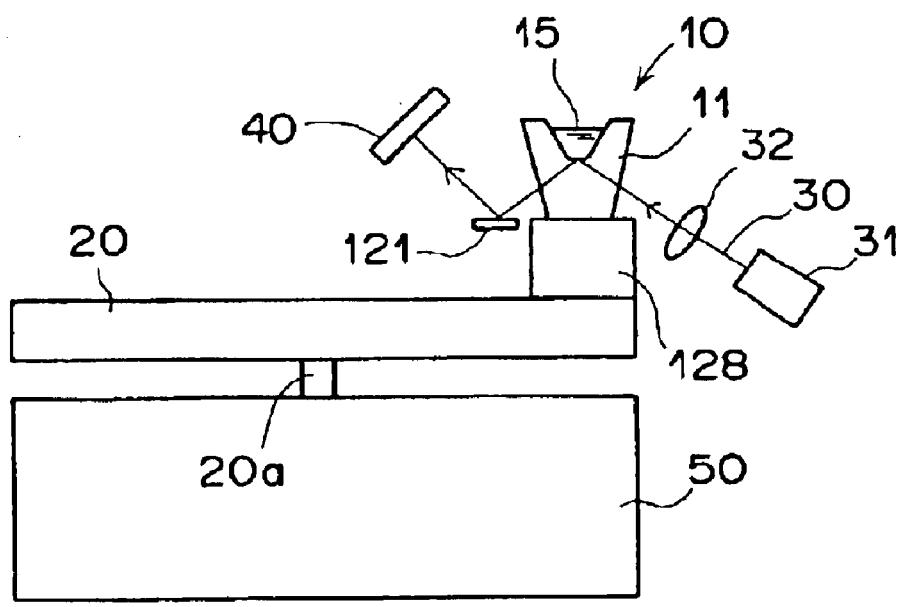
FIG. 11 is a side view showing a surface plasmon resonance sensor in accordance with a seventh embodiment of the present invention.

A seventh embodiment of the present invention will be described, hereinbelow. FIG. 11 is a side view showing an important part of a measuring apparatus utilizing the phenomenon of attenuation in total internal reflection in accordance with the seventh embodiment of the present invention. In FIG. 11, elements analogous to those shown in FIGS. 1 and 2 are given the same reference numerals.

The measuring apparatus of this embodiment is a surface plasmon resonance sensor and is arranged so that a measuring unit 10 containing therein a sample 15 is held on a measuring unit holding portion 128. The measuring unit 10 is substantially the same as that shown in FIGS. 1 and 2 except that the shape of the dielectric block 11 somewhat differs from that of the dielectric block shown in FIGS. 1 and 2.

In the apparatus of this embodiment, though the light beam 30 is caused to impinge upon the interface 11a of the dielectric block 11 and the metal film layer 12 from below as in the embodiment shown in FIG. 2, a mirror 121 which reflects upward the light beam 30 reflected in total internal reflection at the interface 11a is provided and the light beam 30 reflected by the mirror 121 to travel upward is detected by a photodetector 40 which is disposed above the mirror 121 with its light receiving surface directed downward.

When the photodetector 40 is positioned above the turntable 20 by providing a mirror 121 which reflects upward the light beam 30, it becomes unnecessary to take into account interference between the rotating turntable 20 and the photodetector 40, and the freedom in layout of the photodetector 40 as well as other elements which are to be disposed near the support can be increased.

An eighth embodiment of the present invention will be described, hereinbelow. FIG. 12 is a side view showing an important part of a measuring apparatus utilizing the phenomenon of attenuation in total internal reflection in accordance with the eighth embodiment of the present invention. The measuring apparatus of this embodiment is also a surface plasmon resonance sensor and differs from that shown in FIG. 11 in that a mirror 122 which reflects upward the light beam 30 emitted from the laser 31 and the laser 31 is disposed above the mirror 122.

By thus disposing the photodetector 40 and the laser 31 above the turntable 20, it becomes unnecessary to take into account interference between the turntable 20 and the photodetector 40 as well as the laser 31, and the freedom in layout of the photodetector 40 and the laser 31 as well as other elements which are to be disposed near the turntable 20 can be increased.

The layout of the photodetector 40 and the laser 31 employed in the seventh and eighth embodiments of the present invention need not be limited to the surface plasmon resonance sensor but can be employed also in the leaky mode sensor shown in FIG. 9 or 10.

Further, the layout of the photodetector 40 and the laser 31 employed in the seventh and eighth embodiments of the present invention need not be limited to the surface plasmon resonance sensor or the leaky mode sensor where a turntable is employed as the support but can be employed also in the surface plasmon resonance sensor or the leaky mode sensor where a support is linearly moved back and forth.

Figure 13:
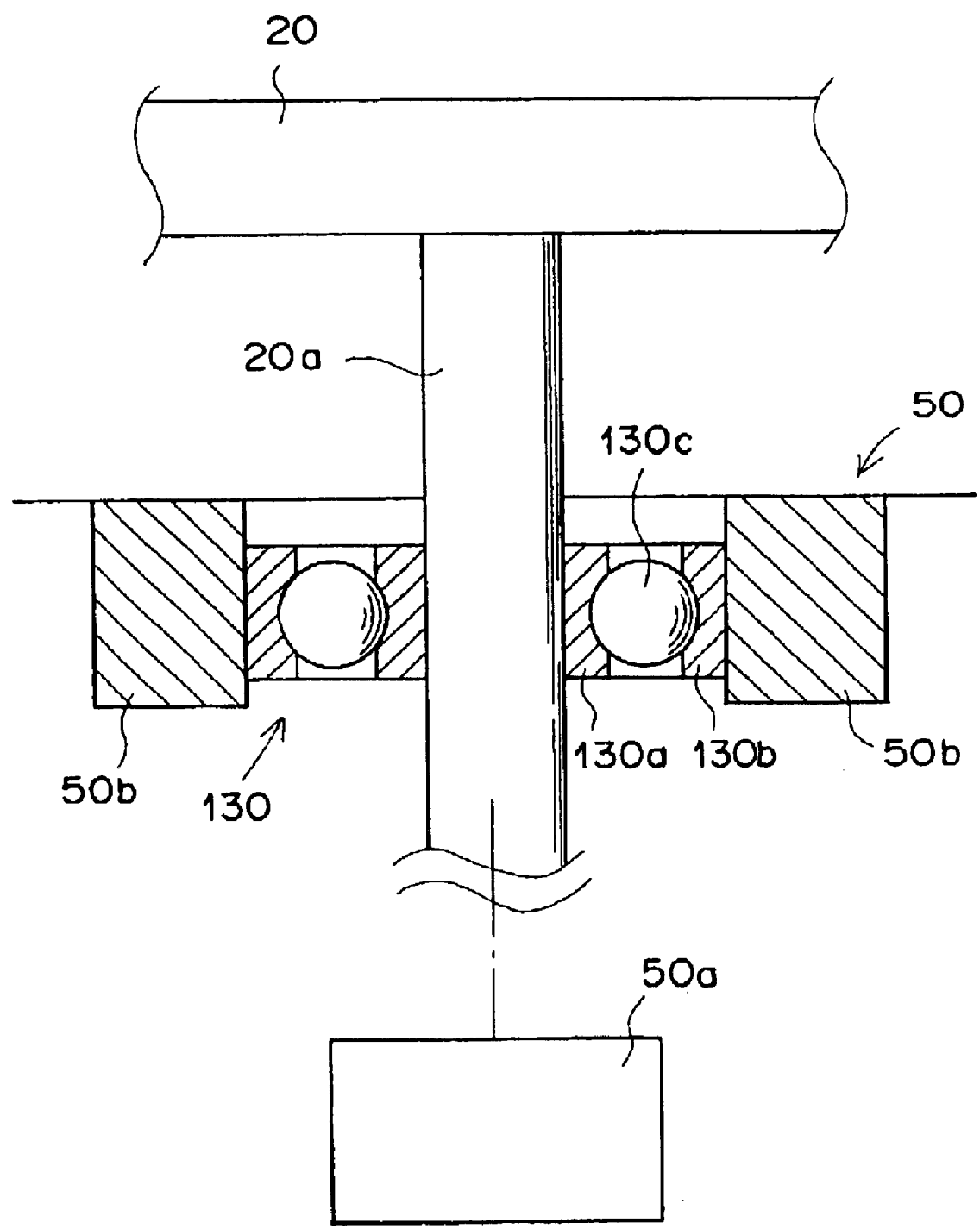
FIG. 13 is a side view partly cut away showing an example of the structure of the drive shaft portion of a turntable which can be employed in the surface plasmon resonance sensor of the present invention.

FIG. 13 shows in more detail the turntable 20 shown in FIG. 1. That is, the turntable 20 is operatively connected to a motor 50a of a support drive means 50 such as a stepping motor by way of a rotating shaft 20a and is driven by the motor 50a. The rotating shaft 20a is supported for rotation on a bearing portion 50b of the support drive means 50 by way of one or more roller bearing 130.

The roller bearing 130 comprises an inner ring 130a which is fitted on the rotating shaft 20a and fixed thereto, an outer ring 130b which is fitted in the bearing portion 50b of the support drive means 50 and fixed thereto, and rolling members 130c such as rollers or balls which roll between the inner and outer rings 130a and 130b. When the rotating shaft 20 is rotated by the motor 50a, the inner ring 130a is rotated integrally with the rotating shaft 20a and the rolling members 130c make revolution around the inner ring 130a while rotating on the inner ring 130a.

Accordingly, when the rolling members 130 are not good in roundness and/or the surface of the inner ring 130a or the outer ring 130b is rough, the position in a diametrical direction or the inclination of the inner ring 130a (that is, of the rotating shaft 20a) varies according to the revolution position of the rolling members 130c, which can result in fluctuation in the axis of rotation of the turntable 20 and/or inclination of the turntable 20 from the horizon. Such a behavior of the turntable 20 changes the position of the measuring units 10 thereon and the incident angle of the light beam 30 to the interface 11a fluctuates, whereby error in measuring the samples 15 is generated.

In order to prevent production of the measuring error, rotation of the turntable 20 is controlled in the following manner. Here it is assumed that sixteen measuring units 10 are supported on the turntable 20 at regular intervals of 22.5°. The sixteen positions on the turntable 20 in which the sixteen measuring units 10 are held will be respectively referred to as 1 ch (channel) to 16 ch.

The measuring unit 10 held in each channel is subjected to measurement by the measuring system shown in FIG. 2 each time it is stopped in the measuring position.

In this particular embodiment, the measuring units 10 in channels at intervals of 112.5° or at intervals of five channels are brought to the measuring position in sequence. That is, the measuring units 10 in 1ch, 6ch, 11ch and 16ch are brought to the measuring position in sequence in this order during a first rotation of the turntable in the regular direction, the measuring units 10 in 5ch, 10ch and 15ch are brought to the measuring position in sequence in this order during a second rotation of the turntable in the same direction, the measuring units 10 in 4ch, 9ch and 14ch are brought to the measuring position in sequence in this order during a third rotation of the turntable in the same direction, the measuring units 10 in 3ch, 8ch and 13ch are brought to the measuring position in sequence in this order during a fourth rotation of the turntable in the same direction, and the measuring units 10 in 2ch, 7ch and 12ch are brought to the measuring position in sequence in this order during a fifth rotation of the turntable in the same direction.

While one of the measuring units 10 is stopped in the measuring position and is subjected to measurement, other measuring units 10 stopped in the respective positions are subjected to operations corresponding to the positions, e.g., supply of a sample 15.

After the turntable 20 is intermittently rotated by five rotations and the measuring units 10 in all the channels are subjected to predetermined operations, the turntable 20 is continuously rotated by five rotations in the reverse direction. While the turntable 20 is rotated by five rotations in the regular direction, the rolling members 130c make revolution around the inner ring 130a and when the turntable 20 is rotated by five rotations in the reverse direction, each rolling member 130c is returned to the original revolution position.

Accordingly, when change with time of the properties shown in FIG. 3 is to be detected through a plurality of measurements on one sample 15, each measurement on one sample 15 can be done with the rolling members 130c held in the same revolution position by thus returning the rolling members 130c in the original position after each sample 15 is subjected to measurement during five rotations of the turntable 20 in the regular direction. With this arrangement, each measuring unit 10 can be held in the same position for all the measurements, whereby production of measuring errors due to fluctuation in the incident angle of the light beam 30 to the interface 11a from measurement to measurement.

The number of channels on the turntable 20, the angle by which the turntable 20 is intermittently rotated, the number of rotations of the turntable 20 for one measurement of the respective measuring units 10, and the like may be set freely without limited to those described above.

The control of the turntable 20 described above may be also applied to the leaky mode sensor shown in FIG. 9 or 10 without limited to the surface plasmon resonance sensor.

The measured values by the surface plasmon resonance sensor or the leaky mode sensor is apt to change according to environmental conditions such as the environmental temperature. This is because, for instance, the refractive index of the sample liquid changes with the temperature and the properties of the measuring optical system finely change with the temperature. A ninth embodiment of the present invention where change of the measured value due to change in the environmental conditions is prevented will be described, hereinbelow.

Figure 14:
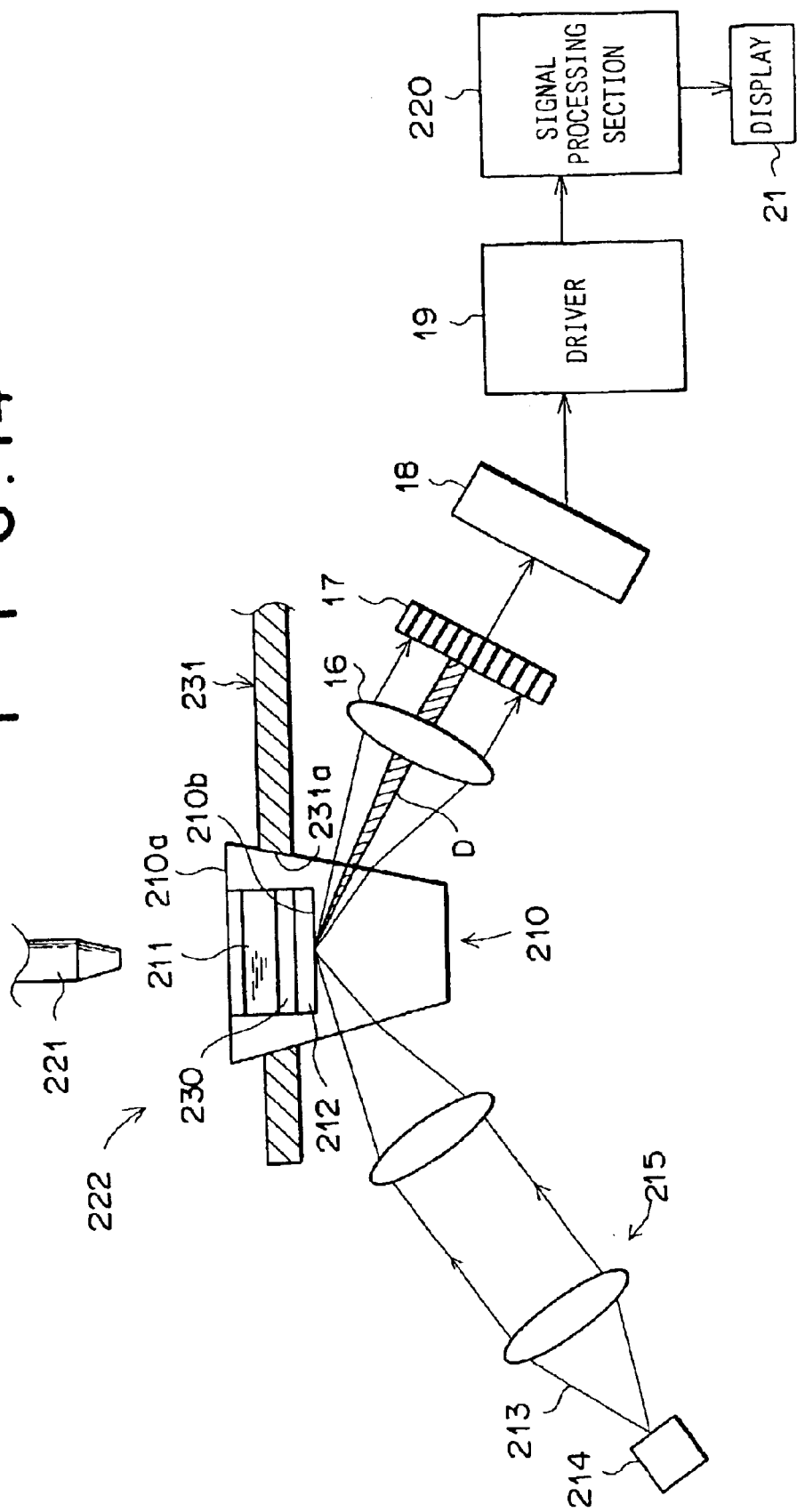
FIG. 14 is a side view partly cut away showing an important part of a surface plasmon resonance sensor in accordance with a ninth embodiment of the present invention.

FIG. 14 is a side view showing an important part of a measuring apparatus utilizing the phenomenon of attenuation in total internal reflection in accordance with the ninth embodiment of the present invention. The measuring apparatus of this embodiment is also a surface plasmon resonance sensor and comprises a dielectric block 210 which is substantially a quadrangular pyramid in shape, and a metal film layer 212 of gold, silver, copper, aluminum or the like formed on one surface (the upper surface as seen in FIG. 14) of the dielectric block 210.

The dielectric block 210 is formed of, for instance, transparent resin and is thickened at a part 210a circumscribing the metal film layer 212. The thickened part 210a of the dielectric block 210 functions as a sample holder containing therein a sample liquid 211. In this embodiment, a sensing medium 230 (which will be described later) is fixed on the metal film layer 212.

The dielectric block 210 forms together with the metal film layer 212 a disposable measuring unit (measuring chip) 222 and the disposable measuring units 222 are held in chip holding holes 231a formed in a turntable 231 which is the same as the turntable 20 shown in FIG. 1. With the dielectric blocks 210 are thus supported on the turntable 231, the turntable 231 is intermittently rotated predetermined angle by predetermined angle, and a sample liquid 211 is spotted onto the dielectric block 210 stopped in a predetermined position to be held in the sample holder 210a. When the turntable 231 is subsequently rotated by a predetermined angle, a dielectric block 210 is stopped in the measuring position shown in FIG. 14.

The surface plasmon resonance sensor of this embodiment is provided with, in addition to the dielectric block 210, a laser 214 such as a semiconductor laser which emits a light beam 213, an incident optical system 215 which causes the light beam 213 to enter the dielectric block 210 so that various angles of incidence of the light beam 213 to the interface 210b of the dielectric block 210 and the metal film layer 212 can be obtained, a collimator lens 16 which collimates the light beam 213 reflected in total internal reflection at the interference 210b into a parallel light beam, a photodetector 17 which detects the parallel light beam, a differential amplifier array 18 connected to the photodetector 17, a driver 19, a signal processing section 220 which may comprise, for instance, a computer system, and a display means 21 connected to the signal processing section 220.

FIG. 15 shows the electrical arrangement of the surface plasmon resonance sensor. As shown in FIG. 15, the driver 19 comprises sample holding circuits 22a, 22b, 22c . . . which respectively sample-hold the outputs of the differential amplifiers 18a, 18b, 18c . . . of the differential amplifier array 18, a multiplexer 23 into which the outputs of the sample-holding circuits 22a, 22b, 22c . . . , an A/D convertor 24 which digitizes the output of the multiplexer 23 and inputs digital signals into a signal processing section 220, a drive circuit 25 which drives the multiplexer 23 and the sample-holding circuits 22a, 22b, 22c . . . , and a controller 26 which controls the drive circuit 25 under the control of the signal processing section 220.

As shown in FIG. 14, the light beam 213 emanating from the laser 214 in the form of a divergent light beam is converged on the interface 210b of the dielectric block 210 and the metal film layer 212 by the optical system 215. Accordingly, the light beam 213 includes components impinging upon the interface 210b at various angles of incidence θ, which is not smaller than the total internal reflection angle. Accordingly, the light beam 213 is reflected in total internal reflection at the interface 210b, and the light beam 213 reflected at the interface 210b includes components reflected at various angles.

The light beam 213 is caused to impinge upon the interface 210b in the form of p-polarized light. This can be realized by positioning the laser 214 so that the light beam 213 is polarized in the suitable direction or by controlling the polarization direction of the light beam 213 with a wavelength plate, a polarizing plate or the like.

After reflected in total internal reflection at the interface 210b and collimated into a parallel light beam by the collimator lens 16, the light beam 213 is detected by the photodetector 17. In this particular embodiment, the photodetector 17 is a photodiode array comprising a plurality of photodiodes 17a, 17b, 17c . . . arranged in a row, and is disposed so that the photodiode array extends in perpendicular to the direction of travel of the parallel light beam 213 in the plane of FIG. 14. Accordingly, components of the light beam 213 reflected at different angles at the interface 210b are received by different photodiodes 17a, 17b, 17c . . . .

The outputs of the photodiodes 17a, 17b, 17c . . . are input into the differential amplifiers 18a, 18b, 18c . . . of the differential amplifier array 18, and at this time, the outputs of adjacent two photodiodes are input into one differential amplifiers. Accordingly, the outputs of the differential amplifiers 18a, 18b, 18c . . . may be considered to be values obtained by differentiating photodetecting signals output from the photodiodes 17a, 17b, 17c . . . in the direction which the photodiode array extends.

The outputs of the differential amplifiers 18a, 18b, 18c . . . are sample-held by the sample-holding circuits 22a, 22b, 22c . . . at predetermined timings and input into the multiplexer 23. The multiplexer 23 inputs the sampled outputs of the differential amplifiers 18a, 18b, 18c . . . into the A/D convertor 24 in a predetermined order. The A/D convertor 24 digitizes the sampled outputs and inputs the digitized signals into the signal processing section 220.

Figure 16A:
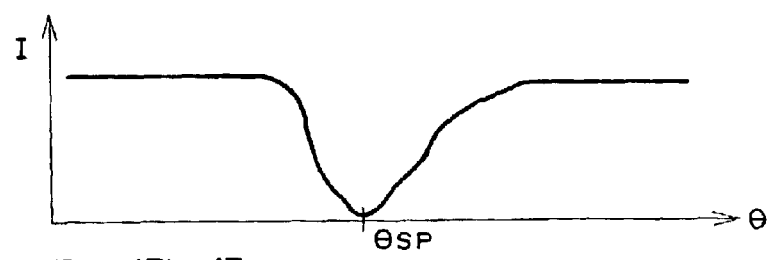
Figure 16B:
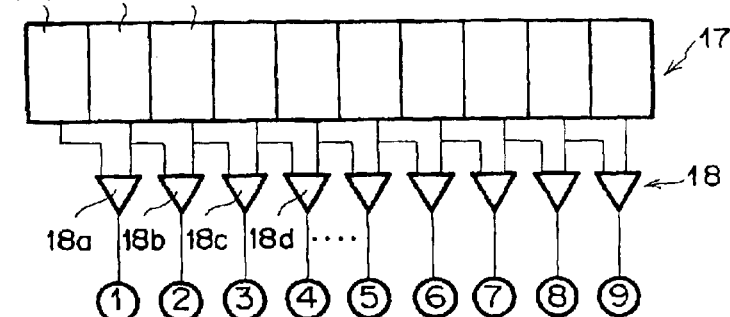
Figure 16C:
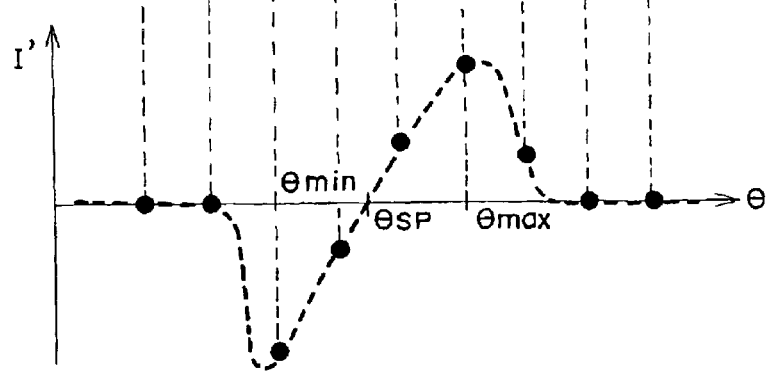

FIGS. 16A to 16C are views illustrating the relation between the intensity I of the reflected light beam 213 reflected at the interface 210b versus the angle of incidence q FIGS. 16A to 16C are views illustrating the relation between the intensity I of the reflected light beam 213 reflected at the interface 210b versus the angle of incidence θ of the light beam 213 to the interface 210b and the outputs of the differential amplifiers 18a, 18b, 18c . . . . It is assumed that the relation between the intensity I of the reflected light beam 213 reflected at the interface 210b versus the angle of incidence θ of the light beam 213 to the interface 210b is as shown in FIG. 16A.

Light impinging upon the interface 210b at a particular angle of incidence $\theta_{sp}$ generates surface plasmon on the interface between the metal film layer 212 and the sample 211 and accordingly, for light impinging upon the interface 210b at a particular angle of incidence $\theta_{sp}$, the intensity I of light reflected in total internal reflection at the interface 210b sharply drops. That is, the angle $\theta_{sp}$ is the total reflection attenuation angle and the intensity I takes a minimum value at the angle $\theta_{sp}$. The drop of the intensity I is observed as a dark line in the reflected light as denoted by D in FIG. 14.

FIG. 16B shows the direction in which the photodiodes 17a, 17b, 17c . . . are arranged and the positions of the photodiodes 17a, 17b, 17c . . . in the direction are in one to one correspondence with the angles of incidence θ.

The relation between the positions of the photodiodes 17a, 17b, 17c . . . in the direction in which the photodiodes 17a, 17b, 17c . . . are arranged, that is, the angles of incidence θ, and the outputs I' of the differential amplifiers 18a, 18b, 18c . . . (differential values of the intensity I of the reflected light) is as shown in FIG. 16C.

The signal processing section 220 selects a differential amplifier whose output is the closest to or equal to 0 (the differential amplifier 18d in the example shown in FIG. 16C) and causes the display means 21 to display the differential value I' output from the selected differential amplifier after carrying out correction processing to be described later on the differential value I'.

Thereafter, each time a predetermined time lapses, a differential value I' output from the selected amplifier 18d is displayed after subjected to the correction processing.

Since the differential value I' increases or decreases in response to right and left movement of the curve shown in FIG. 16A, which represents change of the dielectric constant or the refractive index of the material in contact with the metal film layer 212 (FIG. 14) of the measuring unit 222. Accordingly, by continuously measuring the differential value I', the change of the refractive index or the properties of the material in contact with the metal film layer 212 can be detected.

Especially, in this embodiment, since the aforesaid sensing medium 230 which combines with a specific material (sample material) in the sample liquid 211 is fixed on the metal film later 212, and the refractive index of the sensing medium 230 changes with the state of bonding of the sensing medium 230 and the specific material, change of the state of bonding of the sensing medium 230 and the specific material can be detected by continuously measuring the differential value I'. In this case, both the sample liquid 211 and the sensing medium 230 can be analyzed. As such a combination of the sensing medium 230 and the specific material, for instance, combinations of antigen and antibody are known.

As can be understood from the description above, since a photodiode array comprising a plurality of photodiodes 17a, 17b, 17c . . . arranged in a row is employed as the photodetector 17, the dark line can be detected even if the curve shown in FIG. 16A largely moves right and left according to the kind of the sample liquid 211, whereby a large dynamic range of measurement can be ensured.

Instead of a differential amplifier array 18 comprising a plurality of differential amplifiers 18a, 18b, 18c . . . , a single differential amplifier may be employed. In this case, outputs of the photodiodes 17a, 17b, 17c . . . are switched by a multiplexer so that outputs of pairs of adjacent photodiodes are input into the single differential amplifier in sequence.

The aforesaid correction processing to be carried out on the differential value I' will be described in detail, hereinbelow. As shown in FIG. 14, an automatic reference liquid supply mechanism 221 is provided above a position in which the measuring unit 222 on the turntable 231 is stopped. The structure of the automatic reference liquid supply mechanism 221 is basically the same as that of the sample liquid supply mechanism 70 shown in FIG. 1 and the automatic reference liquid supply mechanism 221 supplies one of the measuring units 222 on the turntable 231 with the reference liquid. The measuring unit 222 supplied with the reference liquid is supplied with no sample liquid.

The sample liquid 211 in this embodiment comprises a sample material dissolved in solvent, and as the reference liquid, the solvent is employed. For example, when the sample material is Insulin-Biotin Labeled, and the solvent is PBS (phosphoric acid buffer) containing therein 0.1% BSA solution, PBS containing therein 0.1% BSA solution is employed as the reference liquid.

With one of the measuring units 222 on the turntable 231 supplied with the reference liquid and the other measuring units 222 supplied with respective sample liquids 211, the differential values I' of all the measuring units 222 including the measuring unit supplied with the reference liquid are measured.

FIG. 17A shows change with time of the differential value I' on a sample liquid 211 and that on a reference liquid, and FIG. 17B shows change with time of the differential value I' on another sample liquid 211 and that on another reference liquid. In FIGS. 17A and 17B, change with time of the differential value I' on the sample liquid 211 is shown by hutched circles (measured data) and change with time of the differential value I' on the reference liquid is shown by white circles (correction data).

As described above, the state of bonding of the sensing medium 230 and the specific material in the sample liquid 211 can be determined by detecting change with time of the measured data, that is, the differential value I' on the sample liquid 211. However, the measured data is affected by environmental conditions such as the environmental temperature since, for instance, the refractive index of the sample liquid 211 changes with the temperature and the like, and the optical distances between elements of the measuring optical system finely change with the temperature and the like.

The signal processing section 220 corrects the measured differential value I' by subtracting the value of the correction data from the measured differential value I'. That is, the corrected data is as shown by the solid line FIGS. 17A and 17B. The subtraction is made between the sample liquid and the reference liquid which are the same in reaction time with the sensing medium 230.

The differential value I' on the reference liquid depends upon the refractive index of the reference liquid, i.e., the solvent of the sample liquid 211 irrespective of the specific material (sample material) in the sample liquid 211, and also reflects fine displacement of elements of the optical system, if any. Accordingly, by subtracting the differential value I' on the reference liquid from the measuring data, that is, the differential value I' on the sample liquid 211, change of the refractive index of the solvent and/or change of the properties of the optical system can be compensated for, whereby the corrected data can purely represent properties of the sample material in the sample liquid 211.

A tenth embodiment of the present invention will be described, hereinbelow. FIG. 18 is a plan view showing an important part of a measuring apparatus utilizing the phenomenon of attenuation in total internal reflection in accordance with the tenth embodiment of the present invention. The measuring apparatus of this embodiment is a surface plasmon resonance sensor and in FIG. 18, elements analogous to those shown in FIG. 7 are given the same reference numerals. That is, reference numeral 20 denotes a turntable which is intermittently rotated in the direction of arrow R, reference numeral 70 denotes an automatic sample supply mechanism, reference numeral 76 denotes a chip supply means, reference numeral 77 denotes a surface plasmon resonance sensing means and reference numeral 78 denotes a measuring chip discharge means.

In this particular embodiment, the turntable 20 supports 96 measuring units 80 and is intermittently rotated 75° by 75° (=360/96). The chip supply means 76 transfers the measuring units 80 on a well-plate 240, containing therein 96 measuring units 80, set in a well-plate setting station 241, one by one to the turntable 20. In this embodiment, a sensing medium 14 similar to that shown in FIG. 2 is fixed on the metal film layer of each of the measuring units 80, and each measuring unit 80 is supplied to the turntable 20 in the state.

The sample liquids 15 are stored in wells of 96 well plates 242 and the sample supply mechanism 70 transfers the samples 15 in the well-plates 242 set in a well-plate setting station 243 one by one to the measuring units 80 on the turntable 20. Then the surface plasmon resonance sensing means 77 carried out measurement on the respective measuring units 80 in the manner described above. After the measurement, the measuring units 80 are discharged from the turntable 20 to a discharge well-plate 244 by the measuring chip discharge means 78.

The apparatus with the arrangement described above can be suitably employed in random screening for finding a specific material combined with a predetermined sensing material as described above.

As described above, measured values by the surface plasmon resonance sensor vary with change of the refractive index of the sample liquid due to change of the environmental temperature. An arrangement for suppressing change of the temperature of the sample liquid 15 will be described, hereinbelow.

FIG. 19 is a side view of the well-plate setting station 243 of the automatic sample supply mechanism 70. As shown in FIG. 19, there is provided in the well-plate setting station 243 a metal block 245 having 96 recesses 245a which receives the wells (portions for holding the sample liquid 15) of the well plate 242. A temperature control means 246 which may comprise, for instance, a Peltier element or a heater for changing the temperature of the metal block 245 and a temperature sensor 247 are connected to the metal block 245. The temperature detecting signal S1 of the temperature sensor 247 is input into a controller 248 and the controller 248 controls the temperature control means 246 on the basis of the temperature detecting signal S1 to keep the temperature of the metal block 245 at a predetermined temperature. It is preferred that the metal block 245 be formed of a metal having a high heat conductivity such as copper.

When the metal block 245 is thus kept at the predetermined temperature, the sample liquid 15 in the wells of the well-plate 242 can be kept also at the predetermined temperature, whereby change of the refractive index of the sample liquid 15 can be prevented and fluctuation of the measured values by the surface plasmon resonance sensor can be prevented.

The metal 245 may be kept at the predetermined temperature by circulating temperature-controlled liquid instead of using a temperature control means 246 such as a Peltier element of a heater as in a surface plasmon resonance sensor in accordance with an eleventh embodiment of the present invention shown in FIG. 20.

That is, in the surface plasmon resonance sensor shown in FIG. 20, the metal block 245 is provided with a flow passage 245b for uniformly circulating liquid through the metal block 245. A circulating passage 250 is connected to the upstream and downstream ends of the flow passage 245b. A pump 251 for flowing liquid such as water under pressure and a heater 252 for heating the liquid are provided in the circulating passage 250.

The heater 252 is controlled by a temperature sensor 247 and a controller 248 which are similar to those shown in FIG. 19 so that the liquid flowing through the flow passage 245b is kept at a predetermined temperature and accordingly, the metal block 245 is kept at a predetermined temperature. Thus, change of the refractive index of the sample liquid 15 can be prevented and fluctuation of the measured values by the surface plasmon resonance sensor can be prevented.

In view of preventing fluctuation of the measured values due to change in the temperature of the sample liquid 15, it is preferred that change of the temperature of the sample liquid 15 supplied to the measuring units 80 on the turntable 20 be further suppressed. A surface plasmon resonance sensor in accordance with a twelfth embodiment of the present invention, in which change of the temperature of the sample liquid 15 supplied to the measuring units 80 on the turntable 20 is further suppressed, will be described, hereinbelow.

FIG. 21 is a perspective view showing an important part of a surface plasmon resonance sensor in accordance with the twelfth embodiment of the present invention. In FIG. 21, elements analogous to those shown in FIGS. 18 and 19 are given the same reference numerals.

In this embodiment, the upper side of the turntable 20 is covered with a cover 260 so that air just above the turntable 20 is confined inside the cover 260 and air communication between the inside and the outside of the cover 260 becomes difficult. The cover 260 is a low substantially cylindrical member with a closed upper end. The cover 260 is provided with a small opening 260a of a size just enough to receive a sample liquid spotting pipette 71 of the automatic sample supply mechanism 70, an opening 260b of a size just enough to receive the surface plasmon resonance sensing means 77 comprising a casing 262 holding therein the optical system of the sensing means 77, a small opening 260c for receiving a chip supply means (not shown), and a small opening 260d for receiving a chip discharge means (not shown).

On the cover 260 are mounted a temperature control means 246 which may comprise, for instance, a Peltier element or a heater for changing the temperature inside the cover 260 and a temperature sensor 247 which detects the temperature inside the cover 260. The temperature detecting signal S1 of the temperature sensor 247 is input into a controller 248 and the controller 248 controls the temperature control means 246 on the basis of the temperature detecting signal S1 to keep the temperature inside the cover 260 at a predetermined temperature.

When the temperature inside the cover 260 is thus kept at the predetermined temperature, the sample liquid 15 in the measuring units 80 on the turntable 20 can be kept also at the predetermined temperature, whereby change of the refractive index of the sample liquid 15 can be prevented and fluctuation of the measured values by the surface plasmon resonance sensor can be prevented.

Both the mechanism for keeping the temperature of the sample liquid 15 in the measuring units 80 on the turntable 20 at a preset temperature described above and the mechanism for keeping the temperature of the sample liquid 15 before supplied to the measuring units 80 at the preset temperature shown in FIG. 19 or 20 may be employed. With this arrangement, fluctuation of the measured values by the surface plasmon resonance sensor due to change in temperature can be more effectively prevented.

The mechanism for keeping the temperature of the sample liquid 15 may be applied also to the leaky mode sensor shown in FIG. 9 or 10 in order to prevent fluctuation of the measured values due to change in temperature.

When the sample liquid 15 is of a type where a sample material is dissolved in solvent, it is desired for the sample liquid 15 to be well stirred to uniform the concentration of the sample material before measurement in order to correctly analyze properties of the sample material. This is true also of leaky mode sensors shown in FIGS. 9 and 10.

In order to well stir the sample liquid 15, for instance, in the apparatus shown in FIG. 21, the turntable 20 may be rotated in one direction at a high speed or may be alternately rotated in one direction and the other before measurement with the measuring units 80 supported thereon.

Otherwise, the sample liquid 15 may be stirred by, after each sample liquid 15 is spotted into the measuring unit 80 by the pipette 71, dipping the pipette 71 in the sample liquid 15 and causing the pipette 71 to repeat sucking the sample liquid 15 and discharging the same a plurality of times.

Though the embodiments described above employ a turntable as the support for supporting measuring units, embodiments of the present invention employing a support which is linearly moved back and forth will be described hereinbelow.

Figure 22:
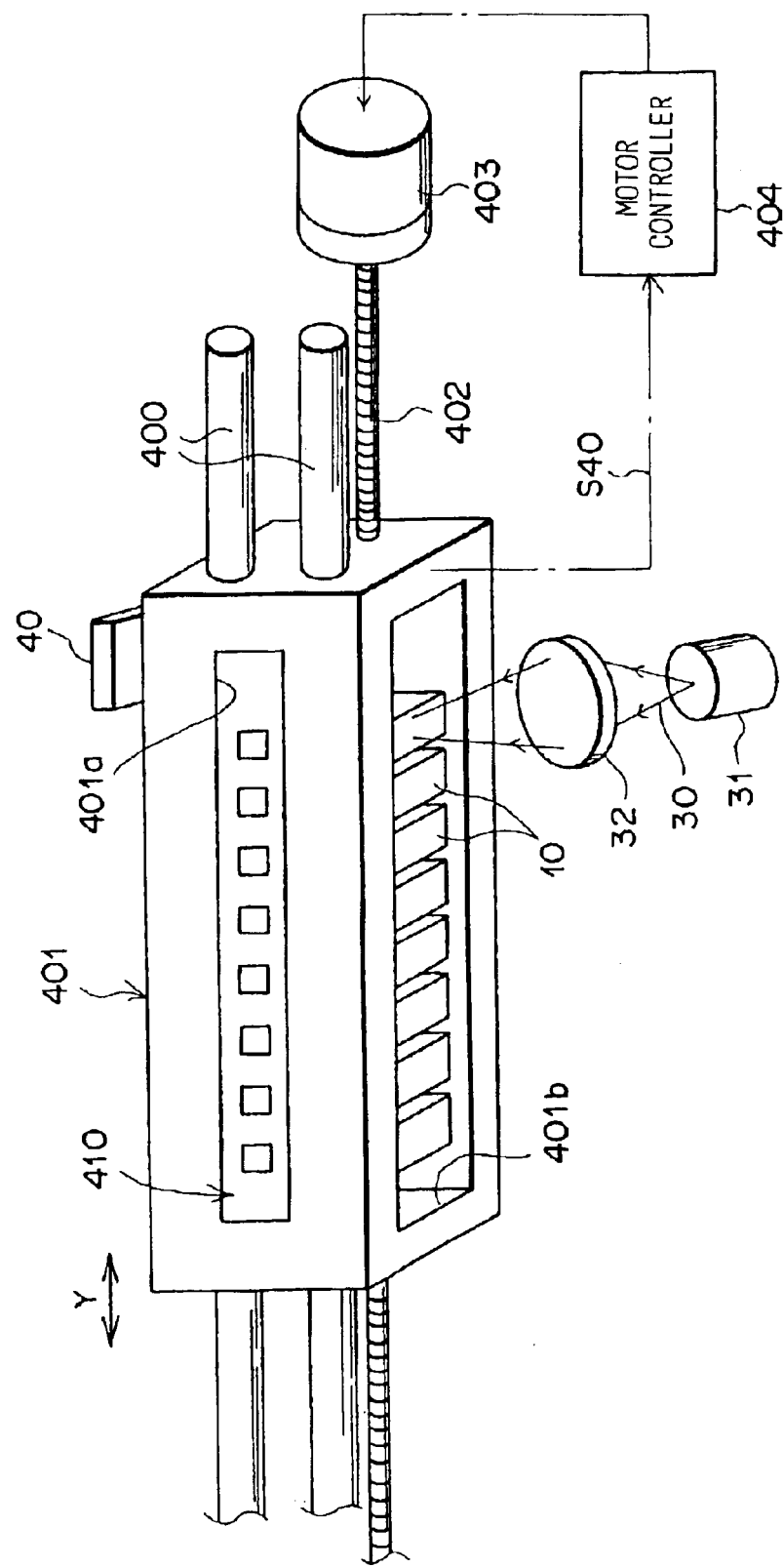
FIG. 22 is a perspective view showing a surface plasmon resonance sensor in accordance with a thirteenth embodiment of the present invention.

FIG. 22 is a perspective view showing a surface plasmon resonance sensor in accordance with a thirteenth embodiment of the present invention. In FIG. 22, elements analogous to those shown in FIG. 2 are given the same reference numerals.

In the surface plasmon resonance sensor of this embodiment, as the support for supporting a plurality of measuring units 10 is employed a slide block 401 which is fitted on a pair of parallel guide rods 400 to be linearly slidable in the direction of arrow Y. The slide block 401 is in mesh with a precision screw 402 parallel to the guide rods 400. The precision screw 402 is rotated in the regular and reverse directions by a pulse motor 403, which forms together with the precision screw 402 a support drive means.

The pulse motor 403 is driven under the control of a motor controller 404. That is, an output signal S40 of a linear encoder (not shown) which is incorporated in the slide block 401 to detect the position of the slide block 401 in the longitudinal direction of the guide rods 400 is input into the motor controller 404, and the motor controller 404 controls the pulse motor 403 on the basis of the output signal S40.

A laser 31 and a condenser lens 32 are provided on one side of the guide rods 400 and a photodetector 40 is disposed on the opposite side of the guide rods 400. The laser 31, the condenser lens 32 and the photodetector 40 are basically the same as those shown in FIG. 2.

Figure 23:
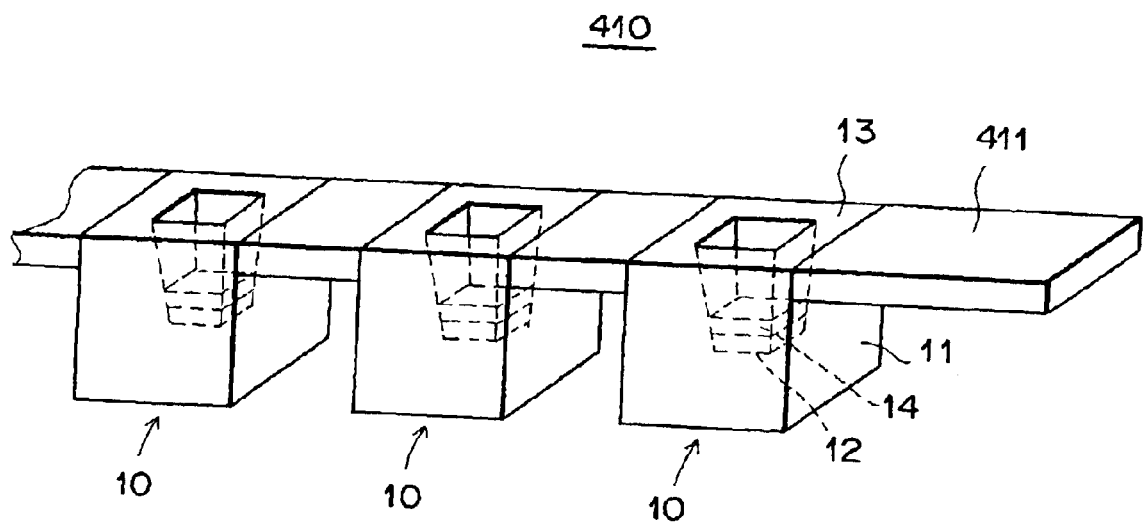
FIG. 23 is a perspective view showing a part of the surface plasmon resonance sensor shown in FIG. 22.

In this embodiment, comprising stick-like measuring unit train 410 comprising eight measuring units 10 fixed together is employed, and eight measuring units in a row are set on the slide block 401. FIG. 23 shows in detail the structure of the measuring unit train 410. As shown in FIG. 23, the measuring unit train 410 comprises eight measuring units 10, each being the same as that shown in FIG. 2, connected together by a connecting member 411.

For example, a plurality of (twelve in this particular embodiment) the measuring unit trains 410 are set on a plate 420, and the measuring units 10 are transported and handled in this state. That is, the measuring units are placed on a plate 420 by 96 pieces and transported and handled on the plate.

Figure 25:
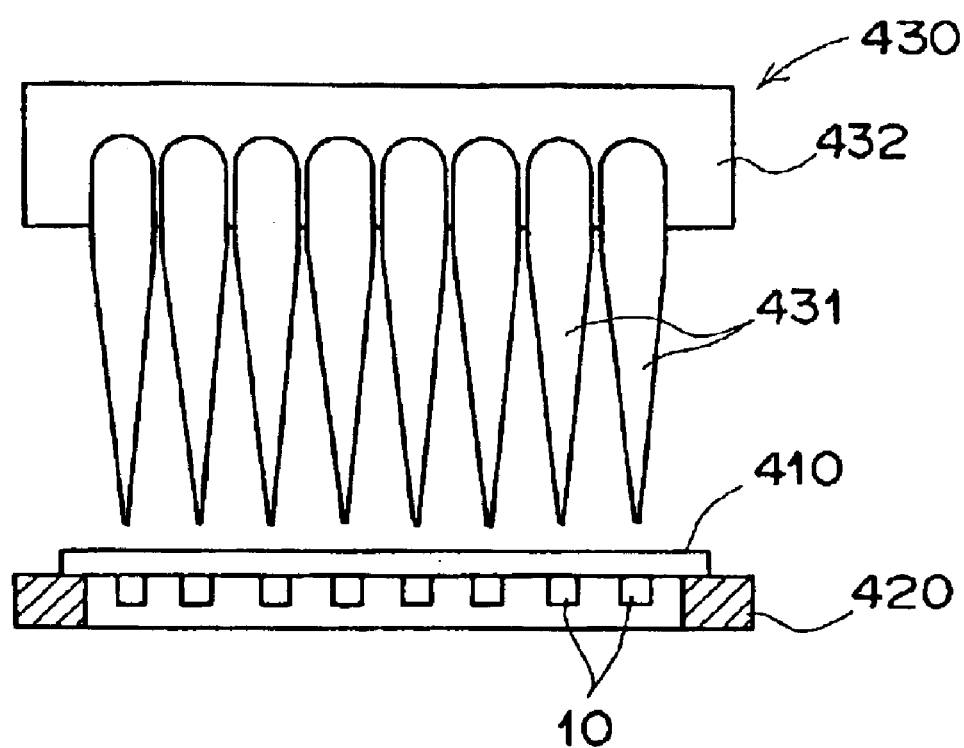
FIG. 25 is a front view showing a part of the surface plasmon resonance sensor shown in FIG. 22.

When a plurality of measuring units 10 are handled in one piece as a measuring unit train 410, it is preferred that a dispensing mechanism 430 such as shown in FIG. 25 be employed as the means for supplying the sample liquid to the measuring units 10. The dispensing mechanism 430 comprises a plurality of dispensing nozzles 431 the number of which is equal to the number of the measuring units 10 of the measuring unit train 410 and which are supported on a support member 432 at the same pitches as those at which the measuring units 10 are connected in the measuring unit train 410. The dispensing mechanism 430 can supply the sample liquid 15 to all the measuring units 10 of one measuring unit train 410 at one time, whereby sample supply can be efficiently accomplished.

When the surface plasmon resonance sensor shown in FIG. 22 is operated, one of the measuring unit trains 410 on the plate 420 shown in FIG. 24 is set to a unit setting portion 401*a* of the slide block 401 by a supply means (not shown). As shown in FIG. 22, the slide block 401 is a frame-like member having a plurality of through holes 401*b* extending through the slide block 401 in the horizontal direction (vertical direction as seen in FIG. 22), the light beam 30 emitted from the laser 31 can be projected onto the measuring unit 10 supported on the slide block 401 through the through hole 401*b* and the light beam 30 reflected in total internal reflection at the interface of the dielectric block 11 and the metal film layer 12 can be detected by the photodetector 40 the through hole 401*b*.

When surface plasmon resonance is measured by the apparatus of this embodiment, the pulse motor 403 is driven to move the slide block 401 to bring a first measuring unit 10, that is, the rightmost measuring unit 10 in FIG. 22, to a measuring position where the measuring unit is exposed to the light beam 30. Then surface plasmon resonance of the first measuring unit 10 is measured in the manner described above.

After the measurement on the first measuring unit 10, the pulse motor 403 is driven to move the slide block 401 by a distance equal to the pitch of the measuring units 10 to bring a second measuring unit 10 to the measuring position. Surface plasmon resonance of the second measuring unit 10 is then measured. In this manner, intermittent movement of the slide block 401 and measurement of surface plasmon resonance are repeated until all the eight measuring units 10 are subjected to measurement.

Thereafter, the pulse motor 403 is rotated in the reverse direction to return the slide block 401 to the original position. When measurement of surface plasmon resonance is to be carried out once on each sample, the measuring unit train 410 is removed from the slide block 401 there. To the contrast, when measurement of surface plasmon resonance is to be carried out a plurality of times on each sample, the slide block 401 is moved intermittently from left to right again to bring the eight measuring units 10 to the measuring position in sequence. Then returning the slide block 401 to the original position and intermittently moving the slide block 401 from left to right are repeated according to the number of measurements to be carried out on each sample.

The mechanism of linearly moving the slide block 401 described above may be also applied to the leaky mode sensor shown in FIG. 9 or 10 without limited to the surface plasmon resonance sensor.

Figure 27:
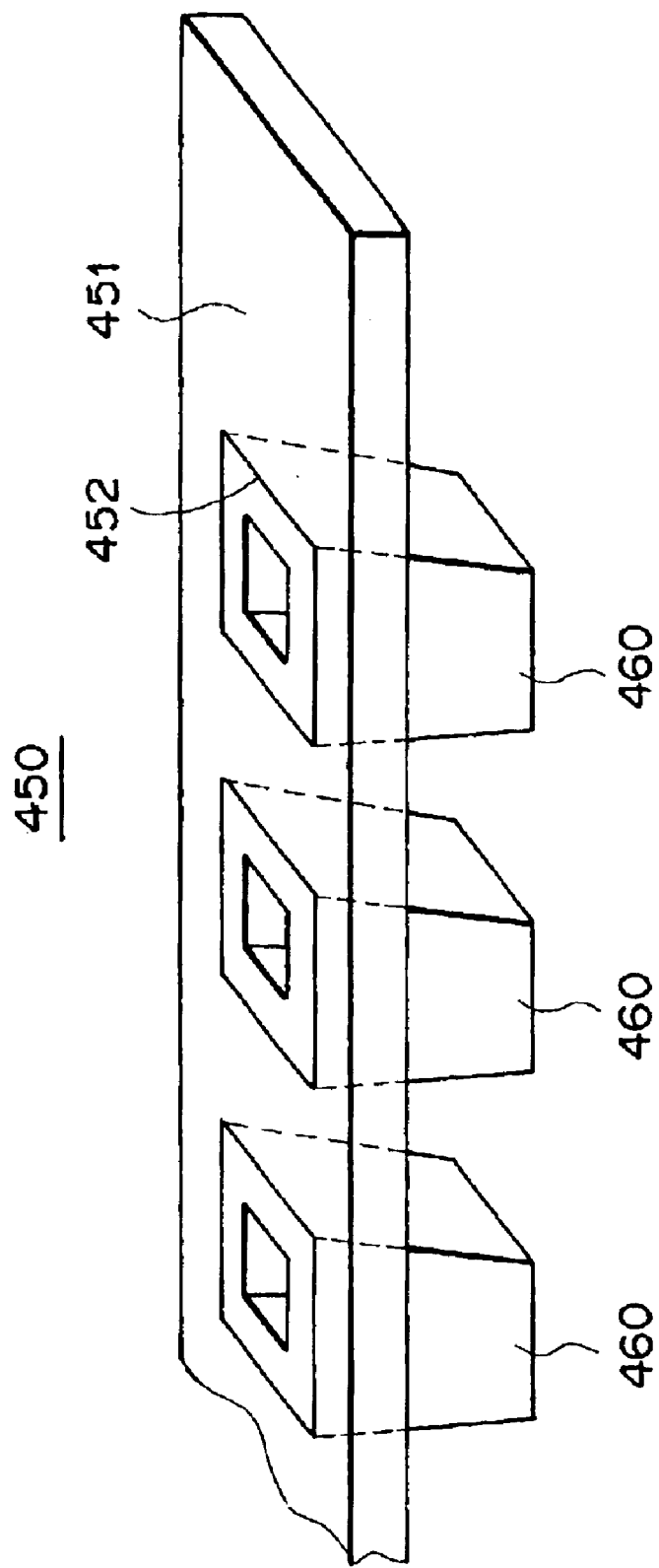
FIG. 27 is a perspective view showing another example of a measuring unit train employed in the surface plasmon resonance sensor of the present invention.

Measuring unit trains shown in FIGS. 26 and 27 may be employed in place of the measuring unit train 410. The measuring unit train 440 shown in FIG. 26 comprises a dielectric bar 441 in the form of a rectangular column formed of the same material as the dielectric block 11 shown in FIG. 23. A plurality of holes 442 having a closed bottom are formed in the dielectric bar 441, and a metal film layer 12 and a sensing medium 14 are formed on the bottom of each hole 442. That is, in this measuring unit train 440, each hole forms a measuring unit.

The measuring unit train 440 with this arrangement is advantageous over that shown in FIG. 23 which is formed by forming a plurality of measuring units 10 one by one and connecting the measuring units 10 in that the measuring unit 440 can be produced more easily and at a lower cost as compared with that shown in FIG. 23.

The measuring unit train 450 shown in FIG. 27 comprises a plurality of measuring units 460 fitted in a plurality of unit support holes 452 formed in a unit support plate 451. Though being basically the same as the measuring unit 10 shown in FIG. 23, the measuring unit 460 is substantially a quadrangular pyramid in shape and accordingly surely fitted in the unit support hole 452 which is tapered downward.

In the case of such a measuring unit train 450, a plurality of measuring unit trains 450 may be set on a plate such as a plate 420 shown in FIG. 24. Otherwise, one unit support plate 451 loaded with a plurality of measuring units 460 may be fixed on a slide block 401 shown in FIG. 22 and the measuring units 460 may be replaced by another series of measuring units 460 after measurement.

The measuring unit train 410 shown in FIG. 23 or the measuring unit train 440 where the measuring units are fixed to each other not to be separable is advantageous over the measuring unit train 450 of this embodiment in that the measuring units can be more easily located in place and easier to handle since a small measuring unit need not be handled, which contributes to increase in measuring efficiency.

Figure 28:
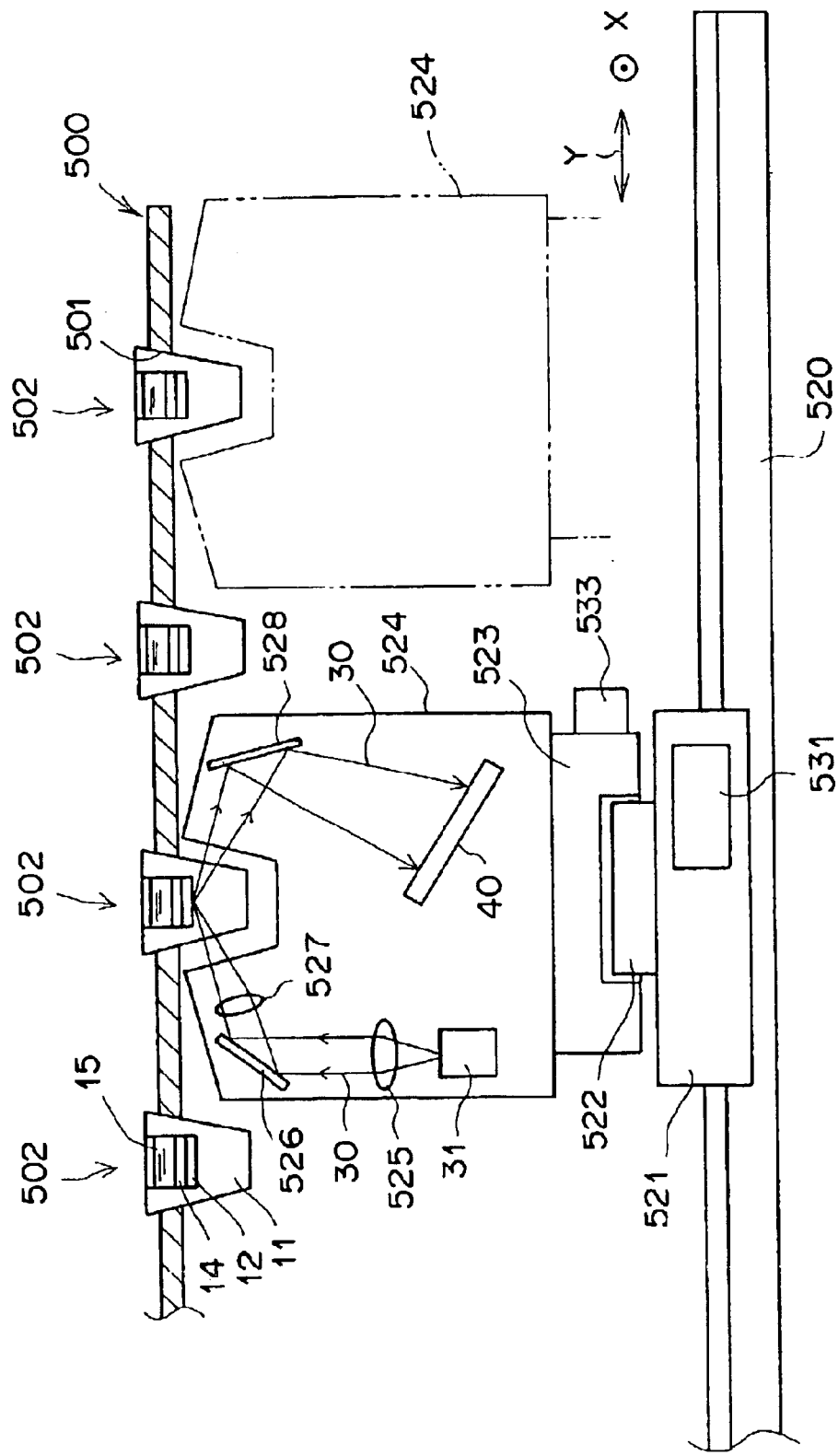
FIG. 28 is a fragmentary side view of a surface plasmon resonance sensor in accordance with a fourteenth embodiment of the present invention.

A surface plasmon resonance sensor in accordance with a fourteenth embodiment of the present invention will be described, hereinbelow. FIG. 28 is a side view showing a surface plasmon resonance sensor in accordance with the fourteenth embodiment of the present invention. In FIG. 28, elements analogous to those shown in FIG. 2 are given the same reference numerals.

In this embodiment, a support bar 500 which linearly extends in the direction of arrow Y is employed as the support for supporting a plurality of measuring units 10. A plurality of unit support holes 501 are provided at predetermined intervals in the longitudinal direction of the support 501, and one measuring unit 502 is held in each unit support holes 501. Though basically the same as the measuring unit shown in FIG. 2, the measuring unit 502 is substantially a quadrangular pyramid in shape and accordingly surely fitted in the unit support hole 501 which is tapered downward.

A guide rail 520 is provided below the support bar 500 to extend in parallel to the support bar 500. A slide block 521 is mounted on the guide rail 520 to be slidable along the guide rail 522 in the direction of arrow Y. The slide block 521 is driven back and forth along the guide rail 520 by a drive means 531 mounted thereon.

A guide rail 522 is fixed on the slide block 521 to extend in the direction of arrow X in perpendicular to the direction of arrow Y. A slide block 523 is mounted on the guide rail 522 to be slidable along the guide rail 523 in the direction of arrow X. The slide block 523 is driven back and forth along the guide rail 522 by a drive means 533 mounted thereon.

An optical unit 524 is fixedly mounted on the slide block 523. The optical unit 524 comprises a laser 31 which emits a measuring light beam 30, a collimator lens 525 which collimates to a parallel light beam the light beam 30 which emitted from the laser 31 as a divergent light beam, a mirror 526 which reflects the collimated laser beam 30 toward the interface between the dielectric block 11 and the metal film layer 22 of the measuring unit 502, a condenser lens 527 which condenses the light beam 30 reflected by the mirror 526, a mirror 528 which reflects the light beam 30 reflected at the interface, and a photodetector 40 which detects the light beam 30 reflected by the mirror 528.

When surface plasmon resonance is to be measured by the apparatus of this embodiment, the optical unit 524 is held in the standby position shown by the chained line in FIG. 28. In the standby position, the optical unit 524 is held in alignment with the first measuring unit 502 (the rightmost measuring unit as seen in FIG. 28) in the direction of Y and held out of alignment with the first measuring unit 502 (held forward or rearward of the first measuring unit 502) in the direction X.

With the optical unit 524 held in the standby position, a plurality of measuring units 502 are supplied to the unit support holes 501 of the support bar 500 by a supply means (not shown), and a sample liquid 15 is supplied to each measuring unit 502. Then the drive means 533 is driven in the regular direction to move the slide block 523 by a predetermined distance in the direction X so that the optical unit 524 is brought to a position in the direction X where the optical unit 524 can cause the light beam 30 to impinge upon the interface between the dielectric block 11 and the metal film layer 22 of the first measuring unit 502.

Then the laser 31 is operated to project the light beam 30 to the interface and the light beam 30 reflected in total internal reflection at the interface is detected by the photodetector 40, whereby surface plasmon resonance is measured. The measurement of surface plasmon resonance is carried out in the same manner as described above.

After measurement on the first measuring unit 502, the drive means 533 is reversed to reverse the slide block 523 by the predetermined distance in the direction of X so that the optical unit 524 is returned to the standby position. Thereafter, the drive means 531 is driven to move the slide block 521 leftward by a distance equal to pitch of the unit support holes 501. Then the drive means 533 is driven in the regular direction to move the slide block 523 by the predetermined distance in the direction X so that the optical unit 524 is brought to a position in the direction X where the optical unit 524 can cause the light beam 30 to impinge upon the interface between the dielectric block 11 and the metal film layer 22 of the second measuring unit 502.

Then the laser 31 is operated to project the light beam 30 to the interface and the light beam 30 reflected in total internal reflection at the interface is detected by the photodetector 40, whereby surface plasmon resonance is measured.

The same procedure is repeated for the third, fourth, fifth . . . measuring units 502. After measurement on all the measuring units 502 is finished, the drive means 531 is reversed and the slide block 521 is returned to the standby position.

Then by repeating the same procedure, the sample liquid 15 in one measuring unit 502 can be subjected to measurement a plurality of times. After a desired number of times of measurement on each sample 15 is finished, the optical unit 524 is returned to the standby position and the measuring units 502 is removed from the support bar 500 by a discharge means not shown.

Then another set of measuring units 502 are supplied to the unit support holes 501 of the support bar 500 and another set of sample liquids 15 are supplied to the measuring units 502. Thereafter, the sample liquids 15 are subjected to measurement in the same manner.

The mechanism in which the optical unit 524 is moved with the measuring units kept stationary may be also applied to the leaky mode sensor shown in FIG. 9 or 10 without limited to the surface plasmon resonance sensor. Further, it is possible to support a plurality of measuring units along the periphery of a circular support and to cause the measuring optical system to move along the measuring units.

A surface plasmon resonance sensor in accordance with a fifteenth embodiment of the present invention, where mistaking the result of measurement for one sample for that of a different sample is prevented, will be described, hereinbelow.

Figure 29:
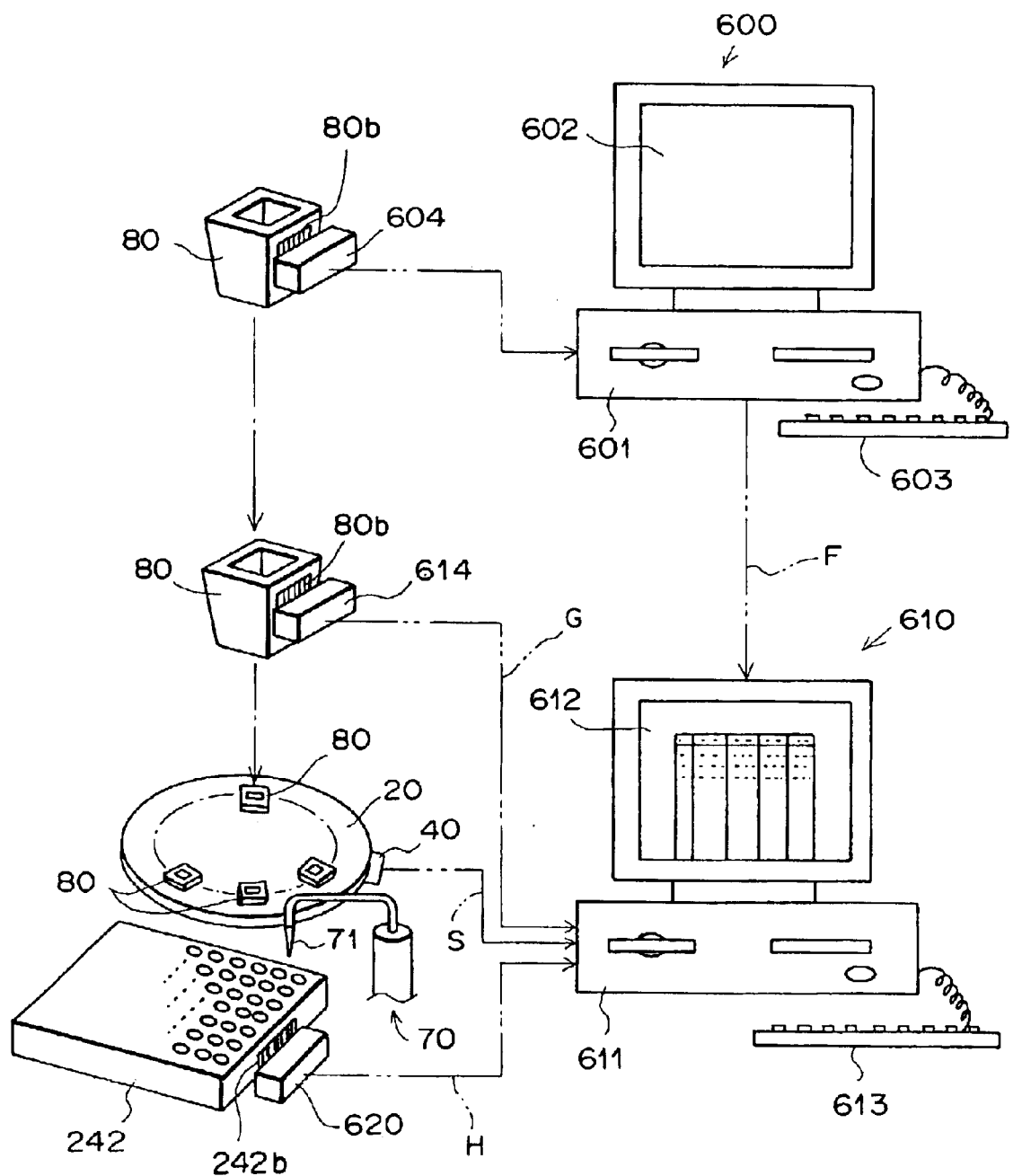
FIG. 29 is a schematic view showing a surface plasmon resonance sensor in accordance with a fifteenth embodiment of the present invention.

FIG. 29 is a side view showing a surface plasmon resonance sensor in accordance with the fifteenth embodiment of the present invention. In the surface plasmon resonance sensor of this embodiment, surface plasmon resonance is measured by the use of a turntable 20 and measuring units 80 which are basically the same as those shown in FIG. 21. The samples are stored in wells of a well-plate 242 similar to that shown in FIG. 18, and are dispensed to the measuring units 80 by an automatic sample supply mechanism 70 provided with dispensing pipettes 71.

The apparatus of this embodiment is used, for instance, in random screening and a sensing medium is fixed on a metal film layer formed on one surface of a dielectric block of the measuring unit 80. Measurement by the apparatus is applied to sample liquids which can contain a specific material (sample material) which bonds with the sensing medium. Each of the measuring units 80 is provided with an ID barcode 80b representing the production number (a serial number) of the measuring unit 80. The sensing medium will be referred to as a "receptor" and the sample material will be referred to as a "regand", hereinbelow.

The surface plasmon resonance sensor of this embodiment is further provided with a computer system 600 which manages information on surface plasmon resonance measurement and a computer system 610 which outputs result of measurement on the basis of the output signal S of the photodetector 40. The computer system 600 may be, for instance, a general purpose personal computer comprising a computer body 601, a display 602, and a keyboard 603. A first barcode reader 604 which reads the barcodes 80b on the measuring units 80 is connected to the computer body 601. The first barcode reader 604 is placed where a receptor is fixed to the measuring unit 80.

Also the computer system 610 may be, for instance, a general purpose personal computer comprising a computer body 611, a display 612, and a keyboard 613. A second barcode reader 614 which reads the barcodes 80b on the measuring units 80 is connected to the computer body 611. The second barcode reader 614 is placed where a regand is dispensed to the measuring unit 80.

A barcode 242b representing the kind of regands stored in each well of the well-plate 242 is applied to the well-plate 242. A third barcode reader 620 which reads the barcode 242b is connected to the computer body 611 of the computer system 610.

Operation of the surface plasmon resonance sensor of this embodiment will be described with reference to also FIG. 30, hereinbelow.

Figure 30:
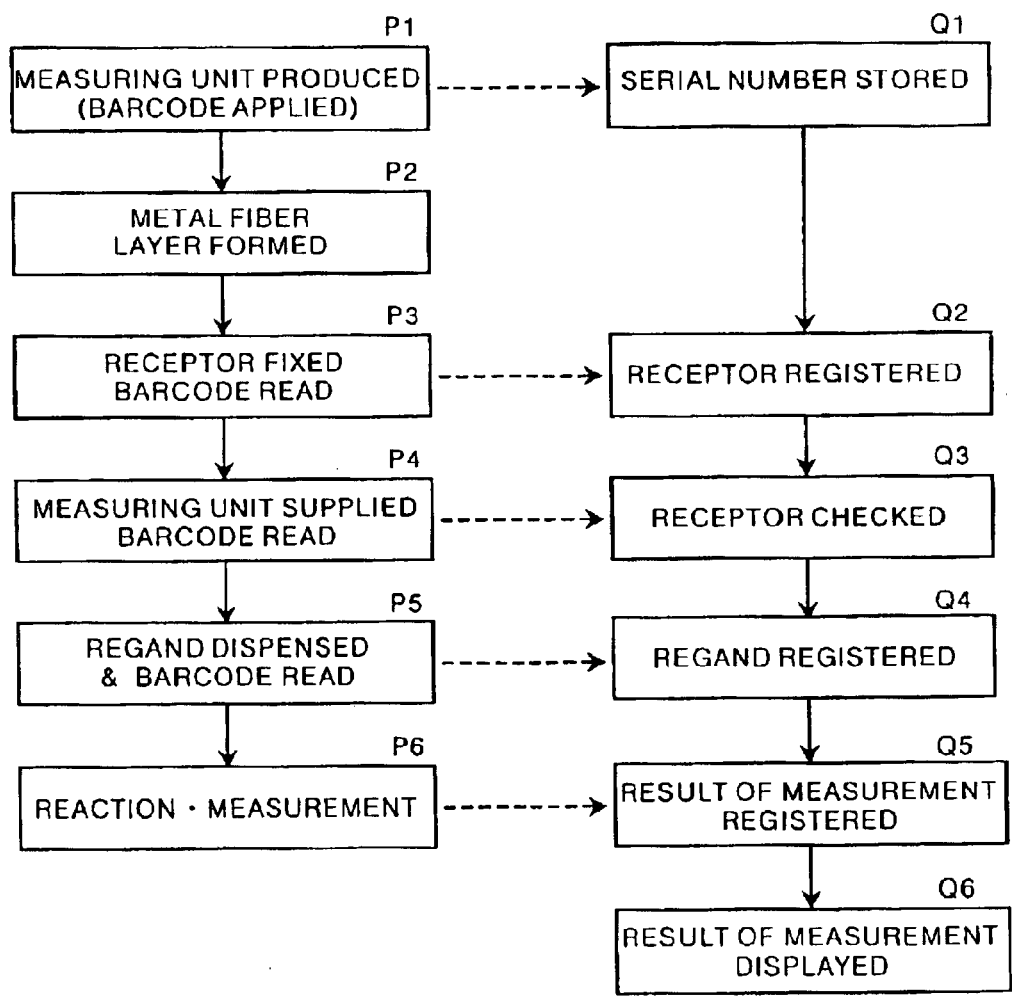
FIG. 30 is a view for illustrating the flow of control and information processing in the surface plasmon resonance sensor shown in FIG. 29.

In FIG. 30, the flow of image processing by the computer systems 600 and 610 is shown on the right side of FIG. 30, and the flow of operation related to the image processing is shown on the left side of FIG. 30.

First a measuring unit 80 is produced by a maker. At this time, a barcode 80b representing the serial number of the measuring unit 80 is applied to the measuring unit 80. (step P1) At the same time, the serial number represented by the barcode 80b is stored in a predetermined memory of the computer system 600, for instance, through the keyboard 603 for production control of the measuring units 80. (step Q1) After the barcode 80b is applied to the measuring unit 80, a metal film layer is formed on the dielectric block of the measuring unit 80. (step P2)

Then the receptor is fixed on the measuring unit 80. (step P3) At this time, the first barcode reader 604 reads the serial number represented by the barcode 80b of the measuring unit 80 and information F on the kind of the receptor fixed on the measuring unit 80 is input through the keyboard 603. The information F and the serial number of the measuring unit 80 are stored and registered in the memory means in the computer system 600 correlated to each other. (step Q2) The computer system 600 transfers the information F to the computer system 610 through the internet or an executive communication circuit. The computer system 610 stores the information F in a predetermined memory means.

The measuring unit 80 fixed with the receptor is placed on the turntable 20 of the apparatus shown in FIG. 29. The serial number represented by the barcode 80b on the measuring unit 80 is read by the second barcode reader 614 (before or after the measuring unit 80 is placed on the turntable 20) and input into the computer system 610. (step P4) The computer system 610 reads out the kind of receptor corresponding to the input serial number on the basis of the information F stored therein and causes the display 612 to display the kind of receptor. The operator can ascertain whether the receptor on the measuring unit 80 is corrected. (step Q3)

Then the regands are dispensed to the measuring units 80 supported on the turntable 20 and the barcode 242b representing the kinds of the regands in the wells of the well-plate 242 is read by the third barcode reader 620. (step P5)

The regands in the wells of the well-plate 242 are dispensed to the measuring units 80 in a predetermined order, and at the same time, the measuring units 80 are sent to the regand dispensing position after passing through the second barcode reader 614. The computer system 610 determines the kind of the regand dispensed to each measuring unit 80 on the basis of information G from the second barcode reader 614 and information H from the third barcode reader 620 and stores and registers the kind of the regand in correlation with the serial number of the measuring unit 80.

(step Q4)

After lapse of a predetermined time required for the receptor and the regand to react with each other, surface plasmon resonance measurement is carried out on the measuring units 80 supported on the turntable 20. (step P6) Measurement in this embodiment is carried out in order to find a regand which can bond to the receptor, and is carried out on the basis of the output signal S of the photodetector 40 as in the ninth embodiment shown in FIGS. 14 and 15.

The computer system 610 determines the result of reaction between the receptors and the regands and determines the bonding state of the receptors and regands on the basis of the result of reaction. The result of measurement is stored and registered in the memory means in correlation to the serial numbers of the measuring units 80. (step Q5)

The result of measurement thus obtained is displayed by the display 612 of the computer system 610, for instance, as shown in the following table 1. (step Q6)

TABLE 1

| cup No. | receptor | regand | result of reaction | judgment |
|---------|----------|--------|--------------------|----------|
| 22668000 | A | 10001 | 5 | X |
| 22668001 | A | 10002 | 2 | X |
| 22668002 | A | 10003 | 0 | X |
| 22668003 | A | 10004 | 250 | ○ |
| 22668004 | B | 10005 | 10 | X |
| 22668005 | B | 10006 | 1340 | ○ |
| . | . | . | . | . |
| . | . | . | . | . |
| . | . | . | . | . |

As described above, in this embodiment, since each of the kind of the receptor, the kind of the regand and the result of measurement is stored in correlation with the serial number of the measuring unit 80, there is no fear that measurement is carried out on an unintended combination of the receptor and the regand or result of measurement for one combination of the receptor and the regand is mistaken for that of a different combination.

As the identification mark for identifying the measuring units 80 from each other, other magnetic recording layers, a semiconductor memory, printed characters read by an OCR or the like may be used.

Further, though in the embodiment described above, the result of measurement is displayed by a display 612 of the computer system 610, the result of measurement may be printed out on a recording paper.

A sixteenth embodiment of the present invention will be described hereinbelow. FIG. 31 is a fragmentary perspective view showing an important part of a surface plasmon resonance sensor in accordance with the sixteenth embodiment of the present invention. The surface plasmon resonance sensor of this embodiment differs from that shown in FIG. 5 in the structure of the optical system which converges the light beam 30 and the dielectric block. That is, in this embodiment, a dielectric block 780 which is like a rectangular prism in shape is employed and the metal film layer 12 is formed on the upper surface of the dielectric block 780. The optical system comprises a collimator lens 781 which collimates the light beam 30 emitted from a laser 31 such as a semiconductor laser as a divergent light beam into a parallel light beam, a cylindrical lens 782 which converges the collimated light beam 30 only in one direction into a wedge-shaped light beam, and a cylindrical lens 783 which converges into a parallel light beam the light beam 30 which is reflected in total internal reflection at the interface 780a between the dielectric block 780 and the metal film layer 12 and is divergent only in one direction.

The cylindrical lens 782 is disposed so that the wedge-shaped light beam 30 is not focused on the interface 780a. Accordingly, the spot size of the light beam 30 on the interface 780a is relatively large and about 500 μm×1000 μm (substantially rectangular). Accordingly, the measured value reflects the average of the fine irregularities on the surface of the metal film layer 12, whereby fluctuation of the measured values can be suppressed.

Figure 5:
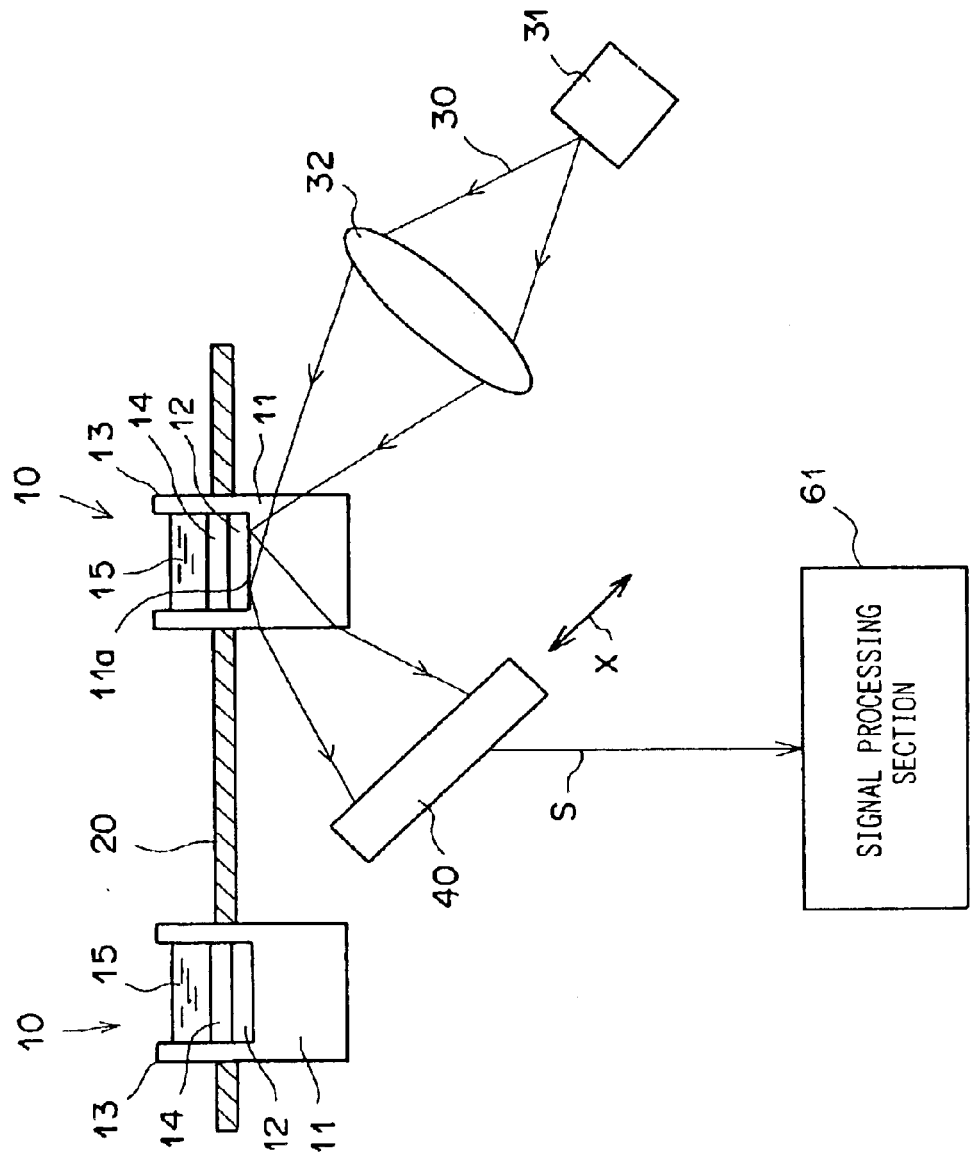
FIG. 5 is a side view partly cut away showing an important part of a surface plasmon resonance sensor in accordance with a third embodiment of the present invention.

It is possible to fix a sensing medium similar to the sensing medium 14 shown in FIG. 5 on the surface of the metal film layer 12 and cause the sensing medium to react with a specific material in the sample liquid 15. Also in this case, when the spot size of the light beam 30 on the interface 780a is relatively large, the measured value reflects the average of the bonding reaction properties, whereby fluctuation of the measured values can be suppressed.

Further, by the use of the cylindrical lens optical system, an optical system for correcting distortion of the dark line on the light receiving face of the photodetector 40 becomes unnecessary, which reduces the cost of the optical system.

Though, in the above embodiments, the light beam is caused to impinge upon the interface between the dielectric block and the metal film layer in a defocused state by an arrangement of the optical system, other arrangements may be employed to cause the light beam to impinge upon the interface between the dielectric block and the metal film layer in a defocused state.

Figure 32:
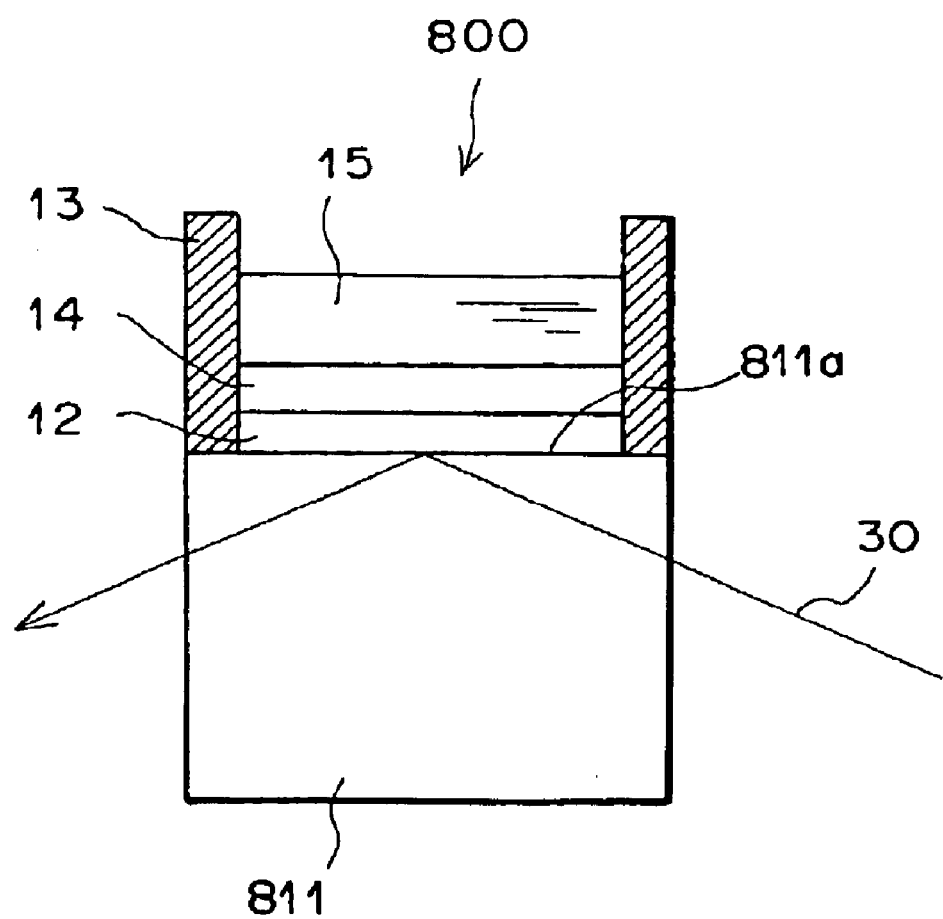
FIG. 32 is a side view partly cut away of another example of the measuring unit employed in the surface plasmon resonance sensor of the present invention.

For example, the measuring unit 800 shown in FIG. 32 is arranged so that the transparent dielectric block 811 forms apart of an optical system which causes the light beam to impinge upon the interface between the dielectric block and the metal film layer in a defocused state. That is, the measuring unit 800 comprises a rectangular transparent dielectric block 811, a metal film layer 12 of gold, silver, copper, aluminum or the like formed on the upper surface of the dielectric block 811, a sensing medium 14 fixed on the metal film layer 12, and a sample holder frame 13 which defines a space with closed sides above the metal film layer 12.

When the light beam 30 is caused to enter the rectangular dielectric block 811 as a convergent light beam, astigmatism is caused due to the shape of the transparent dielectric block 811 and the light beam 30 impinges upon the interface 811a between the dielectric block 811 and the metal film layer 12 in a defocused state.

Figure 33:
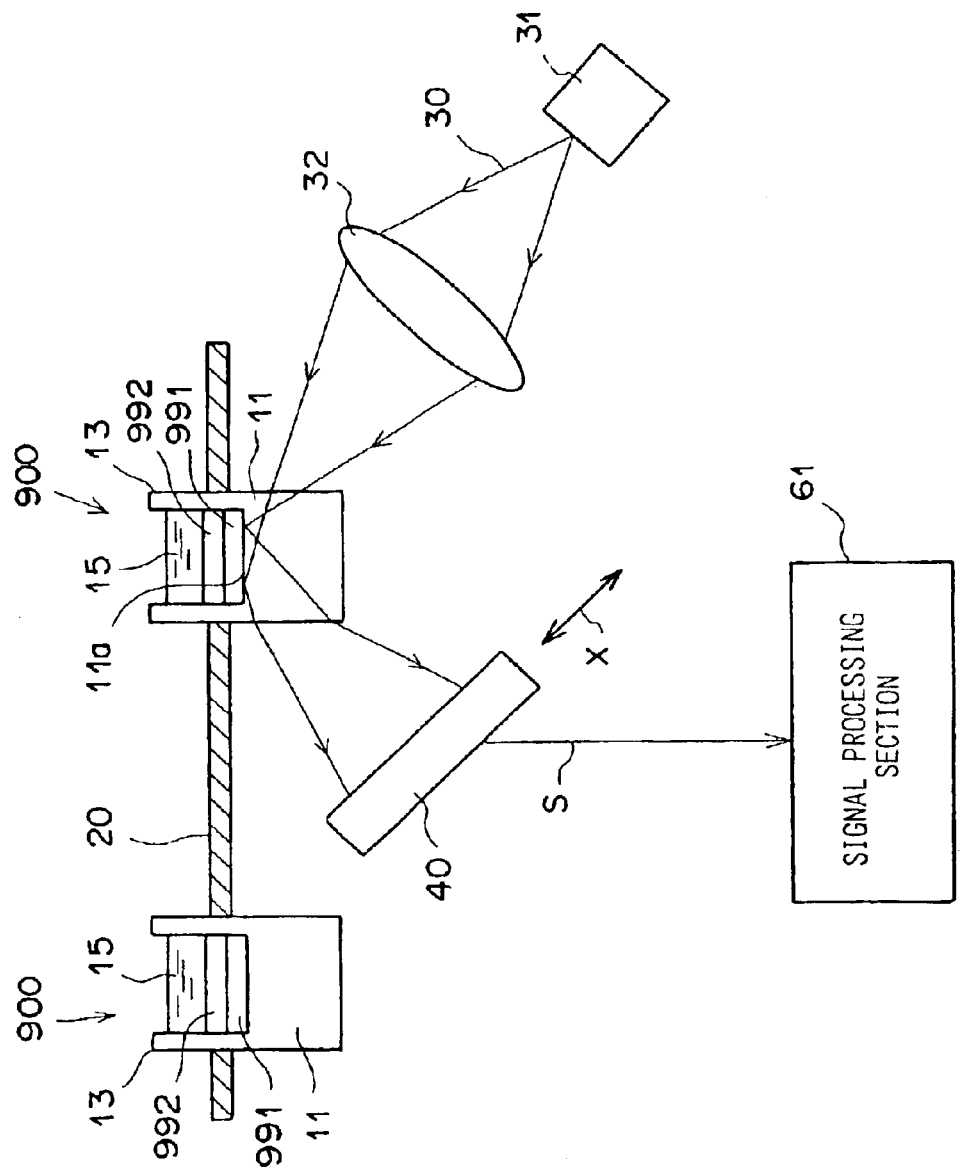
FIG. 33 is a side view partly cut away of a leaky mode sensor in accordance with a seventeenth embodiment of the present invention.

A seventeenth embodiment of the present invention will be described with reference to FIG. 33, hereinbelow. The sensor utilizing the phenomenon of attenuation in total internal reflection of the seventeenth embodiment is a leaky mode sensor described above, and also in this embodiment, measuring units 990 integrated into a measuring chip are employed. The measuring unit 990 comprises a dielectric block 11 and a clad layer 991 is formed on a surface (the upper surface as seen in FIG. 33) of the dielectric block 11. Further an optical waveguide layer 992 is formed on the clad layer 991.

The dielectric block 11 is formed of, for instance, synthetic resin or optical glass such as BK7. The clad layer 991 is formed of dielectric material lower than the dielectric block 11 in refractive index or metal such as gold. The optical wave guide layer 992 is film formed of dielectric material such as PMMA which is higher than the clad layer 991 in refractive index. The thickness of the clad layer 991 is 36.5 nm when it is formed of gold film, and the thickness of the optical waveguide layer 992 is about 700 nm when it is formed of PMMA.

In the leaky mode sensor, when the light beam 30 emitted from the laser 31 is caused to impinge upon the clad layer 991 at an angle not smaller than an angle of total internal reflection through the dielectric block 11, the light beam 30 is reflected in total internal reflection at the interface 11a of the dielectric block 11 and the clad layer 991, and only light having a particular wave number and impinging upon the waveguide layer 992 at a particular angle of incidence comes to propagate through the optical waveguide layer 992 in a waveguide mode after passing through the clad layer 991. When the waveguide mode is thus excited, almost all the incident light is taken in the optical waveguide layer 992 and accordingly, the intensity of light reflected in total internal reflection at the interface 11a of the dielectric block 11 and the clad layer 991 sharply drops. That is, attenuation in total internal reflection occurs.

Since the wave number of light to be propagated through the optical waveguide layer 992 in a waveguide mode depends upon the refractive index of the sample 15 on the optical waveguide layer 992, the refractive index and/or the properties of the sample related to the refractive index can be detected on the basis of the angle of incidence at which the attenuation in total internal reflection occurs. The signal processing section 61 quantitatively analyzes the specific material in the sample 15 under this principle and the result of analysis is displayed on a display (not shown).

The condenser lens 32 is disposed so that the conical light beam 30 is not focused on the interface 11a. Accordingly, the spot size of the light beam 30 on the interface 11a is relatively large and about 500 μm×500 μm. Accordingly, the measured value reflects the average of the fine irregularities on the surface of the clad layer 991 and/or the optical waveguide layer 992, whereby fluctuation of the measured values can be suppressed.

A method of measuring surface plasmon resonance in accordance with an embodiment of the present invention will be described, hereinbelow. FIGS. 34A to 34G are views for illustrating the flow of control in the surface plasmon resonance measuring method in accordance with the embodiment of the present invention.

In FIGS. 34A to 34G, reference numerals 100 and 200 respectively denotes a measuring unit and a turntable. The measuring unit 100 is basically the same as the measuring unit 10 shown in FIG. 1 and comprises a dielectric block, a metal film layer and a sample holder frame integrated into a measuring chip. Here the measuring unit will be referred to as "the measuring chip". The turntable 200 is provided with ninety-six (96) chip supporting portions 300 arranged at regular angular intervals (FIGS. 34A to 34G show only part of the ninety-six chip supporting portions 300), and is intermittently rotated by a predetermined angle equal to the angular intervals of the chip supporting portions 400 each time. The time intervals between intermittent rotations are two seconds in this particular embodiment.

Positions indicated at F1, F2, F3, F4 and F5 in FIGS. 34A to 34G are measuring chip supply position, a sensing medium supply position, a measuring position, a sample injection position and a measuring chip discharge position, respectively. The sensing material is a material which bonds to a specific material in the sample as the sensing medium 14 shown in FIG. 2 and specific examples of the sensing material are as described above.

Figure 34A:
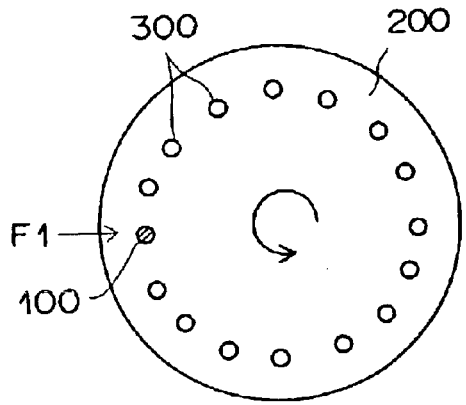
FIGS. 34A to 34G are views for illustrating the flow of control in a surface plasmon resonance measuring method in accordance with an embodiment of the present invention.
Figure 34B:
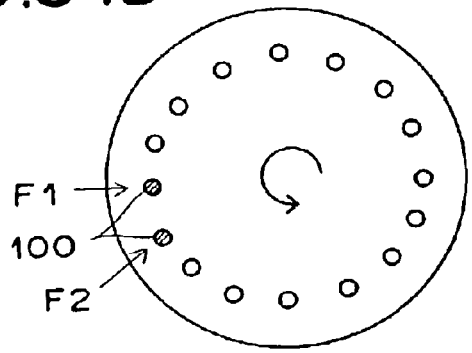

As shown in FIG. 34A, a measuring chip 100 in which a sensing medium fixing film has been fixed on the metal film layer is supplied to a chip supporting portion 300 of the turntable 200 opposed to the measuring chip supply position F1.

Then the turntable 200 is once rotated by the predetermined angle so that the measuring chip 100 on the chip supporting portion 300 is brought to the sensing medium supply position, and a sensing medium is supplied to the measuring chip 100.

Figure 34C:
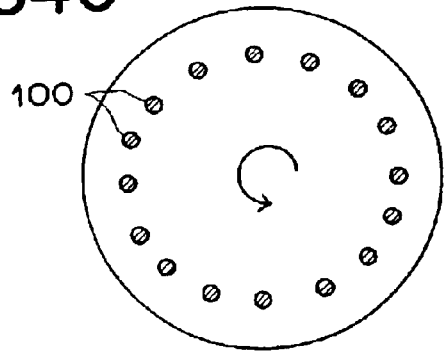
Figure 34D:
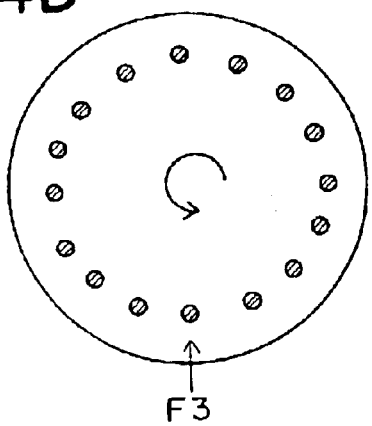

Supply of the sensing medium is carried out in parallel to supply of the measuring chip 100. When the turntable 200 is intermittently rotated 96 times, i.e., when the turntable 200 makes one rotation, the turntable 200 returns to the initial position with all the chip supporting portions 300 occupied with measuring chips 100 with a sensing medium. The time required for the turntable 200 to return to the initial position is 192 seconds (2×96). FIG. 34C shows the turntable 200 in this state. Then the surface plasmon resonance sensor is kept in this state for a predetermined time interval as required.

Then surface plasmon resonance is measured in the measuring position F3 on each other measuring chips 100 before supplied with a sample, and the output signal S of the photodetector 40 (See, e.g., FIG. 2) in this state is detected as a base line of measurement.

Figure 34E:
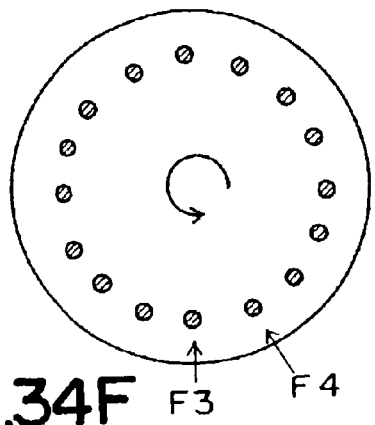

When the turntable 200 is intermittently rotated another time, the measuring chip 100 whose base line is just detected in the measuring position F3 is brought to the sample injection position F4 shown in FIG. 34E and a sample is injected into the measuring chip 100.

Injection of the sample is carried out in parallel to detection of the base line. By the time the turntable 200 makes another rotation and returns to the initial position, base line detection and sample injection have been carried out on all the measuring chips 100.

Figure 34F:
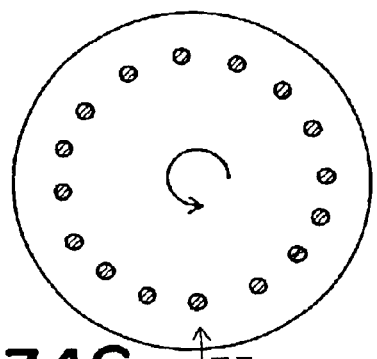
Figure 34G:
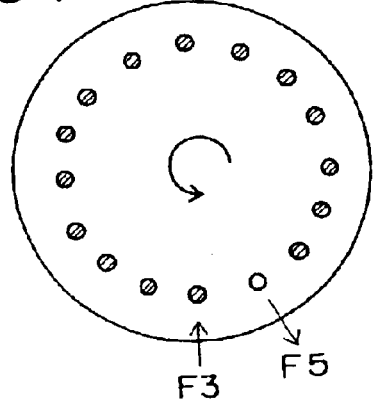

Then as shown in FIG. 34F, surface plasmon resonance measurement is carried out on the measuring chip 100 which is stopped in the measuring position F3. At this time, the measuring chip 100 is loaded with a sample and the total reflection attenuation angle θsp is detected. By the time the turntable 200 is intermittently rotated 96 times and returns to the initial position again, surface plasmon resonance measurement has been carried out once on all the measuring chips 100.

By carrying out surface plasmon resonance measurement on the measuring chip 100 which is stopped in the measuring position F3 each time the turntable 200 is intermittently rotated, measurement can be carried out a plurality of times according to the number of rotations of the turntable 200 on each measuring chip 100.

In accordance with the method of surface plasmon resonance measurement of this embodiment, since surface plasmon resonance measurement can be carried out on the other measuring chips 100 between the time surface plasmon resonance measurement is carried out one measuring chip 100 and the time surface plasmon resonance measurement is carried out again on the same measuring chip 100, lots of samples can be efficiently measured in a short time.

When the turntable 200 starts making an n-th rotation, n-th measurement is carried out on each measuring chip 100. Each measuring chip 100 is removed from the turntable 200 in the measuring chip discharge position F5 shown in FIG. 34G after the n-th measurement.

After injection of the sample into all the measuring chips 100 on the turntable 200 is finished, the turntable 200 may be kept stopped for a predetermined time to wait for start of reaction between the sample and the sensing medium.

FIG. 35 shows an example of result of multiple-time measurement. In FIG. 35, "sampling time" on the abscissa represents the time up to each measurement after injection of the sample, whereas "amount of bonded material" on the ordinate represents the amount of the specific material specifically bonded to the sensing medium, which corresponds to change of surface plasmon resonance detecting signal or movement of the aforesaid dark line.

As can be understood from FIG. 35, surface plasmon resonance is measured a plurality of times, the time required for the amount of bonded material to be saturated or the like can be known as well as the final amount of bonded material.

Though a method of surface plasmon resonance measurement in which a turntable 200 is employed has been described, the present invention can be applied also to a method where a support is linearly moved back and forth.

What is claimed is:

1. A measuring apparatus utilizing the phenomenon of attenuation in total internal reflection comprising
   a plurality of measuring units each comprising a dielectric block, a film layer which is formed on a surface of the dielectric block and a sample holder which holds a sample on the surface of the film layer,
   a support which supports the measuring units,
   a light source which emits a light beam,
   an optical system which causes the light beam to enter the dielectric block at various angles of incidence so that the total internal reflection condition is satisfied at an interface of the dielectric block and the film layer,
   a photodetector which detects attenuation in total internal reflection by detecting the intensity of the light beam which is reflected in total internal reflection at the interface,
   a drive means which causes relative movement between the support and an assembly of the optical system and the photodetector to bring the measuring units in sequence to a predetermined position with respect to the optical system and the photodetector where the total internal reflection condition is satisfied at the interface of the dielectric block and the film layer and various angles of incidence to the interface can be obtained, and
   an automatic sample feeding means which automatically feeds a sample to the sample holder of each of the measuring units.

2. A measuring apparatus utilizing the phenomenon of attenuation in total internal reflection comprising
   a plurality of measuring units each comprising a dielectric block, a film layer which is formed on a surface of the dielectric block, sensing material which interacts a specific component in a sample and is disposed on the surface of the film layer, and a sample holder which holds the sample on the surface of the sensing material,
   a support which supports the measuring units,
   a light source which emits a light beam,
   an optical system which causes the light beam to enter the dielectric block at various angles of incidence so that the total internal reflection condition is satisfied at an interface of the dielectric block and the film layer,
   a photodetector which detects attenuation in total internal reflection by detecting the intensity of the light beam which is reflected in total internal reflection at the interface,
   a drive means which causes relative movement between the support and an assembly of the optical system and the photodetector to bring the measuring units in sequence to a predetermined position with respect to the optical system and the photodetector where the total internal reflection condition is satisfied at the interface of the dielectric block and the film layer and various angles of incidence to the interface can be obtained, and
   an automatic sample feeding means which automatically feeds a sample to the sample holder of each of the measuring units.

3. A measuring apparatus utilizing the phenomenon of attenuation in total internal reflection comprising
   a plurality of measuring units each comprising a dielectric block, a metal film layer which is formed on a surface of the dielectric block and a sample holder which holds a sample on the surface of the metal film layer,
   a support which supports the measuring units,
   a light source which emits a light beam,
   an optical system which causes the light beam to enter the dielectric block at various angles of incidence so that the total internal reflection condition is satisfied at an interface of the dielectric block and the metal film layer,
   a photodetector which detects attenuation in total internal reflection by surface plasmon resonance by detecting the intensity of the light beam which is reflected in total internal reflection at the interface,
   a drive means which causes relative movement between the support and an assembly of the optical system and the photodetector to bring the measuring units in sequence to a predetermined position with respect to the optical system and the photodetector where the total internal reflection condition is satisfied at the interface of the dielectric block and the metal film layer and various angles of incidence to the interface can be obtained, and
   an automatic sample feeding means which automatically feeds a sample to the sample holder of each of the measuring units.

4. A measuring apparatus utilizing the phenomenon of attenuation in total internal reflection comprising
   a plurality of measuring units each comprising a dielectric block, a metal film layer which is formed on a surface of the dielectric block, sensing material which interacts a specific component in a sample and is disposed on the surface of the metal film layer, and a sample holder which holds the sample on the surface of the sensing material,
   a support which supports the measuring units,
   a light source which emits a light beam,
   an optical system which causes the light beam to enter the dielectric block at various angles of incidence so that the total internal reflection condition is satisfied at an interface of the dielectric block and the metal film layer,
   a photodetector which detects attenuation in total internal reflection by surface plasmon resonance by detecting the intensity of the light beam which is reflected in total internal reflection at the interface,
   a drive means which causes relative movement between the support and an assembly of the optical system and the photodetector to bring the measuring units in sequence to a predetermined position with respect to the optical system and the photodetector where the total internal reflection condition is satisfied at the interface of the dielectric block and the metal film layer and various angles of incidence to the interface can be obtained, and
   an automatic sample feeding means which automatically feeds a sample to the sample holder of each of the measuring units.

5. A measuring apparatus utilizing the phenomenon of attenuation in total internal reflection comprising
- a plurality of measuring units each comprising a dielectric block, a film layer consisting of a clad layer formed on a surface of the dielectric block and an optical waveguide layer formed on the clad layer, and a sample holder which holds a sample on the surface of the film layer,
- a support which supports the measuring units,
- a light source which emits a light beam,
- an optical system which causes the light beam to enter the dielectric block at various angles of incidence so that the total internal reflection condition is satisfied at an interface of the dielectric block and the clad layer,
- a photodetector which detects attenuation in total internal reflection by excitation of waveguide mode at the optical waveguide layer by detecting the intensity of the light beam which is reflected in total internal reflection at the interface, and
- a drive means which causes relative movement between the support and an assembly of the optical system and the photodetector to bring the measuring units in sequence to a predetermined position with respect to the optical system and the photodetector where the total internal reflection condition is satisfied at the interface of the dielectric block and the clad layer and various angles of incidence to the interface can be obtained.

6. A measuring apparatus utilizing the phenomenon of attenuation in total internal reflection comprising a plurality of measuring units each comprising
- a dielectric block, a film layer consisting of a clad layer formed on a surface of the dielectric block and an optical waveguide layer formed on the clad layer, sensing material which interacts a specific component in a sample and is disposed on the surface of the film layer, and a sample holder which holds the sample on the surface of the sensing material,
- a support which supports the measuring units,
- a light source which emits a light beam,
- an optical system which causes the light beam to enter the dielectric block at various angles of incidence so that the total internal reflection condition is satisfied at an interface of the dielectric block and the clad layer,
- a photodetector which detects attenuation in total internal reflection by excitation of waveguide mode at the optical waveguide layer by detecting the intensity of the light beam which is reflected in total internal reflection at the interface, and
- a drive means which a drive means which causes relative movement between the support and an assembly of the optical system and the photodetector to bring the measuring units in sequence to a predetermined position with respect to the optical system and the photodetector where the total internal reflection condition is satisfied at the interface of the dielectric block and the clad layer and various angles of incidence to the interface can be obtained.

7. A measuring apparatus utilizing the phenomenon of attenuation in total internal reflection as defined in any one of claims 1 to 6 in which the drive means moves the support, and the optical system and the photodetector are kept stationary.

8. A measuring apparatus utilizing the phenomenon of attenuation in total internal reflection as defined in claim 7 in which the support comprises a turntable which supports the measuring units about an axis of rotation of the turntable and the drive means intermittently rotates the turntable.

9. A measuring apparatus utilizing the phenomenon of attenuation in total internal reflection as defined in claim 7 in which the support supports the measuring units in a row and the drive means intermittently moves the support in the direction of the row of the measuring units.

10. A measuring apparatus utilizing the phenomenon of attenuation in total internal reflection as defined in any one of claims 1 to 6 in which the drive means moves the optical system and the photodetector, and the support is kept stationary.

11. A measuring apparatus utilizing the phenomenon of attenuation in total internal reflection as defined in claim 10 in which the support supports the measuring units in a row and the drive means intermittently moves the optical system and the photodetector along the measuring units in a row.

12. A measuring apparatus utilizing the phenomenon of attenuation in total internal reflection as defined in claim 10 in which the support supports the measuring units in a circle and the drive means intermittently moves the optical system and the photodetector along the measuring units in a circle.

13. A measuring apparatus utilizing the phenomenon of attenuation in total internal reflection as defined in claim 8 in which the drive means is provided with a roller bearing which supports its rotating shaft, and the drive means is arranged to rotate the rotating shaft in one direction when a set of measuring units on the support are measured and to rotate the rotating shaft in the other direction to return the rotating shaft to the original position after the measurement on the measuring units to wait in the original position for measurement on another set of measuring units.

14. A measuring apparatus utilizing the phenomenon of attenuation in total internal reflection as defined in claim 9 in which the measuring units are connected in a row to form a measuring unit train, and the support is arranged to support the measuring unit train.

15. A measuring apparatus utilizing the phenomenon of attenuation in total internal reflection as defined in any one of claims 5 and 6, further comprising an automatic sample feeding means which automatically feeds a sample to the sample holder of each of the measuring units.

16. A measuring apparatus utilizing the phenomenon of attenuation in total internal reflection as defined in any one of claims 1 to 6 in which the dielectric block of each measuring unit is fixed to the support while the film layer and the sample holder are integrated with each other to form a measuring chip, and the measuring chips are exchangeable with respect to the dielectric block.

17. A measuring apparatus utilizing the phenomenon of attenuation in total internal reflection as defined in claim 16 further comprising a measuring chip cassette in which plurality of measuring chips are contained, and a chip supply means which takes out the measuring chips from the measuring chip cassette one by one and mounts each measuring chip on the dielectric block.

18. A measuring apparatus utilizing the phenomenon of attenuation in total internal reflection as defined in any one of claims 1 to 6 in which the dielectric block, the film layer and the sample holder of the measuring unit are integrated with each other to form a measuring chip which is exchangeable with respect to the support.

19. A measuring apparatus utilizing the phenomenon of attenuation in total internal reflection as defined in claim 18 further comprising a measuring chip cassette in which plurality of measuring chips are contained, and a chip supply means which takes out the measuring chips from the measuring chip cassette one by one and mounts each measuring chip on the support.

20. A measuring apparatus utilizing the phenomenon of attenuation in total internal reflection as defined in any one of claims 1 to 6 in which the optical system is arranged to cause the light beam to enter the dielectric block as a convergent light beam or a divergent light beam, and the photodetector is arranged to detect a position of a dark line which is generated in the light beam reflected in total internal reflection at the interface due to attenuation in total reflection.

21. A measuring apparatus utilizing the phenomenon of attenuation in total internal reflection as defined in claim 20 in which the optical system is arranged to cause the light beam to impinge upon the interface in a defocused state.

22. A measuring apparatus utilizing the phenomenon of attenuation in total internal reflection as defined in claim 21 in which the beam diameter of the light beam as measured on the interface in the direction of movement of the support is at least ten times the mechanical positioning accuracy of the support.

23. A measuring apparatus utilizing the phenomenon of attenuation in total internal reflection as defined in any one of claims 1 to 6 in which the measuring units are supported on the upper side of the support, the light source is arranged to emit the light beam downward from above the support, and the optical system is provided with a reflecting member which reflects upward the light beam toward the interface.

24. A measuring apparatus utilizing the phenomenon of attenuation in total internal reflection as defined in any one of claims 1 to 6 in which the measuring units are supported on the upper side of the support, the optical system is arranged to cause the light beam to impinge upon the interface from below the interface, the photodetector is positioned above the support with its light receiving face directed downward, and a reflecting member which reflects the light beam, reflected in total internal reflection at the interface, upward toward the photodetector is provided.

25. A measuring apparatus utilizing the phenomenon of attenuation in total internal reflection as defined in any one of claims 1 to 6 further comprising a temperature control means which maintains the temperature of the measuring units at a predetermined temperature before and/or after the measuring units are supported by the support.

26. A measuring apparatus utilizing the phenomenon of attenuation in total internal reflection as defined in any one of claims 1 to 6 further comprising a stirrer means which stirs the sample held by the sample holder of the measuring unit supported by the support before attenuation in total internal reflection is detected.

27. A measuring apparatus utilizing the phenomenon of attenuation in total internal reflection as defined in any one of claims 1 to 6 in which a reference liquid supply means which supplies at least one of the measuring units supported by the support with reference liquid which has optical properties related to the optical properties of the sample is provided, and data on the state of attenuation in total internal reflection for the sample obtained by the photodetector is corrected on the basis of data on the state of total internal reflection for the reference liquid.

28. A measuring apparatus utilizing the phenomenon of attenuation in total internal reflection as defined in claim 27 in which the sample comprises a sample material dissolved in solvent, and the reference liquid supply means supplies the solvent as the reference liquid.

29. A measuring apparatus utilizing the phenomenon of attenuation in total internal reflection as defined in any one of claims 1 to 6 further comprising an identification mark provided on each of the measuring units, a reading means which reads out the identification mark from each of the measuring units subjected to the measurement, a sample information input means which inputs information on the samples fed to the respective measuring units, a display means which displays the result of the measurement, and a control means which is connected to the display means, the sample information input means and the reading means to store the identification mark for each measuring unit and the information on the sample fed to the measuring unit correlated to each other and causes the display means to display the result of the measurement on the sample held by a measuring unit in correlation with the identification mark for the measuring unit and the information on the sample fed to the measuring unit stored correlated to each other.

30. A measuring method employing a measuring apparatus utilizing the phenomenon of attenuation in total internal reflection as defined in any one of claims 1 to 6 the comprising the steps of detecting attenuation in total internal reflection for the sample held in first one of the measuring units, moving the support relatively to the optical system and the photodetector to bring a second one of the measuring units to the predetermined position with respect to the optical system and the photodetector and detecting attenuation in total internal reflection for the sample held in the second one of the measuring units, and moving the support relatively to the optical system and the photodetector to bring the first one of the measuring units again to the predetermined position with respect to the optical system and the photodetector and detecting again attenuation in total internal reflection for the sample held in the first one of the measuring units.

31. A measuring apparatus utilizing the phenomenon of attenuation in total internal reflection comprising a dielectric block, a film layer which is formed on one surface of the dielectric block and is brought into contact with a sample, a light source which emits a light beam, an optical system which causes the light beam to enter the dielectric block in convergent light so that the total internal reflection condition is satisfied at the interface of the dielectric block and the film layer and various angles of incidence of the light beam to an interface of the dielectric block and the film layer can be obtained, and a photodetector which detects attenuation in total internal reflection by detecting the intensity of the light beam which is reflected in total internal reflection at the interface, wherein the optical system is arranged so that the light beam is not focused on the interface.

32. A measuring apparatus utilizing the phenomenon of attenuation in total internal reflection comprising
a dielectric block,
a metal film layer which is formed on one surface of the dielectric block and is brought into contact with a sample,
a light source which emits a light beam,
an optical system which causes the light beam to enter the dielectric block in convergent light so that the total internal reflection condition is satisfied at an interface to the dielectric block and the metal film layer and various angles of incidence of the light beam to the interface of the dielectric block and the metal film layer can be obtained, and
a photodetector which detects attenuation in total internal reflection by surface plasmon resonance by detecting the intensity of the light beam which is reflected in total internal reflection at the interface,
wherein the optical system is arranged so that the light beam is not focused on the interface.

33. A measuring apparatus utilizing the phenomenon of attenuation in total internal reflection comprising
a dielectric block,
a film layer which is formed of a clad layer formed on a surface of the dielectric block and an optical waveguide layer formed on the clad layer and is brought into contact with a sample,
a light source which emits a light beam,
an optical system which causes the light beam to enter the dielectric block in convergent light so that the total internal reflection condition is satisfied at the interface of the dielectric block and the clad layer and various angles of incidence of the light beam to an interface of the dielectric block and the clad layer can be obtained, and
a photodetector which detects attenuation in total internal reflection by excitation of waveguide mode at the optical waveguide layer by detecting the intensity of the light beam
wherein the optical system is arranged so that the light beam is not focused on the interface.

34. A measuring apparatus utilizing the phenomenon of attenuation in total internal reflection as defined in any one of claims 31 to 33 in which the light be is at least 500 μm in a cross-sectional size at least in one direction on the interface.

35. A measuring apparatus utilizing the phenomenon of attenuation in total internal reflection as defined in any one of claims 31 to 33 in which the optical system focuses the light beam so that the interface is positioned outside the focal depth of the light beam.

36. A measuring apparatus utilizing the phenomenon of attenuation in total internal reflection as defined in any one of claims 31 to 33 in which the optical system is arranged so that the light beam is not focused on the interface due to its aberration.

37. A measuring apparatus utilizing the phenomenon of attenuation in total internal reflection as defined in any one of claims 31 to 33 in which the light beam is converged in a conical shape by a spherical lens.

38. A measuring apparatus utilizing the phenomenon of attenuation in total internal reflection as defined in any one of claims 31 to 33 in which the light beam is converged in a wedge-like shape by a cylindrical lens.

39. A measuring apparatus utilizing the phenomenon of attenuation in total internal reflection as defined in any one of claims 31 to 33 in which a sensing medium which makes bonding reaction with a specific material in the sample is fixed on the film layer.

40. A measuring apparatus utilizing the phenomenon of attenuation in total internal reflection as defined in any one of claims 31 to 33 further comprising a sample holder for holding the sample on the film layer.

41. A measuring apparatus utilizing the phenomenon of attenuation in total internal reflection as defined in any one of claims 31 to 33 further comprising a sample introduction mechanism for introducing the sample onto the film layer.

42. A measuring method utilizing the phenomenon of attenuation in total internal reflection comprising the steps of
bringing a sample into contact with a film layer formed on one surface of a dielectric block,
causing a light beam to enter the dielectric block in convergent light so that the total internal reflection condition is satisfied at an interface of the dielectric block and the film layer and various angles of incidence of the light beam to the interface of the dielectric block and the film layer can be obtained, wherein the light beam to entering the dielectric block is not focused on the interface, and
detecting attenuation in total internal reflection by detecting the intensity of the light beam which is reflected in total internal reflection at the interface.

43. A measuring method utilizing the phenomenon of attenuation in total internal reflection comprising the steps of
bringing a sample into contact with a metal film layer formed on one surface of a dielectric block,
causing a light beam to enter the dielectric block in convergent light so that the total internal reflection condition is satisfied at an interface of the dielectric block and the metal film layer and various angles of incidence of the light beam to the interface of the dielectric block and the metal film layer can be obtained, wherein the light beam entering the dielectric block is not focused on the interface, and
detecting attenuation in total internal reflection by surface plasmon resonance by detecting the intensity of the light beam which is reflected in total internal reflection at the interface.

44. A measuring method utilizing the phenomenon of attenuation in total internal reflection comprising the steps of
bringing a sample into contact with an optical waveguide layer formed on a clad layer formed on one surface of a dielectric block,
causing a light beam to enter the dielectric block in convergent light so that the total internal reflection condition is satisfied at an interface of the dielectric block and the clad layer and various angles of incidence of the light beam to the interface of the dielectric block and the clad layer can be obtained, wherein the light beam entering the dielectric block is not focused on the interface and
detecting attenuation in total internal reflection by detecting the intensity of the light beam which is reflected in total internal reflection at the interface.

45. A measuring method utilizing the phenomenon of attenuation in total internal reflection as defined in any one of claims 42 to 44 in which the light be is caused to enter the dielectric block so as to be at least 500 μm in a cross-sectional size at least in one direction on the interface.

* * * * *